United States Patent [19]

Hou et al.

[11] Patent Number: 5,059,654

[45] Date of Patent: Oct. 22, 1991

[54] AFFINITY MATRICES OF MODIFIED POLYSACCHARIDE SUPPORTS

[75] Inventors: Kenneth C. Hou, Glastonbury, Conn.; Tung-Ping D. Liao, Missouri City, Tex.; Robert Rohan, Columbia, Conn.

[73] Assignee: Cuno Inc., Meridan, Conn.

[21] Appl. No.: 311,498

[22] Filed: Feb. 16, 1989

Related U.S. Application Data

[63] Continuation-in-part of Ser. No. 154,815, Feb. 11, 1988, abandoned, which is a continuation-in-part of Ser. No. 130,186, Dec. 8, 1987, abandoned, which is a continuation-in-part of Ser. No. 13,512, Jan. 27, 1987, abandoned, which is a continuation-in-part of Ser. No. 656,922, Oct. 2, 1984, Pat. No. 4,639,513, which is a continuation-in-part of Ser. No. 576,448, Feb. 2, 1984, Pat. No. 4,663,163, which is a continuation-in-part of Ser. No. 466,114, Feb. 14, 1983, abandoned.

[51] Int. Cl.$^5$ .................. C08H 5/00; A61K 37/04; B01J 20/00; C07K 3/20

[52] U.S. Cl. .................. 525/54.1; 525/54.2; 525/54.21; 530/412; 530/413; 210/656; 210/198.2; 210/502.1; 422/59; 422/70; 422/89; 435/91; 435/180

[58] Field of Search .......... 525/54.1, 54.2, 54.21; 530/412, 413, 414, 415, 416, 417, 418; 422/59, 70, 89; 210/635, 656, 198.2, 198.3, 502.1; 435/91, 180, 897

[56] References Cited

U.S. PATENT DOCUMENTS

| | | | |
|---|---|---|---|
| 3,891,580 | 6/1975 | Morris et al. | 527/201 |
| 4,210,723 | 7/1980 | Dorman et al. | 530/398 |
| 4,224,439 | 9/1980 | Ayers et al. | 536/32 |
| 4,352,884 | 10/1982 | Nakashima et al. | 435/180 |
| 4,384,957 | 5/1983 | Crowder, III et al. | 210/656 |
| 4,385,991 | 5/1983 | Rosevear et al. | 210/635 |
| 4,421,650 | 12/1983 | Nagasawa et al. | 210/635 |
| 4,743,373 | 5/1988 | Rai et al. | 210/198.3 |

*Primary Examiner*—Nathan M. Nutter

[57] ABSTRACT

The invention is directed to a modified polysaccharide material which comprises: (1) polysaccharide covalently bonded to a synthetic polymer; (2) the synthetic polymer being made from (a) a polymerizable compound which is capable of being covalently coupled directly or indirectly to said polysaccharide, and (b) one or more polymerizable compounds containing (i) a chemical group capable of causing the covalent coupling of the compound (b) to an affinity ligand or a biologically active molecule or (ii) a hydrophobic compound.

The invention is also directed to devices for the chromatographic separation of at least two components of a mixture comprising the modified polysaccharide material of the invention, wherein the device is configured for radial or tangential flow.

28 Claims, 14 Drawing Sheets

AFFINITY MATRICES OF MODIFIED POLYSACCHARIDE SUPPORTS

The present application is a continuation-in-part of copending Application Ser. No. 154,815, filed Feb. 11, 1988, entitled "Affinity Matrices of Modified Polysaccharide supports, and now abandoned, which is a continuation-in-part of co-pending application Ser. No. 130,186, filed Dec. 8, 1987 entitled "Affinity Matrices of Modified Polysaccharide Supports," and now abandoned which is a continuation-in-part of application Ser. No. 013,512, filed Jan. 27, 1987, entitled "Affinity Matrices of Modified Polysaccharide Supports," and now abandoned which is a continuation-in-part of application Ser. No. 656,922, filed Oct. 2, 1984, now U.S. Pat. No. 4,639,513, issued Jan. 27, 1987, entitled "Intravenously Injectable Immunoglobulin G (IgG) and Method for Producing Same," which was a continuation-in-part of application Ser. No. 576,448, filed Feb. 2, 1984, now U.S. Pat. No. 4,663,163, issued May 5, 1987, entitled "Modified Polysaccharide Supports," which was a continuation-in-part of co-pending application Ser. No. 466,114, filed Feb. 14, 1983, entitled "Modified Polysaccharide Supports," now abandoned.

BACKGROUND OF THE INVENTION

1. Field of the Invention

The present invention relates to carrier supports such as chromatographic supports, and methods for their preparation and use. More particularly, the invention relates to carrier supports comprising a polymeric carrier grafted to a substrate for affinity chromatography media and for the affinity chromatography media made from these supports. The invention also relates to chromatographic devices which permit radial or tangential flow of a sample relative to the carrier support.

2. Brief Description of the Background Art

In the technique of affinity chromatography, which enables the efficient isolation of biological macromolecules or biopolymers by utilizing their recognition sites for certain supported chemical structures with a high degree of selectivity, the prior art has utilized materials of varying chemical structure as supports. For example, agarose gels and cross-linked agarose gels have been the most widely used support materials. Their hydrophilicity makes them relatively free of nonspecific binding, but their compressibility makes them less attractive as carriers in large scale processing, such as in manufacturing. Controlled-pore glass (CPG) beads have also been used in affinity chromatography. Although high throughputs can be obtained with columns packed with CPG, this carrier is even more expensive than agarose beads. Cellulose particles have also been used by immunochemists for synthetic affinity sorbents. However, compared to agarose gels, cellulose particles are formed with more difficulty and therefore, have received less attention in the preparation of affinity sorbents for enzymes. Cellulose, however, is perhaps the least expensive of all support matrices. Two lesser-used support matrices are polyacrylamide gel beads and Sephadex ® gel beads made from dextran and epichlorohydrin. Although convenient methods have been developed for using them, the softness of these beads yields poor column packings, and their low molecular porosity yields a sorbent with poor ligand availability to the ligate.

Coupek et al., U.S. Pat. No. 4,281,233, shows supports for affinity chromatography which comprise copolymers of hydroxy alkyl acrylates or methacrylates with cross-linking monomers. The copolymers contain covalently attached mono- or oligosaccharides. (An oligosaccharide is defined in the art as having up to nine saccharide units. See, e.g., Roberts, J. D., and Caserio, M. C., *Basic Principles of Organic Chemistry*, 1964, p. 615.)

A carrier for bio-active materials is also disclosed in Nakashima et al., U.S. Pat. No. 4,352,884. The Nakashima carrier comprises a substrate coated with a copolymer. The substrate may be one of various materials, including inorganic materials such as glass; silica; alumina; synthetic high polymers such as polystyrene, polyethylene, and the like; and naturally occurring high polymers such as cellulose. The copolymer is made of a hydrophilic acrylate or methacrylate monomer which is a hydroxy or alkoxyalkylacrylate or methacrylate, and a copolymerizable unsaturated carboxylic acid or amine. The base material or substrate is coated with the copolymer by conventional coating or deposition procedures, such as spraying, dipping, phase separation or the like. The copolymer may also contain small amounts of a cross-linking agent such as glycidyl acrylate or methacrylate. The cross-linking agent allows for cross-linking treatment after the coating process, and provides for the prevention of elution (presumably of the bioactive materials) from the coating layer. The amounts of cross-linking agent are quite small, and range between 0.5 and 1% by weight of the total copolymer weight. Such amounts of cross-linking agent are insufficient to cause substantial covalent bonding or grafting of the copolymer onto the underlying substrate. The copolymer in Nakashima is thus essentially only physically coating the underlying substrate. Physical coating, however, is accompanied by a series of problems. The carrier would not be expected to have an even distribution of the copolymer, would show a multilayered structure, and may have a possible uneven distribution of functional groups.

Another reference of interest is Kraemer, U.S. Pat. No. 4,070,348, which shows copolymers of glycidyl- and amino-containing acrylates, useful as carriers for biologically active substances, such as polysaccharides, enzymes, peptides, hormones, etc. The structure of the final product in Kraemer is that of an acrylic copolymer chain covalently modified at a multiplicity of sites thereon with substances such as enzymes, proteins, and the like.

This review of the prior art, its advantages and drawbacks, leads to the conclusion that there exists a need for a support useful both for ion exchange and affinity chromatography-based purification which will have high stability, high porosity, low non-specific adsorption, high flow rate, non-compressibility, controlled gelation, and which will be useful for industrial-scale biological separations. It is at the industrial level of manufacturing, especially, where the aforementioned drawbacks of the prior art have had their most important effect and where this need is the strongest.

Industrial-scale molecular separation materials comprising fibrous matrices with particulate immobilized therein have been described in commonly assigned U.S. Pat. No. 4,384,957 to Crowder, which is herein incorporated by reference. This patent describes a composite fiber material formed by wet laying a sheet from an aqueous slurry of particulate, small refined fiber pulp, and long soft fiber pulp.

Using a fibrous/particulate matrix with addition of cationic polymers to the slurry and cross-linking the polymers to the matrices by oven-drying has yielded a filtration matrix with a positive charge coated on the surface thereof. Such charged matrices can be used for filtering minute amounts of particulate impurities from large volumes of liquid by adsorption. (See, for example, Ostreicher, U.S. Pat. Nos. 4,007,113 and 4,007,114, as well as U.S. Pat. Nos. 4,305,782 and 4,309,247, which are all herein incorporated by reference.)

It is inevitable in prior art wet slurrying processes with slurries comprising cationic materials to obtain materials having uneven distribution of charges, wherein multilayer coating may occur in one spot, whereas other spots on the surface may be bare. Such products are acceptable in filtration processes due to the fact that the amount of impurities needed to be removed is relatively minor compared to the bulk liquid volume, and that uneven charge distributions can be compensated for by the depth of the filters. However, such products cannot readily be applied to delicate ion exchange processes. The number of active sites, as well as the accessibility of the active sites, are critical to the capacity of such processes. The chemical functional groups in ion exchangers cannot be buried close to the surface, but have to be somewhat removed from the surface, possibly with a molecular side arm for accessibility. One way of achieving this has been through the incorporation of particulates into a fibrous matrix modified by silanes which are chemically modified. Such silanes may carry functional groups such as DEAE, CM, or affinity chromatography sites. They are mechanically stable, strong and do not swell. However, they are expensive and show very high non-specific adsorption of protein by the silica hydroxy groups.

In sum, neither the affinity chromatography supports commonly used in laboratory-scale purifications nor the particulate- (or ion exchange modified particulate-) containing fibrous matrices for chromatography or filtration have proven to be of great use in scale-up of delicate affinity purification processes.

A need therefore continues to exist for supports useful in industrial-scale affinity chromatography purification processes, which will be noncompressible, controllably swellable, have high exchange capacity, exhibit high flow rates, be versatile, and be relatively inexpensive to produce, and for affinity matrices and devices comprising said supports.

SUMMARY OF THE INVENTION

It is therefore an object of the invention to provide a novel molecular support comprising a conjugate of a polymeric carrier and a substrate.

Another object of the invention is to provide a molecular support useful for affinity chromatography or reverse-phase chromatography.

Yet another object of the invention is to provide a chromatographic support useful for industrial-scale chromatographic operations.

Still another object of the invention is to provide industrial processes of affinity chromatography and reverse-phase chromatography.

Another object of the invention is to provide processes for the preparation of affinity and reverse-phase chromatographic supports and for affinity chromatographic media as well.

Yet another object of the invention is to provide devices which permit radial or tangential flow of a sample relative to the carrier support.

These and other objects of the invention as will hereinafter become more readily apparent have been attained by providing:

A modified polysaccharide material, which comprises:

1. a polysaccharide covalently bonded to a synthetic polymer;
2. said synthetic polymer made from
    a) a polymerizable compound which has a chemical group capable of being covalently coupled directly or indirectly to said polysaccharide; and
    b) one or more polymerizable compounds containing a chemical group capable of causing the covalent coupling of said polymerizable compound (b) to an affinity ligand or to a biologically active molecule.

Yet a further object of this invention has been attained by providing affinity molecular separation precursor compounds (hereinafter "pre-ligand intermediates") wherein said aforementioned modified polysaccharide materials are further modified to form preactivated intermediate compounds suitable for ligand coupling.

Another object of the invention has been attained by providing affinity molecular separation materials derived from the aforementioned polysaccharide materials, said affinity molecular separation materials comprising polysaccharide substrate, synthetic polymer covalently coupled to the polysaccharide substrate, and an affinity ligand covalently coupled to said synthetic polymer and capable of acting as chromatographic supports for affinity chromatography, reverse-phase chromatography, or as reagents for biochemical reactors.

Still another abject of the invention has been attained by providing molecular separation processes and/or biochemical reaction processes using the aforementioned materials.

In addition, a further object of the invention has been attained by providing devices for the chromatographic separation of at least two components of a sample whereby the device is configured to allow the sample to flow radially or tangentially with respect to the modified polysaccharide material.

BRIEF DESCRIPTION OF THE DRAWINGS

The present invention will become understood by reference to the detailed description provided hereinafter when considered together with the accompanying drawings, wherein.

BRIEF DESCRIPTION OF THE PREFERRED EMBODIMENTS

Figure 1:
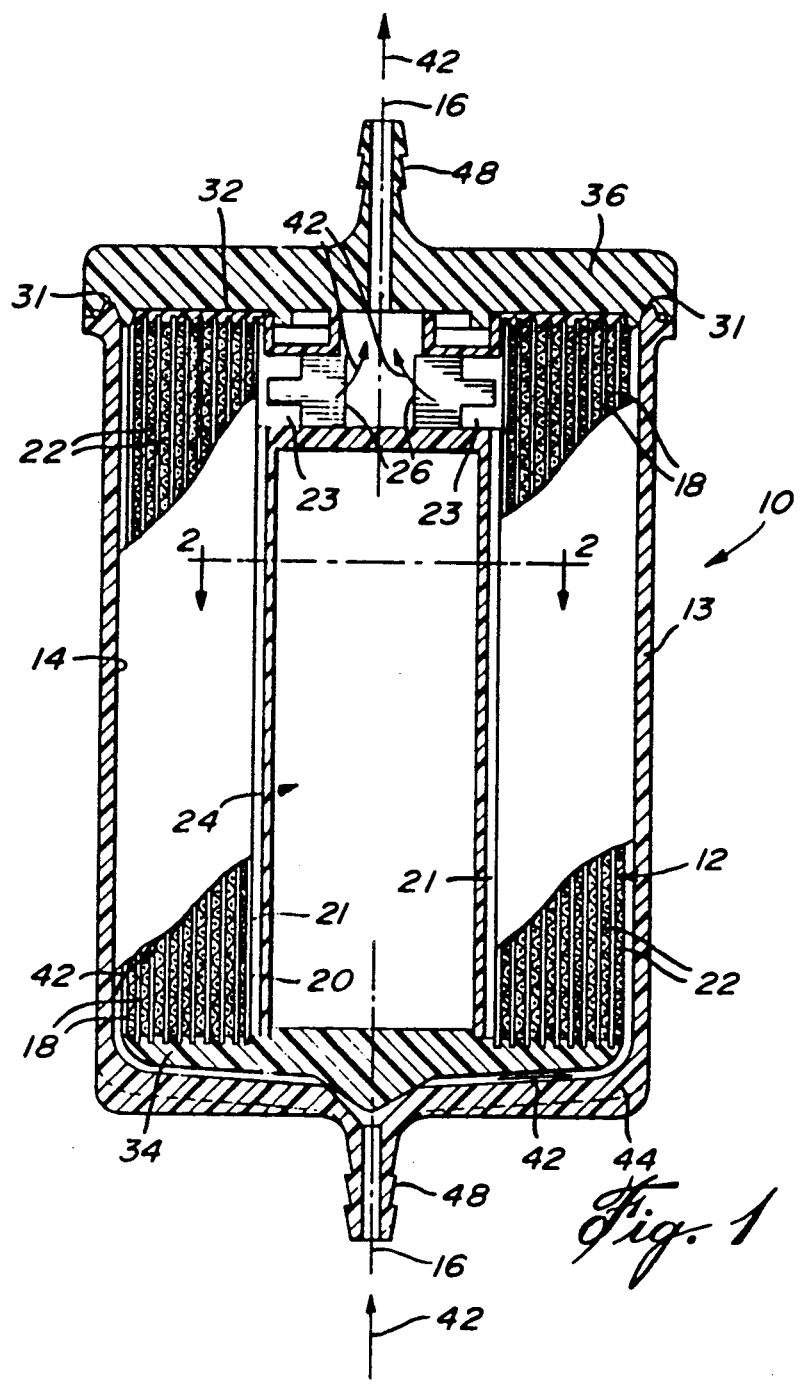
FIG. 1 is a partial sectional view of a side elevation of one embodiment of the chromatography column of this invention.

The present invention is related to the discovery and development of materials useful as insoluble supports for a variety of applications including a wide range of chromatographic separations, including affinity separations, or as insoluble supports for bioreactors.

The support materials are based on a composite of an organic synthetic polymer and a polysaccharide. In a preferred embodiment, the composite per se is biologically inert. The organic synthetic polymer carries chemical groups which are capable of coupling to said polysaccharide, and also carries chemical groups which can provide anchoring capacity for affinity ligands or for biologically active molecules in general.

Strictly speaking, the polymer coupled to the polysaccharide may be either a copolymer or a homopolymer. When the chemical groups capable of coupling to the polysaccharide are the same as the chemical groups useful as anchoring units for affinity ligands or biologically active molecules, the polymer, in this particular form, would be a homopolymer. In another form, however, the polymer is a copolymer containing groups capable of coupling to the polysaccharide and also different groups capable of serving as anchoring groups for molecules. In one preferred embodiment, the polymer is a homopolymer.

The invention also relates to materials derived from the modified polysaccharide by attaching thereto affinity ligands or biomolecules, to thereby obtain affinity chromatography or bioreactive materials, or attaching thereto hydrophobic substituents for reverse-phase chromatography.

The invention also relates to mixtures of the aforementioned materials with unmodified polysaccharides, with modified or unmodified particulate material, or mixtures thereof to give a variety of separation media.

The invention also relates to devices comprising the modified polysaccharide material of the invention which is configured for radial or tangential flow of the sample relative to the support material.

MATERIALS

The term "polysaccharide" as used in the specification and claims is meant to include compounds made up of many--hundreds or even thousands--monosaccharide units per molecule. These units are held together by glycoside linkages. Their molecular weights are normally higher than about 5,000 and can range up to millions of daltons. They are normally naturally occurring polymers, such as, for example, starch, glycogen, cellulose, gum arabic, agar, and chitin. The polysaccharide should have one or more reactive hydroxy groups. It may be straight or branched chain. The most useful of the polysaccharides for the purposes of this invention is cellulose.

The polysaccharide is preferably fully unprotected and carries all of its hydroxy groups in the free state. Some blocking of the hydroxy groups is possible, as for example, by acylation or aminoacylation. Extensive blocking of the hydroxy groups of the polysaccharide, however, is undesirable since the polysaccharide thereby loses its hydrophilic character, which is necessary to provide appropriate chemically compatible interaction with biomolecules. If the polysaccharide becomes too hydrophobic, negative interactions with such molecules as proteins lead to possible nonspecific bonding and denaturation phenomena. Also, if the masking of the polysaccharide hydroxy groups is too extensive, the reactivity of the resulting material with the polymer is greatly diminished. For all of these reasons, it is preferred to retain substantially all hydroxy groups in the free state. The polysaccharide may, however, be chemically activated, as seen infra.

Cellulose is the preferred polysaccharide. By "cellulose" it is intended to mean any of the convenient and commercially available forms of cellulose such as wood pulp, cotton, hemp, ramie, or regenerated forms such as rayon. There exists no criticality as to the selection of a suitable form of cellulose. Cellulose is a naturally occurring polysaccharide consisting of $B(1>4)$ linked glucose units. In the native state, adjacent cellulose chains are extensively hydrogen-bonded, forming microcrystalline regions. These regions are interspersed by amorphous regions with less hydrogen bonding. Limited acid hydrolysis results in preferential loss of the amorphous regions and gives so-called microcrystalline cellulose. The cellulose useful in the present invention is either cellulose in the native state or in the microcrystalline state. Also, cellulose derived from cotton linter is better than that derived from wood pulp, as the latter contains lignin.

Chemical reactions to attach the polymer to the polysaccharide material normally proceed with difficulty in crystalline regions but take place more readily in amorphous regions. For example, the substitution of functional groups into cellulose has a disruptive effect on the structure thereof. If carried out to completion, the cellulose matrix would be destroyed and ultimately water-soluble polymers would be formed. Typical examples of this phenomenon are the hydroxyethyl cellulose and cellulose gums of the prior art, which become the commonly used adhesives and binders after dissolving in water.

Each anhydrous saccharide unit in a polysaccharide molecule may have three or more reactive hydroxy groups. Theoretically, all three or more can be substituted with the polymer. The product from such reaction, however, would have a degree of substitution of three or more, which in case of ion-exchange materials, would render it soluble. Even at levels of substitution below those at which total water solubility occurs, such polysaccharide derivatives become unsuitable as chromatographic supports. Therefore, substitution of the polysaccharide is restricted to the more reactive centers of the amorphous regions and is seldom carried out beyond the level of about 1 mEQ/gm of dry weight in fiber form. At this level of substitution, the native configuration of the polysaccharide structure is only slightly modified, and the low-density, non-uniform exchange sites are readily accessible to large biomolecules.

The final structure of a molecular support of the invention thus comprises a polysaccharide chain covalently modified at a multiplicity of sites along such chain with the synthetic polymers.

The polymer which modifies the polysaccharide is either a homopolymer or a copolymer. The definition of the polymer as a homo-or copolymer depends on whether the polymerizable compounds (a) and (b) are different. In one form, the copolymer could be a random, a block, or an alternating copolymer.

In one embodiment, the polymerizable compound (a) (also called "comonomer (a)" where the polymer is a copolymer) may have a group capable of reacting with a hydroxy group of polysaccharide with the formation of a covalent bond. Such polymerizable compounds are defined, for example, in U.S. Pat. No. 4,070,348 to Kraemer et al., which is herein incorporated by reference. The chemical groups are capable of reacting with hydroxy groups at temperatures up to those at which the polysaccharide begins to decompose or depolymerize, e.g., 0° to 120° C., in aqueous solution and thereby form covalent bonds with the oxygen atoms of the hydroxy groups. Since water is always present in considerable excess with respect to the hydroxy groups, chemical groups which react spontaneously with water, such as, for example, isocyanate groups, are less suitable. Aqueous solutions comprise pure water or mixtures of water with one or more water-miscible co-solvents such as alcohols, ketones, and the like.

Hydroxy reactive groups of comonomer (a) are preferably activated carboxy groups such as are known from peptide chemistry or O-alkylating agents, such as alkyl halide or epoxide groups. Representatives of the O-alkylating comonomers are acrylic and methacrylic anhydrides, acrylolylmethacrylol N-hydroxy succinimides, ω-iodo-alkyl esters of acrylic or methacrylic acid in which the alkyl group in general contains two to six carbon atoms, allyl chloride, chloromethylstyrene, chloroacetoxy ethyl methacrylate, and compounds having a glycidyl group. The latter are ethers or esters formed between a glycidyl alcohol and an unsaturated alcohol or unsaturated carboxylic acid, respectively. The glycidyl alcohols are aliphatic and cycloaliphatic alcohols and ether alcohols having from 3 to 18 carbon atoms which are esterified with an α, β-unsaturated carboxylic acid, preferably acrylic or methacrylic acid, or are etherified with an olefinically or acetylenically unsaturated alcohol. Typical compounds are glycidyl acrylate and methacrylate; 4,5-epoxy-pentylacrylate; 4-(2,3-epoxy-propyl)-N-butyl-methacrylate; 9,10-epoxy-stearylacrylate; 4-(2,3-epoxypropyl)-cyclohexyl methyacrylate; ethylene glycol-monoglycidyl etheracrylate; and allyl glycidyl ether.

Preferred organic synthetic polymers include the homopolymers of glycidyl acrylate and glycidyl methacrylate.

If the active monomer units (a) are sensitive to hydroxy groups, and if they do not react with the polysaccharide offered, they may be transformed, in the presence of water, into hydrophilic carboxy, aldehyde, or hydroxy groups. The activated groups are therefore present in the polymeric material in generally greater number than is necessary for the bonding with the polysaccharide.

In another embodiment, the polymerizable compound (a) may be one which does not react directly with hydroxy groups of the polysaccharide, but rather is covalently coupled to the polysaccharide indirectly, via a bridge compound. This is the case when the polysaccharide is first chemically activated as by oxidation and reacted with a compound having, e.g., an epoxy group or a vinyl group capable of reaction with an appropriate functionality of polymerizable comonomer (a).

The polymerizable comonomer (b), where (b) is different than (a), will vary depending on the ultimate use of the carrier material. When the ultimate use of the carrier material is as a support for an affinity ligand, comonomer (b) carries a chemical group capable of causing the covalent coupling of said comonomer (b) to an affinity ligand, i.e., an "anchoring" group. Since most affinity ligands carry nucleophiles such as hydroxy, amino, thiol, carboxylate, and the like, any electrophilic group capable of reacting with such nucleophile can be present in comonomer (b). Such electrophilic groups include, but are not limited to, those described previously as active groups capable of reacting with the hydroxy group of cellulose. They also include activated carboxy groups used in peptide chemistry for the formation of peptide bonds, such as carbonyl chlorides, carboxylic anhydrides, and carboxylic acid azide groups, as well as phenyl esters and aldehydes used for the formation of Schiff (imine) bases.

Also useful are the carboxylates of hydroxylamino derivatives of the formula (1)

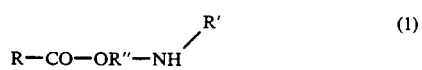

in which R is an α, β-unsaturated, polymerizable radical and R' is a $C_1-C_6$ alkyl or alkanoyl group, phenyl, or hydroxyphenyl. R" may be a direct bone (—) or a $C_2-C_3$ alkyl or alkanoyl group. Typical compounds of this type are:

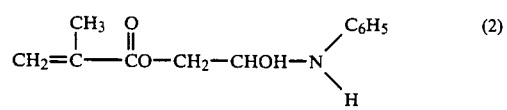

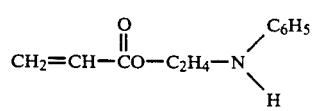

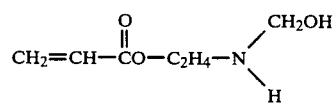

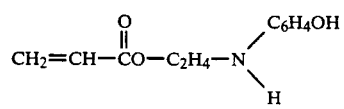

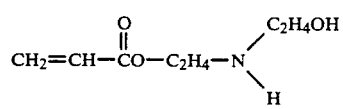

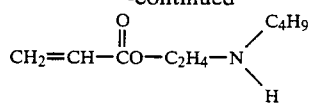

Other compounds having activated carboxyl groups include acryloyl and methacryloyl chloride, acrylic and methacrylic anhydride, maleic anhydride, phenyl acrylate and methacrylate, glycidyl acrylate and methacrylate, 4-iodobutylacrylate and methacrylate, and 2-isopropenyl-4, 4-dimethyloxazolone-5. The last mentioned compound is capable of reacting with the terminal amino group of proteins, either directly or through conversion.

A very useful potentially electrophilic reactive group in comonomer (b) useful for coupling to an affinity ligand is a group capable of being activated to an electrophilic group with a reagent such as a cyanogen halide. It is known in the art that cyanogen halides react with 1,2-diols to yield activated structures having the following formula (3):

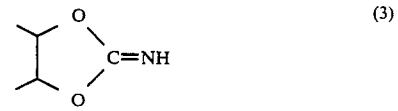

This structure is then capable of reacting with the nucleophile of an affinity ligand. Among the preferred 1,2-diols present in comonomer (b) are various saccharides, including monosaccharides such as glucose, mannose, and galactose; disaccharides such as lactose and maltose; trisaccharides such as raffinose; or, generally, glycosides. The 1,2-diol-containing functional group can be attached to the polymerizable comonomer (b) by such reactions as esterification, amide formation, etherification, and the like. Among the most preferred of these is the reaction of glycidyl acrylate or methacrylate with a saccharide, to yield an ether-containing comonomer (b).

When the ultimate use of the carrier material is as a carrier for biological molecules, any of the anchoring groups mentioned for comonomers (a) or (b) can also be used. Other types of activated groups such as those containing aldehydes or amines can also be used.

The polymerizable comonomer (b) can be substantially of one type or can be a mixture of one or more types.

Preferably, the polymerizable monounsaturated compounds (b) are polymerizable compounds of the formula (4):

wherein $R^1$ is hydrogen or methyl; A is CO, or $SO_2$; X is OH, OM (where M is a metal ion), or $OR^2$ (where $R^2$ is a straight or branched chain $C_1-C_{18}$ alkyl group), $OR^3OH$ (where $R^3$ is a straight or branched chain $C_2-C_6$, alkyl, or aromatic group), $ONR^4R^5$ or $ON+R^4R^5R^6$, where $R^4$ is the same or different as $R^5$ which is the same or different as $R^6$, and are hydrogen, $R^2$, or $R^3OH$);

AX may also have formula (5):

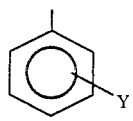
(5)

wherein Y is $-CO_2^-$, $-CH_2CO_2^-$, $-SO_3^-$, $-CH_2SO_3^-$, $-OPO_3H^-$, $-CH_2PO_4H^-$, $-CH_2N(CH_2COO^-)_2$, $-CH_2-NR^4R^5$, or $-CH_2-N^+R^4R^5R^6$, or the corresponding free acid, ester or partial ester groups, as described previously. In these formulae, the groups $R^4$, $R^5$; $R^4$, $R^6$; or $R^5$, $R^6$ may form a five-to seven-membered heterocyclic ring with the nitrogen atom. $R^4$, $R^5$, and $R^6$ are as previously defined.

When the material is to be used as an anchor for affinity ligands or biomolecules, A is CO or $SO_2$, and X is most preferably $O-CH_2-CH(OH)-CH_2-$Saccharide, where "—Saccharide" is a mono-, di-, or polysaccharide having a group which can be activated for reaction with nucleophilic reactive groups on the affinity ligand or the biomolecule by a cyanogen halide. A more preferred comonomer (b) for anchoring materials is the comonomer obtained from reaction of glycidyl acrylate or methacrylate with glucose.

The average molecular weight of the polysaccharide-modifying polymer is a function of the monomeric mix present therein. It is required to have at least a sufficient number of comonomers (a) units so as to be able to form covalent attachment throughout amorphous regions of the polysaccharide surface. The number of comonomers (b) units cannot be too small, since otherwise the exchange capacity, or the anchoring/interacting capacity, is negligible. The number of comonomers (b) units can neither be too high, since this would cause great difficulty in the reaction between the reactive groups of comonomer (a) and the polysaccharide. Preferably, the polysaccharide-modifying copolymer carries anywhere between 1 and 500 units of comonomer (a) and most preferably between 20 and 100 units of comonomer (b). This corresponds to molecular weights of between about 100 and 100,000, preferably between 1,000 and 10,000.

Other neutral comonomers (c), different than those represented by (a) or (b), supra, can also be added to the polymer, if desired. These comonomers may be polymerizable unsaturated compounds carrying neutral chemical groups such as hydroxy groups, amide groups, alkyl groups, aryl groups, and the like. Preferred among comonomers (c) are $C_1-C_6$ alkyl acrylates or methacrylates, or the corresponding hydroxy alkyl acrylates or alkacrylates. The function of comonomers (c) may be to increase the presence of hydrophobic or hydrophilic residues in the polymers, so as to provide a desired balance of hydrophilic and hydrophobic groups, if necessary.

The minimum ratio of comonomer (a) to total comonomer content is important. The synthetic polymer should have a sufficient amount of comonomer (a) to permit substantial covalent coupling of the polymer to the polysaccharide. If too little comonomer (a) is present in the polymer, then grafting becomes difficult, if not impossible. Generally, about 4–12, preferably 5–10% by weight of comonomer (a) relative to the total of (a) plus (b) and (c) (if any is present) is needed. Amounts of about 0.5 to 1 or 2% by weight appear to merely cross-link the polymer, without substantial grafting onto the polysaccharide.

The upper limit of comonomer (a) in the polymer can be varied up to 99.9% by weight, depending on the desired amount of rigidity, functionality and hydrophilicity. It is preferred to have a predominance of comonomers (b) over comonomers (a). Comonomers (c) may be present in an amount of up to 20% by weight of the total (a) plus (b) plus (c).

The weight ratio of polysaccharide to the modifying polymer is freely adjustable and varies from 0.1 to 5 weight parts of copolymer to parts by weight of the polysaccharide.

When comonomers (b) carry ionizable chemical groups capable of providing cation-exchange capacity, it is found that unless some degree of crosslinking is provided, the flexibility of the material in solution tends to favor the formation of micelle-type aggregates and slow loss of capacity. Therefore, it is a preferred mode of the invention to provide polymeric crosslinking for these types of modified polysaccharides. Crosslinking can be provided either by incorporating into the polymerization recipe a small amount of polyunsaturated comonomer having at least two polymerizable α, β-carbon double bonds, such as for example mono- and polyethylene glycol dimethacrylates and diacrylates (with the polyethylene glycol residue containing up to six ethylene groups), ethylene dimethacrylate, ethylene diacrylate, tetramethylene dimethacrylate, tetraethylene diacrylate, divinylbenzene, triallyl cyanurate, methylene-bis-acrylamide or -bis-methacrylamide, and the like.

Another type of crosslinking agent is particularly applicable to copolymers made from an aminoalkyl comonomer (b). Because of the presence of a free pair of electrons on the aminoalkyl nitrogen atoms, crosslinking can be carried out with such bifunctional reagents as would react with nitrogen free electron pairs. Among these are the diacyl halides, such as $Hal-CO-(CH_2)_n-CO-Hal$, or the alkyl diahalides, such as $Hal-(CH_2)_n-Hal$, wherein Hal is a halide such as chloride, bromide, or iodide, and n may be anywhere between 2 and 12. Other bifunctional reagents capable of reaction with nitrogen atoms can also be used. The advantage of these bifunctional reagents is that they simultaneously cross-link the copolymer, while also providing a cationic charge at the nitrogen centers, thereby ionizing the material.

The amount of cross-linking agent is best determined empirically. It is to be considered sufficient when the polymer preserves the exchange capacity at a constant value over time, yet would be too high if swelling is prevented, and too much rigidity is obtained in the final materials. Ideally, an amount of cross-linking agent between 5 to 20 mole percent of the synthetic polymer units is sufficient.

The term "affinity ligand" as used throughout the present application and in the claims is meant to include any small or high molecular weight molecule which can be immobilized in a stationary phase and used to purify a complementary binding molecule from a solute phase by affinity chromatography. For example, a ligand can be an inhibitor, a cofactor, a prosthetic group, or a polymeric substrate, all of these useful to purify enzymes or holoenzymes. Other ligand/ligate pairs are enzyme/polymeric inhibitors; nucleic acid, single-strand/nucleic acid, complementary strand; hapten or antigen/ antibody; antibody/proteins or polysaccharides; monosaccharides or polysaccharides/lectins or receptors; lectins/glycoproteins or receptors; small target compounds/binding proteins; and binding protein/small target compounds. When antigen/antibody pairs are used as the ligand/ligate pair, the technique takes the particular name of "immunoaffinity" chromatography.

The "biologically active molecule" which can be bound to the carriers of the invention can include enzymes, enzyme substrates, hibitors, hormones, antibiotics, antibodies, antigens, peptides, saccharides, nucleic acids, and the like. The only requirement for these molecules is that they have reactive groups thereon which can be covalently coupled to the anchoring chemical groups on the synthetic polymer.

Of particular interest is the immobilization of enzymes such as hydrolases, isomerases, proteases, amylases, and the like. These immobilized enzymes can then be used in biochemical reactors, as is otherwise well known in the art.

The use of the term reverse-phase chromatography or "hydrophobic interaction chromatography" is meant to include chromatography used to absorb hydrophobic components in mixtures. Such components include lipids, cell fragments and the like. In this embodiment, comonomer (b)(2) is usually an acrylate or methacrylate ester of $C_6$–$C_{18}$ straight or branched chain alcohols, or of aromatic alcohols such as phenol or naphthol.

The carrier materials of the present invention can be used per se in the same manner as other polysaccharide-based carrier materials of the prior art. Alternatively, and in a preferred mode, the polysaccharide material, which is preferably in fibrous form after the modification, can be formed into a self-supporting fibrous matrix, such as a fibrous sheet, with affinity chromatography properties, bioreactive or reverse-phase properties. The modified fibrous polysaccharide fibrous media can also incorporate unmodified fibers of various different sizes, and, in addition, can also incorporate modified or unmodified particulate material.

The fibrous media comprises a porous matrix of fiber wherein, because of the nature of the present invention, the fiber is effective for molecule reactions. The matrix is substantially homogeneous with respect to each component. A particulate may, optionally, be present. When such a particulate is present, is preferred to modify it so that it is also effective for molecular separations or reactions. Such a particulate should be contained in the fibrous phase in an effective amount to achieve the desired separations or reactions. The overall media is substantially inert and dimensionally stable.

The preferred particulates which can be used include all of those substances which can be provided in finely divided form and exhibit chromatographic functionality, i.e., capable of effective molecular separations and/or reactions. Mixtures of such compositions may also be utilized. Exemplary of such particulates are silica, alumina, zirconium oxide, diatomaceous earth, perlite, clays such as vermiculite, carbon such as activated carbon, modified polymer particulates such as other ion-exchange resins, crystalline cellulose, molecular sieves, and the like, the surfaces of which may be modified in a conventional manner. Such materials are commercially available under a variety of trademarks such as Biosila, Hi-Flosil, Li Chroprep Si, Micropak Si, Nucleosil, Partisil, Porasil, Spherosil, Zorbax cil, Corasil, Pallosil, Zipax, Bondapak, LiChrosorb, Hypersil, Zorbax, Perisorb, Fractosil, Corning Porous Glass, Dowex, Amberlite resins, and the like.

Examples of references which describe particulate effective for molecular separations are Miller. U.S. Pat. No. 3,669,841, Kirkland et al., U.S. Pat. No. 3,722,181, Kirkland et al., U.S. Pat. No. 3,795,313, Regnier, U.S. Pat. No. 3,983,299, Chano. U.S. Pat. No. 4,029,583, Stehl. U.S. Pat. No. 3,664,967, Krekeler. U.S. Pat. No. 4,053,565 and Iher. U.S. Pat. No. 4,105,426. The entire disclosures of all of these references are incorporated by reference.

The particle size of the particulate is not critical but influences somewhat the flow rate at which the sample to be treated passes through the material. For radial flow applications, uniform particle sizes greater than about 5 microns are preferred, with about 10–100 microns constituting a practical operational range. Somewhat smaller particle sizes are possible for tangential flow applications where the sample flows across, and not through, the matrix material. The amount of the particulate can vary widely up to about 80 wt. % or more of the solid phase. The optimum particulate concentration will vary depending on the molecular separation desired.

The fibrous media should be capable of immobilizing the particulate contained therein, i.e., capable of preventing significant particulate loss from the stationary phase. In the case of media configured for radial flow, the media should have a porosity which enables the fluid to passthrough the media. Thus, although the modified cellulose materials of the present invention are self-bonding and the addition of extra fibers or binders may not be necessary, it is possible to utilize such extra fibers or binders. Other fibers usable for the media include polyacrylonitrile fibers, nylon fibers, wool fibers, rayon fibers and polyvinyl chloride fibers, other cellulose fibers such as wood pulp and cotton, and cellulose acetate.

One embodiment of the invention is the provision of a fibrous media comprising two different types of celluloses: one a modified cellulose according to the invention and another an unmodified cellulose.

Another embodiment of the invention, which may also be coupled with the aforementioned celluloses, is an unrefined structural fiber which assists in providing sheets of sufficient structural integrity in both the wet "as formed" condition, and in the final dry condition, and also allows handling during processing as well as suitability for the intended end use. Such fibers are typically relatively large, with commercially available diameters in the range of 6 to 60 micrometers. Wood pulp can also be used and has fiber diameters ranging from 15 to 25 $\mu$m, and fiber lengths of about 0.85 to about 6.5 mm. The unrefined self-bonding structural fibers typically have a Canadian Standard Freeness of +400 to +800 ml. These long self-bonding fibers may constitute greater than 50% of the fibrous media, by weight, preferably 60–100% of the fibrous media, and most preferably 100%. Optionally, a minor portion of cellulose pulp which has been refined to a Canadian Standard Freeness of between +100 and −600 ml may be incorporated with a major portion of the normally dimensioned cellulose pulp (+400 to +800 ml). In particular, from about 1 to about 20% of the refined pump and about 50% to about 90% of the unrefined cellulose may be contained in the matrix. Particulate may also be added.

When the particulate materials are millimicron-sized, it may be desirable to use, in addition, a mixture of cationic and anionic resins as described by assignee's U.S. Pat. No. 4,488,969. Alternatively, one may use a medium containing, in addition to the milli-micron-sized particles, a neutral organic polymeric resin having oxygen atoms along the polymeric backbone thereof, as described in the assignee's U.S. Pat. Nos. 4,578,150 and 4,596,660.

Also of particular interest in the present invention is the use of modified cellulosic fibrous media carrying modified inorganic support materials, such as for example are described in Regnier. U.S. Pat. No. 3,983,299, Kirkland et al., U.S. Pat. No. 3,795,313, Kirkland et al., U.S. Pat. No. 3,722,181, Mazarouil et al., U.S. Pat. No. 4,034,139, Talley et al., U.S. Pat. No. 4,118,316, Ho Chang et al., U.S. Pat. No. 4,029,583 or Reonier. U.S. Pat. No. 4,108,603. These are all incorporated herein by reference. In particular, it is possible to derivatize siliceous particles with silanes and attach thereto various ion-exchange or anchoring groups. In this embodiment then, both the cellulosic fiber and the siliceous particulate are modified, and their interaction provides increased anchoring and/or ion-exchange capacity. The addition of particulate material tends to increase the rigidity and strength of the fibrous media and renders it readily useful for industrial applications, especially those involving high pressure.

PROCESSES OF PREPARATION

The polymer-modified polysaccharide material of the invention can be prepared in various modes. Generally speaking, in one mode, one can first prepare the polymer and then condense the same through its hydroxy reacting groups (if available) to the polysaccharide. Alternatively, in another mode, one can first react the polysaccharide with a hydroxy group-reactive comonomer (a) followed by copolymerization with comonomer (b) and any other comonomers (e.g., crosslinking comonomers, hydrophobic comonomers, etc.), as desired. These reactions are therefore of two types: 1) coupling of saccharides to hydroxy reactive groups on comonomer (a), and 2) polymerization of polymerizable unsaturated compounds. In a preferred embodiment, with the intention of providing high capacity adsorptive functionality, the reaction is conducted under conditions wherein polymerization proceeds prior to covalent coupling.

Still a third method of (indirectly) attaching the synthetic polymer to the polysaccharide involves previous chemical activation of the polysaccharide. For example, the polysaccharide can be treated with oxidizing agents such as periodate, hydrogen peroxide, ceric or other metallic oxidizing ions or the like. Reaction of the activated polysaccharide with an amino-containing polymerizable monomeric compound followed by reduction, or an epoxy-containing vinyl monomer, will normally yield derivatized polysaccharide carrying unsaturated functionalities along the chain thereof. These unsaturated functionalities can then serve as further attachment positions for conjugating the polymer thereto.

Another type of chemical activation of the polysaccharide involves reaction with a compound such as a diepoxide or epichlorohydrin, which yields a derivatized polysaccharide-carrying epoxy or other groups along the chain thereof. These epoxy or other groups then serve as conjugating positions on the polysaccharide chains.

Polymerization of comonomers can be carried out by radical chain (free radical), step-reaction, ionic and coordination polymerization. Particularly useful is free radical polymerization.

The free radical addition polymerization of radical polymerizable comonomers is carried out with free radical initiators using well known steps of initiation, addition and termination. A usual procedure is to utilize a substance or substances which produce radicals capable of reacting with the monomers. Probably the simplest of all polymerization initiators are the organic peroxides and azo compounds. These substances decompose spontaneously into free radicals in common organic solvents at a finite rate, at temperatures between 50° and 140° C. For example, benzoyl peroxide decomposes into two benzoyloxy radicals at 60° C. Another example is afforded by the azo compound azo-bis-isobutyronitrile which similarly decomposes into radicals at easily accessible temperatures.

The necessary energy may also be provided by irradiating the initiator system with ultraviolet light. For example, initiation can be provided by irradiating the initiator system in the presence of photo initiators such as benzophenone and its derivatives, benzoin alkyl ethers or derivatives, or acetophenone, with ultraviolet light. It is then necessary that the initiator molecules absorb in the spectral region supplied. In this way radicals can be generated at a finite rate at considerably lower temperatures than are necessary if purely thermal excitation is used. Finally, bimolecular reactions may produce radicals capable of initiating polymerization. Particularly important are the redox reactions, which occur in aqueous media, and involve electron transfer processes. For example, the systems Fe(II) plus hydrogen peroxide, or Ag(I), plus $S_2O_8^-$ are particularly important in initiating the radical polymerization of monomers. Because of the low temperature of initiation, the redox initiators or photochemically induced initiators are particularly preferred in the present invention. The amount of initiator is that sufficient to initiate the polymerization reaction. Polymerization is carried out until substantially all of the monomers or comonomers have been incorporated into the polymeric chains. This can be readily ascertained by simple analytical tests on the reaction mixture. Preferably, this polymerization is accomplished almost simultaneously with or immediately prior to the covalent coupling of the polymer to the polysaccharide. Preferably, the coupling and polymerization are performed in the same aqueous phase.

In one embodiment, the condensation of the monomer (or comonomer (a)) with the hydroxy group or groups of polysaccharide, whether carried out before polymerization or thereafter, is normally carried out by adjusting the temperature of the reaction mixture, or by adding an appropriate acid/base catalyst.

The most preferred method of carrying out the process is in a "one-pot" system, using a hydroxy reactive monomer (or comonomer (a)). All desired monomers and polysaccharide are added to an inert solvent system, such as, e.g., water, alcohols, organics, and the like. The polysaccharide and monomers are treated under conditions which will initiate polymerization of the monomers. This can be accomplished, for example, by adding to a well stirred mixture a water solution of an initiator such as ammonium persulfate and sodium thiosulfate, and initiating polymerization from about 15°

C. to 40° C. Alternatively, a photolabile initiator can be added and initiation caused by photochemical means. After stirring for a time sufficient to allow the polymerization to proceed to completion, the linking of the formed polymer to the hydroxy groups of polysaccharide is caused by increasing the temperature of the reaction mixture to a temperature sufficient to cause this condensation. In the case when the linking group on the polymer is glycidyl group, such temperature is normally around 80°–100° C. Reaction is then allowed to proceed at the second temperature for a time sufficient to either go to completion, or to achieve modficiation of the polysaccharide to the desired capacity. The product is filtered, washed and dried for further treatment, if necessary. Unreacted monomer is preferably washed away with alcohol, unreacted catalyst with aqueous media and polymer with methanol or ethanol. Further reaction of the modified polysaccharide may be by crosslinking.

Another further reaction of the modified polysaccharide materials would be to anchor the affinity ligands or biologically active molecules to the anchoring groups of the monomer (or comonomer (b)). This reaction can be readily accomplished by mixing in an appropriate solvent, normally aqueous, the affinity ligand or biomolecule to be anchored and the modified polysaccharide, and carrying out anchoring for a time and under conditions sufficient to cause covalent coupling therebetween. It may be necessary to activate polysaccharide groups on the monomer (or comonomer (b)) with such materials as cyanogen halides, and to then further treat the activated polysaccharides with the affinity ligands or biomolecules. In this embodiment, it is preferred to first couple the affinity ligand or biologically active molecule to the monomer (or comonomer units (b)), and then bind the resulting polymer or copolymer to the polysaccharide.

The reactions between the affinity ligand or biologically active molecule and the anchoring groups of the polymer are normally carried out at temperatures of from 0° C. to 50° C., may involve the addition of catalysts such as acid or base, or metals, or such other materials as carbo di-imide, or a bi-functional cross-linker such as glutaraldehyde. The resulting ligand- or biomolecule-containing modified polysaccharide is washed under appropriate conditions and is ready for further treatment, if necessary.

The affinity matrix is produced by grafting a polymeric carrier onto a substrate and then coupling an affinity ligand to the grafted, covalently bound synthetic polymer. This pre-coupled structure is referred to below as the pre-ligand structure. Suitable substrates include the substrates mentioned above, i.e. polysaccharides such as cellulose. Again, cellulose is the preferred substrate material for use.

The polymer which is grafted to the substrate may contain functional groups which act as precursor groups for various types of functional groups such as amine and thio. This type of modification provides a means for subsequent derivatization to meet specific needs. Typical monomers include ethylenically unsaturated oxirane-containing monomers such as glycidyl acrylate and methacrylate, ethylenically unsaturated hydroxy-containing monomers such as hydroxyethylmethacrylate, and ethylenically unsaturated amide group-containing monomers such as acrylamide. Glycidyl methacrylate (GMA) and glycidyl acrylate (GA) are the preferred grafting monomers.

In order to prepare a satisfactory affinity matrix, especially when used in a radial-flow device, it is important to control the pore size of the grafted polymer so that, even after ligand coupling there will be sufficient space left for the molecules to freely penetrate for ligand binding. However, requirements for such large pore size frequently cause mechanical stability problems. Currently available commercial products sold as affinity matrices rely on a carefully controlled degree of crosslinking to provide structural rigidity. However, these lightly crosslinked materials are extremely fragile, and frequently degrade under even conventional mixing techniques. While increased physical stability may be achieved by increasing the crosslinking, the increased linking decreases the porosity of the material.

In one embodiment of the present invention, this problem of balancing the requirements of structural rigidity and porosity is accomplished with a two step interpenetrating network wherein cellulose or some other natural polymer provides a three-dimensional skeleton within and around which a second network of acrylic polymer is formed. The cellulosic or other natural polymer substrate provides the necessary rigidity, permitting the acrylic polymer to be only lightly crosslinked, this lightly crosslinked polymer possessing the required chemical and porosity properties. Under polymerization conditions similar to those of Examples 3 and 4, crosslinking occurs.

The synthetic polymer may be formed utilizing any of the polymerization techniques conventional in the art. Suspension polymerization is a preferred polymerization technique, the monomer suspended and maintained by continuous stirring of the reaction mixture, optionally with the use of surfactants. A free radical initiator is employed which dissolves in the monomer phase and polymerization is achieved by a thermal fragmentation of the catalyst. Prior to completion of the polymerization, reaction conditions are altered to facilitate the coupling reaction whereby the polymerization product hydrocarbon chains, with attendant functional groups attached, are then grafted to the natural polymer substrate. During this latter phase of the polymerization, both polymerization and coupling proceeds simultaneously.

GMA grafted to cellulose represents one preferred affinity matrix. GMA provides three functions, the oxirane groups of the GMA monomer providing covalent coupling with the surface hydroxy groups of the cellulose, these same oxirane groups providing crosslinking capability for the synthetic polymer network, and the remaining oxirane groups serving for subsequent ligand coupling.

The following is a description of the physical and chemical characteristics of the GMA-cellulose affinity matrix:

1. Mechanical Rigidity—Cellulose fibers provide good structural strength as a solid support member. These fibers are further strengthened by the strong hydrogen bonding force between the polysaccharide units of the cellulosic fibers, additional strength provided by the highly crystalline structure. Additional mechanical rigidity is provided by crosslinking which occurs between the cellulose and the synthetic polymer.

2. Macroporosity—Careful selection of fiber diameter, length, degree of fiberization and degree of crosslinking provides for a high degree of control of macroporosity.

3. Hydrophilicity—The hydroxyl groups in the cellulosic structure provide for a high degree of hydrophilicity. Further, oxidation of the glycidyl groups of the GMA polymer to diols or copolymerization of the latter with a hydroxyl-containing monomer further add to the hydrophilic character of the matrix.
4. Chemical Resistivity—Cellulose has a low solubility in conventional solvents; further, solvent resistance is provided by crosslinking the glycidyl groups of the GMA polymer with each other and with the hydroxy groups of the cellulose.
5. Structural Integrity—Swelling and shrinking of the matrix is negligibly small due to the grafted crosslinkable monomer, further stability being provided by additional crosslinking with a bifunctional monomer.
6. Low Non-Specific Adsorption—The grafting process further purifies the cellulosic raw materials, decreasing the number of available sites for non-specific binding.
7. Chemical Reactivity—As much as a 200% weight gain after granting results in the production of a high number of oxirane groups for ligand coupling. Further, these ligand groups may be spaced apart with a "spacer arm" if necessary. An excellent flow characteristic—the high degree of control provided with regard to structure and porosity—results in excellent flow-through properties. Additionally, this matrix may be completely dried between uses, thereby enhancing its flow characteristics.

The cellulose-GMA affinity matrix may be chemically modified as set out in Table I below. The purpose of this chemical modification is to prepare the matrix or preligand structure for coupling with the ligand.

Suitable oxidizing agents for (1) above of Table I include perchlorate, sulfur trioxide, and periodate, with periodate preferred.

Suitable aminating agents under (2) above of Table I include compounds having the structural formula $NH_2—R—NH_2$ wherein R is a direct bond or $(CH_2)_n$.

Thiolation may be effected by using compounds such as NaSH or KSH. Table II below briefly summarizes oxidation, amination, and thiolation reactions.

TABLE II

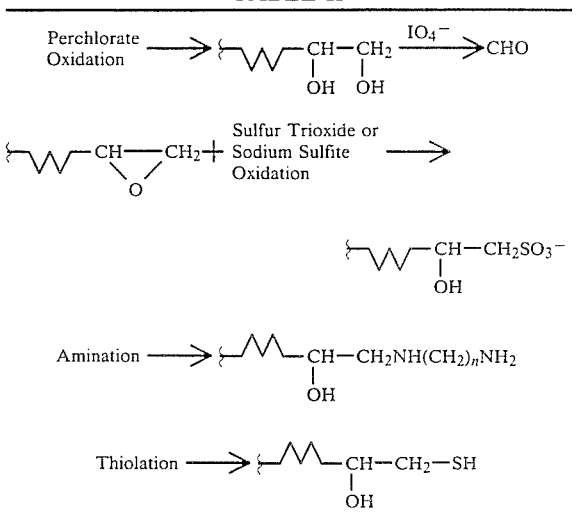

TABLE I

| Basic Affinity Matrix | Method of Conversion | Functional Groups* in Converted Matrix |
|---|---|---|
| A. Cellulose GMA matrix 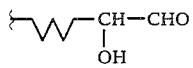 | 1. Oxidation | 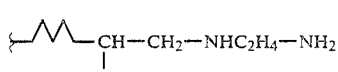 |
| | 2. Amination |  |
| | 3. Thiol formation |  |
| | 4. Chelate formation | 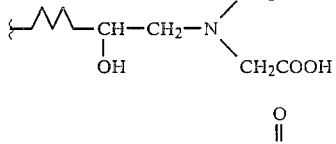 |
| | 5. p-Benzoquinone coupling | 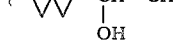 |
| | 6. Dye ligand (cibcron blue) | ⸻NH-Dye |

*In this table and the following structures,  represents the substrate such as celluloe and the covalently attached moiety.

TABLE II-continued

The aldehyde reaction product resulting from periodate oxidation as demonstrated at Table II above may be further treated to form a boronate affinity absorbent according to the following equation:

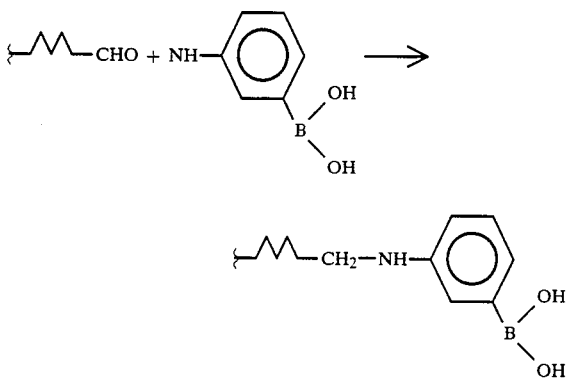

Amination with a diamine such as hydrazine proceeds according to the following equation, resulting in the formation of a substituted hydrazine.

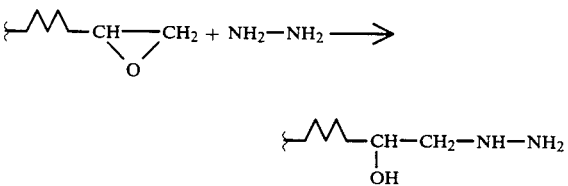

The substituted hydrazine may be converted to the azide form according to the following equation:

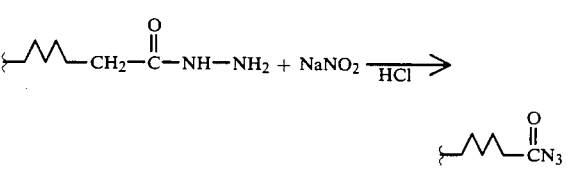

The azide may be converted to an appropriate affinity matrix by reaction with an appropriate ligane, for example, lysine, in accordance with the following equations:

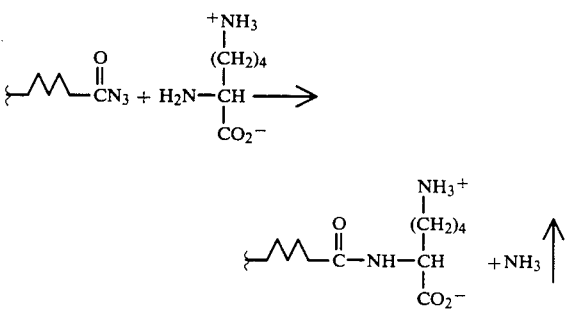

-continued

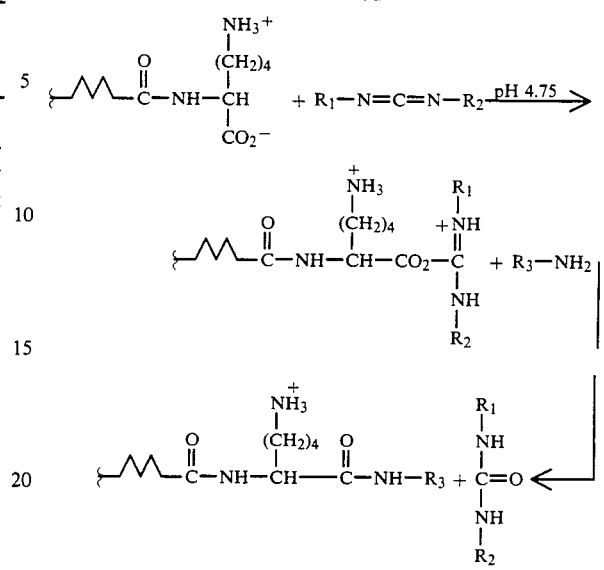

where $R_1$ and $R_2$ are $C_1$-$C_4$ alkyl.

As shown in Tables I and II above, the GMA-cellulose matrix may be thiolated with NaSH. The thiol group may then be subsequently activated by reaction with 2,2'-dipyrridine disulfide according to the following equation:

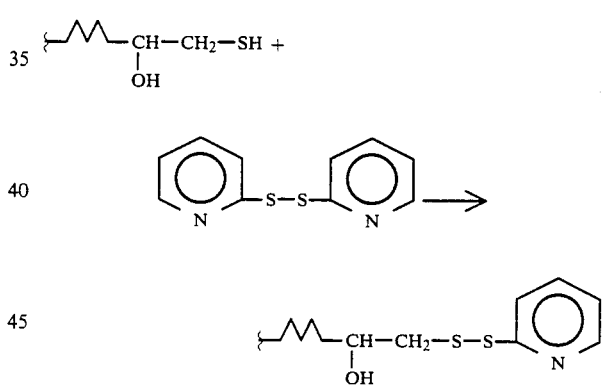

This substrate will react with sterically accessible-SH groups of protein according to the following equation:

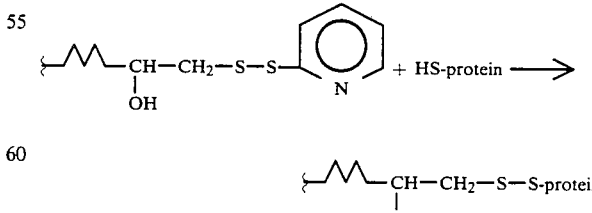

In like manner, substrates may be modified to provide an amide functional group, the amide functional group further reacted with a diamine according to the formula:

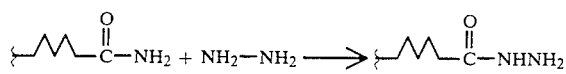

The resulting hydrazine may be subsequently treated as with the above amination of the oxirane ring.

Synthetic polymer-modified substrate with reactive hydroxyl groups may be produced utilizing compounds such as hydroxyl ethyl-methacrylate (HEMA) or hydroxyl propylmethacrylate (HPMA) onto an appropriate substrate such as cellulose. Adjacent hydroxyl groups may be activated utilizing CNBr according to the following equation:

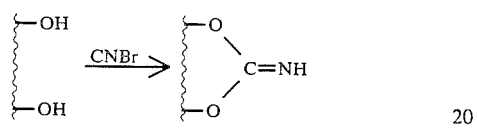

The starting point for designing an affinity matrix for removal of specific enzymes is to examine the structure of the enzyme and, particularly, the structure of the inhibitors of the enzymes. The complex formed between an enzyme and its inhibitor provides the best picture of how the enzyme may interact with the specific protein structure. Enzyme inhibition is always competitive and reversible as expressed by the following equation:

E(enzyme)+I(inhibitor)=EI complex

Normally, the reactive site residue of the inhibitor fits into the pocket of the enzyme. In the case of kallikrein and trypsin, it is the lysine or arginine residue which interacts with the nucleophilic hydroxyl groups of kallikrein's serine active sites. In many cases, an animal enzyme inhibitor may be extracted from plants. An effective affinity matrix may thus be made by binding the plant inhibitors for enzyme adsorption. It is known that plasma kallikrein inhibitors have been isolated from potatoes and peanuts. The resulting substrate product may be further reacted with the amine functionality of a protein to provide an appropriate affinity adsorbent according to the following equation:

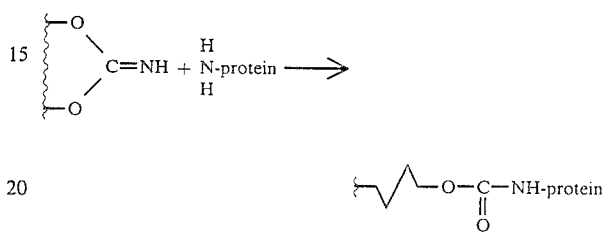

Additionally, by utilizing the glycidyl group as a precursor, it is possible to couple another moiety through the glycidyl group. The newly linked moiety may be activated with a different activation mechanism for protein coupling as shown below in Table III.

TABLE III

| Original Functional Group | New Moiety Converted | Protein Binding Mechanism |
|---|---|---|
|  | Sugar (either in mono, di or trisaccharide form) | All the Sephadex ® or Sepharose ® coupling method can be applied with more flexibility |
| | Chelating | Through metallic ions |
| | Lectin (such as Con A) | Those carbohydrate binding plant seeds have specific affinity for glycoproteins |
| | Polylysine, polyarginine or other poly amino acids | Proteolytic enzyme binding |
| | Protein A | IgG binding on Fc region |
| | Polyphenol | Discussed below |

Coupling Through Polyphenol

Proteins are highly reactive toward polyphenols. The basic reaction is the addition of any nucleophilic residue on the proteins to the quinone form of the polyphenol through the following route:

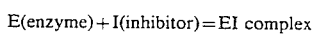

Method 1

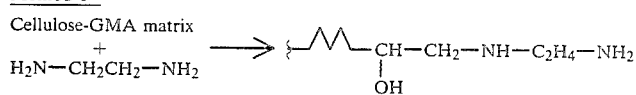

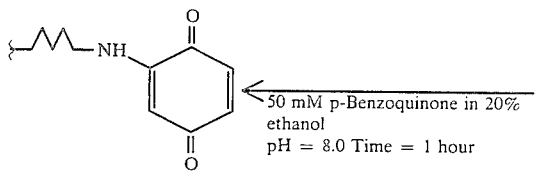

Method 2

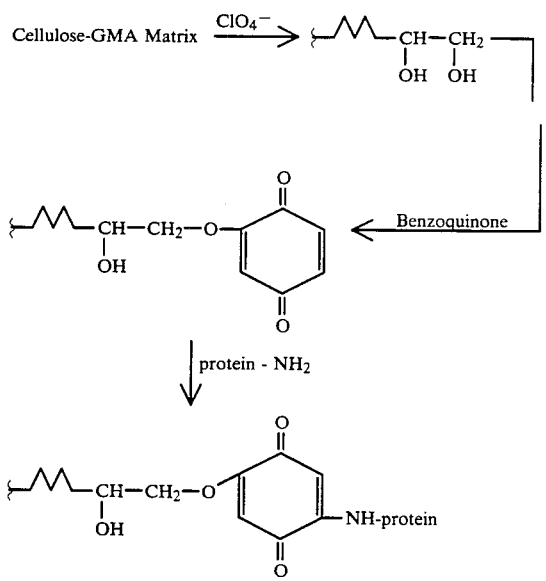

It is now known that for the coupling of an antibody or enzyme inhibitor to a solid matrix, to have maximum affinity for the antigen or the enzyme, it is important that the ligand retain its active conformation after coupling to the matrix. Antibody molecules exist in their active forms only in a small number of conformations. The functional affinities vary widely upon coupling to a solid surface. Thus, the noncovalent interactions between the matrix and ligand with forces such as hydrogen bonding and hydrophobic interactions have manifest influence on antibody conformations. Since antibodies are bulky in structure, the physical character of the matrix, such as surface area and pore distribution, also is a consideration from a steric hindrance point of view. For example, it has been found that above the level of about 3-4 mg/gm of IgG bound to Sepharose ®, additional bound IgG is ineffective as a ligand. Apparently, as higher levels of IgG are coupled to the Sepharose ®, antibody activity actually diminishes due to crowding of IgG, preventing the action of the antibody. Using cellulose as a substrate, maximum activity is attained at a higher level of substitution, 7 mgs. of IgG per gram of cellulose. However, by increasing the distance between the substrate and the active binding site, for example by the use of a "spacer arm," additional binding capacity is possible. Accordingly, increased antibody activity is possible by the introduction of a hydrophilic spacer arm according to the following reactions:

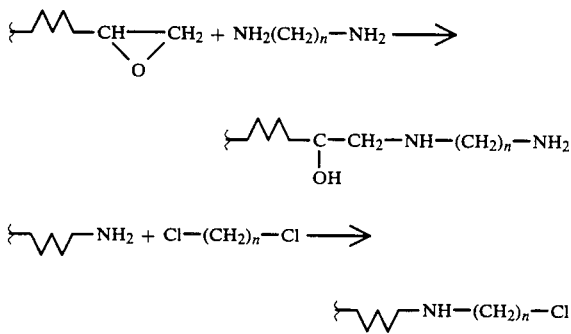

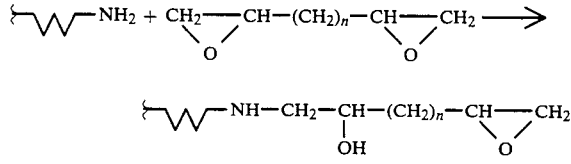

As mentioned above, the synthetic polymer-modified substrates of the present invention may be carefully tailored to particular needs by crosslinking the synthetic polymer and/or substrate. Crosslinking may be provided either by incorporating into the polymerization recipe a small amount of polyunsaturated comonomer having at least two polymerizable alpha, beta-carbon double bonds, such as for example mono-and polyethylene glycol dimethacrylates and diacrylates (with the polyethylene glycol residue containing up to six ethylene groups), ethylene diemethacrylate, tetraethylene diacrylate, divinylbenzene, triallyl cyanurate, methylene-bis-acrylamide or -bis-methacrylamide, and the like.

Another type of crosslinking agent utilizes the presence of a free pair of electrons on the aminoalkyl nitrogen atoms, where present. In this case, crosslinking may be carried out with such bifunctional reagents as would react with nitrogen free electron pairs, including the diacyl halides such as $Hal-CO-(CH_2)_n-CO-Hal$, or the alkyl dihalides, such as $Hal-(CH_2)_n-Hal$, wherein Hal is a halide such as chloride, bromide or iodide, and n may be anywhere between 2 and 12. Analogues of these compounds wherein $-(CH_2)_n-$ is replaced with phenyl are contemplated as well.

The amount of cross-linking agent is best determined empirically. It is to be considered sufficient when the polymer has achieved the desired structural integrity and porosity. Ideally, an amount of crosslinking agent between 5-20 mole percent of the synthetic polymer units is sufficient.

Typical ligands include, but are not limited to, DNA blood type antigen, anti-alpha feto protein, $C_1Q$, protein A, protein G, polylysine, mucopolysaccharides such as heparin, methylated albumin, tryptophan, phenylalanine, concavaline A, and the like. For removal of proteolytic enzymes from IgG, episilonaminoacrylic acid, lysine, methyl-p-aminocyclohexane carboxylic acid, and trasylol, potential inhibitors, are most effective. For removal of mucopoly-saccharides such as heparin, low molecular weight basic proteins (protamines) such as protamine sulfate are useful. For removal of kallikrein and PKA, benzamidine is effective. For removal of endotoxins, polymyxin-B-sulfate is effective.

As will be recognized by one skilled in the art, ligands suitable for the practice of the present invention include all ligands which may be immobilized by the invention affinity matrix and still maintain biological activity, such ligands being represented by, but not limited to, the following general classes: amino acids; avidinbiotins; carbohydrates; glutathiones; hydrophobic matrices; immunoglobulins; insoluble proteins; lectins; nucleotides; polyamino and polynucleic acids; and specialty ligands.

Typical amino acids suitable as affinity ligands include L-alanine, L-arginine, L-asparagine, L-aspartic acid, L-cysteine, L-cystine, L-glutamic acid, L-glutamine, glycine, L-histidine, L-isoleucine, L-lysine, L-methionine, L-phenylalanine, L-proline, L-serine, L-threonine, L-thyroxine, D-tryptophan, L-tryptophan, L-tyrosine and L-valine.

Typical avidin-biotin ligands include avidin, biotin, desthiobiotin, diaminobiotin, and 2-iminobiotin.

Typical carbohydrates include the glucosamines, the glycopryranoses, the glactosamines, the fucosamines, the fucopyranosylamines, the galactosylamines, the glycopyranosides, and the like.

Typical glutathione ligands include glutathione, hexylglutathione, and sulfobromophthalein-S-glutathione.

Typical hydrophobic matrices include amino allyl, butyl, decyl, dodecyl, ethyl, hexyl, methyl, octyl, pentyl, phenyl and propyl.

Typical immunoglobulins include the IgG's, including anti-goat IgG, anti-human IgG, anti-mouse IgG, anti-rabbit IgG, goat IgG, human IgG, rabbit IgG, and anti-glucose-6-phosphate dehydrogenase.

Typical insoluble proteins include aprotinin, fetuin, gelatin, globin, glycophorin, hemoglobin, insulin, lactalbumin, parvalbumin, protamine, protein-A, protein-G, ribos-binding protein, and trypsin inhibitor.

Typical lactins, include *Arachis hypogaea*, concanavalin A, *Dolichos biflorus*, glycine max, *Lens culinaris, Phytolacca americana, Pisum sativum*, and the like.

Typical nucleotides include the adenosine mono- and diphosphates, the cytidine di- and triphosphates, flavin mononucleotide, the guanosine mono-, di-, and triphosphates, and the uridine mono-, di-, and triphosphates.

Typical polyamino and polynucleic acids include DNA, polyadenylic acid, polycytidylic acid, polylysine, polyriboadinylic, polyribocytidylic, polyriboguanylic, polyriboinosinic acid, and polyuridylic.

The affinity matrices of the present invention involve the coupling of a ligand to the substrate-synthetic polymer matrix. Typically, any ligand which may be immobilized in the stationary phase and used to bind complementary molecules from a solute phase by affinity chromatography is contemplated.

The affinity matrices of the invention may be configured within a device which allows radial or tangential flow of sample. By "radial" flow is intended where the sample is passed through the affinity matrix. By "tangential" flow is intended where the sample flows across the surface, but not through the affinity matrix.

GENERAL PREPARATORY TECHNIQUES

The composite material formed by copolymerization of vinyl monomers followed by covalently linking to the cellulosic substrate may be made in paper form of different thickness. The affinity matrix thus made may be die cut and installed in an appropriate holder, either discs, columns, cartridges or plates.

Typical affinity matrices of this invention include those containing primary amino groups ("Type A") formed through amination reaction of GMA and those containing aldehyde groups ("Type G") formed through periodate oxidation of GMA as shown above. Where additional spacer arm length is desired, it is possible to utilize combinations of, for example, dialdehydes and diamines, alternately, and create spacer arms of any desired length.

The ligand immobilization procedure for Type A and G affinity matrices are fully described as follows:

PROCEDURE FOR LIGAND IMMOBILIZATION TO TYPE A AFFINITY MATRIX

Type A matrices have free primary amino groups at the end of hydrophilic spacer arms ($>10A°$). This is very convenient for small scale ligand immobilization and affinity purification of proteins, enzymes, antibodies, etc.

These Type A matrices comprise a composite material formed by covalent attachment of synthetic polymers to polysaccharide, i.e., cellulosic substrates. Amino functional groups are introduced into these matrices by covalent linkage of, for example, 1,6-diaminohexane, to activated composite material. The matrices thus formed are hydrophilic in nature and dimensionally stable due to properly controlled degree of cross-linking. Dimensional changes under pH and salt conditions are negligibly small. The matrix structure has sufficient rigidity to withstand high liquid flux for fast flow, yet is highly porous to facilitate mass transfer through the matrix where configured for radial flow. The free primary amino groups are capable of coupling ligands containing acylazide, carboxyl and aldehyde groups. One embodiment of the present invention comprises the pre-ligand intermediate with free primary amino groups.

Chemistry of Coupling

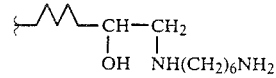

Aldehyde groups may be generated in the matrix by reaction with glutaraldehyde.

The aldehyde groups thus generated will take part in coupling reactions with ligands containing amino groups. Another embodiment contemplates the aldehyde-terminated intermediates.

Glutaraldehyde Activation of Type A Matrices

Type A matrix is activated by glutaraldehyde to make it suitable for immobilizing ligands containing amino groups, preferably primary aliphatic amino groups.

A. Materials
1. Buffer A—Na Phosphate (0.1M; pH 7.3)
2. Buffer B—Na Phosphate (0.05M) containing 0.25M NaCl (final pH: 7.6)
3. Buffer C—Na Phosphate (0.05M) with 0.25M NaCl (final pH: 6.5)
4. Glutaraldehyde—10% glutaraldehyde in Buffer A.
5. Glycine ethylester hydrochloride—1% solution in Buffer C. Adjust pH to 6.5. Add 100 mg $NaCNBH_3$ per 100 ml of above solution.

B. Activation
1. The Type A matrix is equilibrated by Buffer A at room temperature.
2. The prepared glutaraldehyde solution (see A.4 above) is recirculated at room temperature for 6 hours.
3. Excess glutaraldehyde is removed by washing with buffer A. The eluate is monitored for removal of glutaraldehyde by Schiff reagent solution. The matrix is ready for coupling with ligands containing amino groups once all excess glutaraldehyde is removed. Alternatively, the matrix may be stored, i.e., at 4° C.

C. Ligand Coupling
1. Amino functional ligand solutions are prepared in suitable buffers*, pH 6 to 8.5, containing $NaCNBH_3$ (i.e., 1 mg/ml in ligand solution) and recirculated through the matrix for 6-16 hours at room temperature or at 4° C. *Buffers containing amino functionalities (e.g., Tris, glycine, ethanolamine, etc.) should not be used.
2. The uncoupled ligand is removed by washing with the same buffer until the baseline is obtained.
3. Excess active groups are deactivated by circulating glycine ethylester hydrochloride at about pH 6.5 in the presence of $NaCNBH_3$ for about 4 hours at room temperature. 1 g of glycine ethylester hydrochloride dissolved in 100 mL buffer C; pH adjusted; followed by addition of $NaCNBH_3$ to a final concentration of 1 mg/mL.
4. Reagents are removed by washing with any desired buffer (pH 5 to 7.6) containing 0.25 to 0.5 M NaCl.

D. Measurement of Ligand Coupled
The amount of ligand coupled to the matrix is calculated indirectly by measuring the amount of uncoupled ligand solution left in the buffer solution (Step C.2). Dialysis of the residual ligand solution is necessary to remove the reaction by-products which may interfere in the measurement.

PROCEDURE FOR LIGAND IMMOBILIZATION TO TYPE G AFFINITY MATRIX

The Type G matrix is very convenient for small scale ligand immobilization and affinity purification of proteins, enzymes, antibodies, etc.

Type G matrices comprise a composite material, formed by covalent attachment of synthetic polymers to polysaccharide, i.e., cellulosic substrates. Functional groups capable of coupling amino functional ligands are introduced into the composite structure in the form of polymers. Typically, GMA-grafted cellulose is reacted with perchlorate to produce the hydroxylated intermediate. Further reaction with periodate produces the aldehyde termination. The matrices, thus formed, are hydrophilic in nature and dimensionally stable due to properly controlled degree of cross-linking. Dimensional changes under pH and salt conditions are negligibly small. The matrix structure has sufficient rigidity to withstand high liquid flux for fast flow, yet is high porous to facilitate mass transfer through the matrix. The matrix has abundant vicinal hydroxy groups, which are readily available for periodate oxidation. Aldehyde groups, thus generated, take part in the coupling reaction with free primary amino groups, preferably aliphatic amino groups. Both low and high molecular weight ligands [L] (lysine, p-aminobenzamidine, protein A, albumin, IgG, etc.) have been immobilized to the affinity matrix with high coupling efficiencies. A flow sheet representation of a typical affinity matrix preparation appears below.

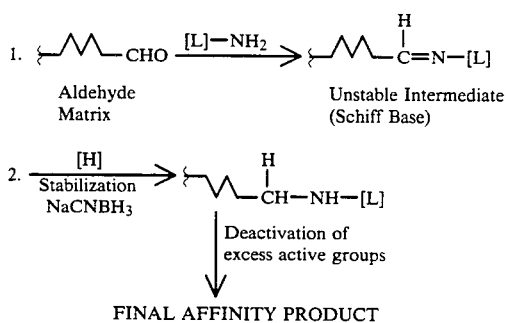

FINAL AFFINITY PRODUCT

A. Materials
1. Sodium phosphate buffer 0.05M with 0.25M NaCl; optimum pH 6.0–8.0. Favorable pH values for coupling:
   albumin—7.0–8.0
   IgG—6.5–8.0
   p-aminobenzamidine—6.2
   NOTE: Buffers containing amino functionality (e.g., Tris, ethanolamine, etc.) should not be used.
2. Sodium meta-periodate ($NaIO_4$): freshly prepared aqueous solution (1.5%).
3. Glycine ethylester hydrochloride: 1% aqueous solution.
4. Sodium cyanoborohydride ($NaCNBH_3$). This reagent must be fresh (Store in a dessicator when not in use.)

B. Procedure
1. The affinity matrix is assembled with tubing and connected to a small laboratory pump.
2. The matrix is washed with 100 ml (5 volumes) of deionized water. Freshly prepared aqueous solution of $NaIO_4$ (1.5%) is passed at 4–6 ml/min for ½ to 2 hours at room temperature. Maximum activation occurs when the oxidation is continued for 2 hours.
3. The matrix is washed with 200 ml (10 volumes) of deionized water to remove $NaIO_4$. The conductivity and $O.D._{280}$ of the eluate is checked to determine the removal of $NaIO_4$.
4. The matrix is equilibrated with approximately 200 ml of an appropriate phosphate buffer (as described in the Materials Section).
5. A solution (10 mg/ml) of the ligand is prepared in equilibration buffer. The ligand solution is recirculated (4h–10h) at 4–5 ml/min in presence of $NaCNBH_3$ (final concentration 1 mg/ml in ligand solution*. A minimum of 10 mg $NaCNBH_3$ is necessary for those ligand solutions which are less than 10 ml. *Dissolve NaCNBH$_3$ in buffer such that 50 μl of NaCNBH$_3$ is sufficient to bring the final concentration in the ligand solution to 1 mg/ml. Since the NaCNBH$_3$ reagent is susceptible to decomposition, during storage, the addition of NaCNBH$_3$ solution (50 μl) should be repeated 2 to 3 times during the course of the coupling procedure.

6. The uncoupled ligand is removed by washing with phosphate buffer until the O.D. stabilizes at baseline.
7. Excess active groups are deactivated by circulating the glycine ethylester hydrochloride solution at pH 6.5 in the presence of NaCNBH$_3$ for about 4 hours at room temperature. Dissolve 1 g of glycine ethylester hydrochloride in 100 ml of equilibration buffer; adjust pH to 6.5. Then add NaCNBH$_3$ to make final a concentration to 1 mg/ml.
8. Excess reagents and residual uncoupled ligands are finally removed by alternately washing the matrix (four times) with high and low pH buffer solutions each containing 0.25 to 0.50 M NaCl.
9. Standard established procedures are followed for applying sample and for elution of desired product.
10. The ligand coupled matrix may be stored at 4° C. in 0.02% sodium azide with 0.9% NaCl or suitable preservative (pH 6.0–7.0).

Measurement of Ligand Coupled

The amount of ligand coupled to the matrix is calculated indirectly by measuring the uncoupled ligand left in the buffer solution (Step 6). In case of low molecular weight ligands (e.g., p-aminobenzamidine, lysine, etc.) the measurement is done by a suitable color reaction or U.V. In case of macromolecules (e.g., protein A, antibodies, etc.) dialysis of the uncoupled ligand solution is necessary to remove the reaction by-products which may interfere in the measurement.

ENZYME REMOVAL USING AFFINITY MATRIX

1. Removal of Plasminogen From IgG

The blood coagulation metabolism existing in the human body occurs with two opposing processes, a fibrin-forming one associated with the blood coagulation system, and a fibrin-removing process directed by the fibrinolysin system. In normal physiological conditions, the two systems remain practically inactive. However, in the emergency state, a considerable amount of plasmin is suddenly activated from inactive precursors by intrinsic blood factors and the system is unbalanced. Clinical study has shown that the blood of individuals who have died suddenly under stresses might be in liquid and incoagulable form. This condition is now known to be due to proteolytic dissolution of fibrin by plasmin which has been activated from plasminogen. Therefore, plasminogen must be removed from IgG to eliminate the fibrinolytic effect and to avoid fragmentation of IgG.

Both plasminogen and plasmin behave as if they were gamma globulin. The isoelectric point of plasminogen has been estimated to be pH 5.6. It is probably a glycoprotein and contains small amounts of phosphorus. The molecular weight has been reported to be 143,000 or 84,000 by different investigators. The molecule behaves as if it were asymmetric in shape with an axial ratio of 9 to 16. The chemical properties of human plasmin are similar to those of plasminogen, but the molecular weight is slightly smaller due to splitting off of some molecules during activation. The conversion of plasminogen to plasmin involves change of shape from asymmetric to more compact spherical type.

The removal of proteolytical enzymes from IgG is effected by passing the solution through an affinity matrix bonded with an enzyme inhibitor. Among all the potential inhibitors of the plasminogen system, the following three were found to be most effective;
(1) Epsilon-aminocaproic acid or lysine,
(2) Methyl-p-aminocyclohexane carboxylic acid,
(3) Trasylol.

In a preferred embodiment, the inhibitor, i.e. epislon-aminocaproic acid, is bound to a cellulose-GMA matrix, utilizing a CNBr activation. Further, since certain quaternary amines were found to exhibit plasmin activity and with plasminogen having isoelectric point 5.6, plasminogen removal by QAE and DEAEMA matrix occurs to a certain extent.

Methods of Measuring Plasminogen Activities

Caseinolytic method: Techniques developed to measure the concentration of plasminogen in human plasma depend on the proteolytic activity of plasmin. Plasminogen cannot be directly determined, but must be converted into plasmin through activation with urokinase and subsequently determining the plasmin formed from its proteolytic activity with certain substrates. Although the physiological substrate from plasmin is fibrinogen, synthetic substrate such as casein is preferred for better sensitivity and reproducibility. The principle of the caseinolytic method is to analyze the ability of the plasminogen in plasma to digest casein in a given time and be expressed as plasminogen activity. Such activity can be measured by the amount of tyrosine equivalent released from hydrolytic dissolution of casein due to the proteolytic effect of plasmin. A standard procedure was established by NHI (National Heart Institute) Committee on Thrombolytic Agents.

2. Affinity Matrix For Kallikrein Removal

IgG made by the Cohn cold ethanol fractionation method is known to contain undesirable, deleterious exogenous activity such as prekallikrein activator (PKA) activity, activated clotting factor, and esterase activity. Those exogenous activities have been reported on intravenous administration to cause hypotensive reaction in patients, Alving et al., *New England J. Med.* 299:66 (1978). By binding the enzymatic inhibitor as ligand on, for example, a cellulose substrate, preferred is cellulose modified as above, proteolytic enzymes such as kallikrein are eliminated from the plasma. Kallikrein, like other serine proteases, is also inhibited by synthetic compounds such as p-carboethoxy phenyl epsilon guanidine caproate. Benzamidine bound to cellulose-GMA is preferred as affinity ligand for kallikrein removal.

Hydrophobic comonomers (b)(ii) are normally added to a copolymerization mixture in the presence of alcoholic solvents and/or surfactants. Washing is then carried out with alcohols.

The preferred formation of self-supporting fibrous media from the modified polysaccharide materials of the invention can be carried out immediately after polymerization and polysaccharide modification. In this mode, anchoring of affinity ligands or biomolecules may be carried out on the formed sheets themselves.

Alternatively, the fibrous media is formed after anchoring of affinity ligands or biomolecules. The preferred method is to form the fibrous sheets after polysaccharide modification, and carry out further reactions, such as anchoring on the sheets.

A self-supporting fibrous matrix using the modified polysaccharide of the invention can preferably be made by vacuum filtering an aqueous slurry of fibers and, if desired, additional resins and modified or unmodified particulate. This forms a sheet having uniformly high porosity, fine pore-size structure with excellent flow characteristics and substantial homogeneity with respect to fiber, resins and particulate.

The vacuum filtration is performed on a foraminous surface, normally a woven wire mesh which, in practice, may vary from 50 mesh to 200 mesh, with mesh openings ranging from 280 micrometers to 70 micrometers, respectively. Finer meshes are unsuitable because of clogging problems and/or structural inadequacy.

The sequence of adding the overall components to the slurry (modified fibers, other fibers, particulates, modified particulates, other resins, etc.) is relatively unimportant, provided that the slurry is subjected to controlled hydrodynamic shear forces during the mixing process. The slurry is normally prepared at, say, about 4% consistency and then diluted with additional water with a proper consistency required for vacuum filtering and sheet formation. This latter consistency will vary depending upon the type of equipment used to form the sheet. Typically, the slurry is cast onto a foraminous surface, vacuum filtered and dried in the conventional manner.

The flat, dimensionally stable sheet can be of any desired thickness and is then cut to the appropriate dimensions for each type of application. In one embodiment, the wet sheet is dried and then cut to proper size in order to form discs. These discs can be loaded onto an appropriately sized cylindrical column to form the desired medium. The disc and cylinder should preferably be in interference fit so that the disc can be pushed into the cylinder without distortion, but cannot fall under gravitational force allowing gaps between the discs and the cylinder. After the column is packed dry, a pump can be used to pump solvent through the elements stacked in the column. In some embodiments, the elements swell to form a substantially tight edge seal to the cylinder wall. Because the individual elements are dimensionally stable, the column is not sensitive to orientation or handling, a problem which is common with other chromatographic media, particularly of any gel type media. However, the media is equally suitable for use in sheet configuration.

In another embodiment, the stationary phase, in sheet form, is used as the stationary phase in a chromatography column utilizing a conventional column configuration. One such column is described in U.S. Pat. No. 4,496,461 to Leeke et al., incorporated by reference herein in its entirety.

In one embodiment depicted in FIG. 1, the radial flow column, which may be in cartridge form, generally designated 10, is comprised of a cylindrical stationary phase 12, and cylindrical tube 13, which form a cylindrical chamber 14 which acts as a housing for the stationary phase 12. The solid stationary phase 12 can be inserted into chamber 14 formed by a glass, metal or polymeric tube or cylinder 13 having a diameter somewhat larger than the external diameter of the stationary phase 12. Suitable fluid admission, collection and monitoring systems can also be employed with the column as in conventional analytical and preparative columns. The stationary phase 12 is positioned within the chamber 14 and preferably has a longitudinal axis 16 coaxial with the axis of the cylindrical chamber 14. Optionally, a plurality of cartridges may be placed in a single housing in various configurations to effect parallel and/or series flow between the cartridges (not shown). The solid stationary phase has chromatographic functionality and is effective for affinity and reverse phase chromatographic separation.

Figure 2:
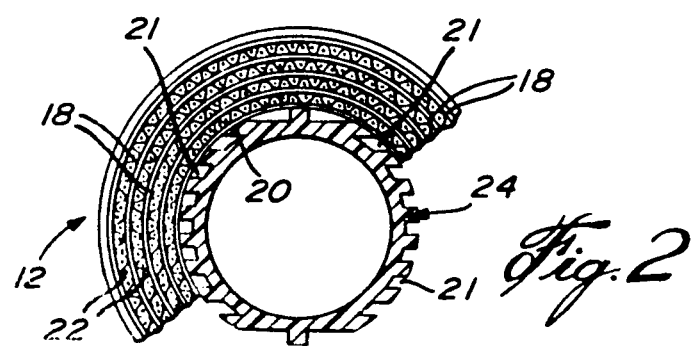
FIG. 2 is an enlarged cross-sectional view taken along line 2—2 of FIG. 1.
Figure 3:
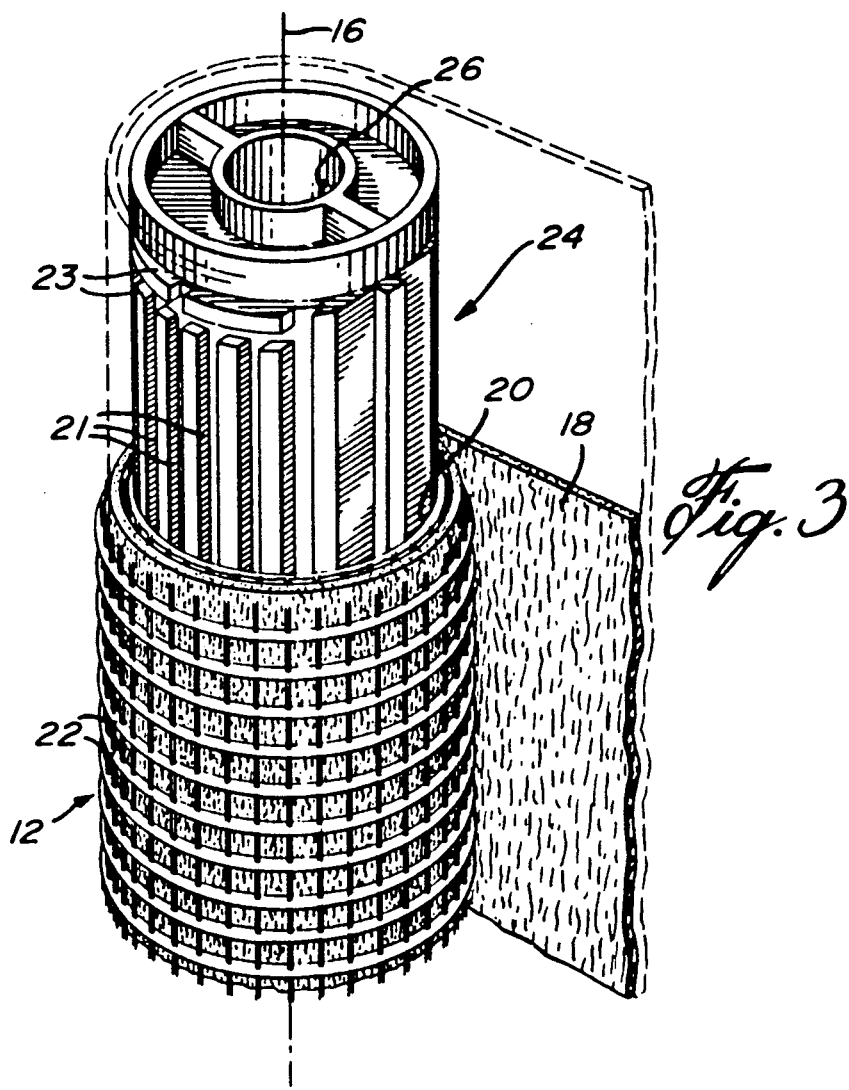
FIG. 3 is a perspective view of the radial flow cartridge with a portion of the solid stationary phase broken away therefrom showing the spirally wound chromatographic media and spacer means therebetween.

Referring to an embodiment shown in FIGS. 2 and 3, the stationary phase 12 is constructed of a swellable matrix 18, which may be hydrophilically swellable, in sheet form which is the active media for chromatographic separation. In one embodiment, the matrix is fibrous. The chromatographic media in sheet form 18 is sandwiched between a single non-woven mesh 22 or plurality of mesh. The composite sheet of chromatography media 18 and mesh 22, e.g., non-woven, is spirally wound around a cylindrical core 24 having a longitudinal axis 16 to form a plurality of layers around the axis 16. The core 24 is provided with a plurality of longitudinal and axially oriented channels 21 for directing the liquid into circumferential channels 23 which are in fluid communication with core 24. The mesh 22, due to the openness and thickness thereof, acts as a spacer means between each layer of media 18 which permits the controlled swelling of the media and enhances the distribution of the sample flowing through the stationary phase 12. The cylindrical core 24 is provided with apertures 26 near the top thereof for the flow of sample from the circumferential channels 23 into the open interior of the core.

Referring to FIG. 1, the wound composite sheet 18 and 22 and core 24 are then capped by stationary phase end caps 32 and 34. The stationary phase end caps 32 and 34 of this subassembly are sealed by thermoplastic fusion to the core 24 and also to the ends of the composites 18 and 22. The subassembly, comprising 18, 22, 24, 32 and 34 is then slipped into chamber 14. The cylinder end cap 36 is then thermoplastically fused to the top edge 31 of cylinder 13. The fluid or sample 42 can thus flow radially from the outside through the solid stationary phase to the open channel 21 of core 24, since the interior and exterior are completely separated by the solid stationary phase and sealed off by stationary phase end caps 32 and 34.

The preformed stationary phase end caps 32 and 34 are preferably applied to the cylindrical solid stationary phase 12 by heating an inside face of the thermoplastic stationary phase end cap to a temperature sufficient to soften a sufficient amount of the stationary phase end cap to form a thermoplastic seal with the ends of the core 24 and composite sheet 18 and 22. All of the edges are then embedded into the softened material. The softened material is then hardened, typically by ambient conditions, to form a thermoplastic sealing relationship between the sealing surface of the stationary phase end caps 32 and 34, the core 24 and the ends of the solid stationary phase 12 to form a leak-proof seal. Such method of applying stationary phase end caps are well known in the filtration art. See, for example, U.S. Ser. No. 383,383 and U.S. Ser. No. 383,377, filed on May 28, 1982, to Meyering et al. and Miller, respectively. Optionally, the stationary phase end caps can be molded integrally in situ onto the solid stationary phase.

Stationary phase end caps of thermoplastic materials are preferred because of the ease of bonding, but it is also possible to use thermo-setting resins in a thermoplastic, fusible or heat-softenable stage of polymerization, until the bondings have been effected, after which the curing of the resin can be completed to produce a structure which can no longer be separated. Such a structure is autoclavable without danger of destroying the fluid tight seal, the solid stationary phase 12, and the stationary phase end caps 32 and 34. Thermoplastic resins whose softening point is sufficiently high so that they are not softened under sterilizing autoclaving conditions are preferred for biomedical use. Exemplary of the plastic materials which can be used are polyolefins.

Referring to FIG. 1, one preferred column 10 has a stationary phase end cap 34 on one end which does not open to the exterior of the subassembly 18, 22, 24, 32, and 34 but is closed off. This stationary phase end cap 34 can nest on the bottom end wall 44 of cylinder 13 while still permitting the flow of sample 42 into chamber 14 around the outside of stationary phase 12, or this lower stationary phase end cap 34 of the subassembly 18, 22, 24, 32 and 34 is in spaced apart relationship from the bottom end wall 44 of cylinder 13, thus permitting the flow of sample 42 into the chamber 14.

The upper end of cartridge 40 has a cylinder end cap 36 which is in fluid communication with channels 21 of cylindrical core 24, thus permitting the flow of fluid from the outer periphery of cylindrical core 24 to the center of core 24 to the outside of cylinder end cap 36. The cylinder end cap 36 has molded thereon fitting 48 for fluid connection through a collection means (not shown).

Referring to FIG. 2, prior to winding the chromatography media 18 on the core 24, the exterior surface of core 24 may be completely wrapped with a scrim material 20. Additionally, after winding the chromatography media 18 on the core 24, the exterior surface thereof may be completely wrapped with mesh material 22.

FIGS. 4 through 10 depict another embodiment of the chromatography column of this invention, the embodiment wherein the column is in disc configuration, again wherein like character references indicate like parts.

Referring to FIGS. 4-10, the column in disc configuration, generally designated 110, comprises an inlet housing member 112, an outlet housing member 114, and a stationary phase 116.

The inlet housing member 112 comprises a sample inlet means 118, baffle means 120, and sample distribution means 122. The sample inlet means 118 is in communication with the sample distribution means 122.

The sample distribution means 122 comprises plural radial distribution channels or grooves 130 and plural concentric distribution channels 140, the radial distribution grooves 130 and concentric distribution channels 140 being in communication with each other and with inlet means 118. Radial distribution grooves 130 comprise distribution groove bottom portions lying in a plane represented by line $P_1$ in FIG. 10 and $P_1'$ in FIG. 12, and distribution groove wall portions 134a and 134b. Concentric distribution channels 140 comprise concentric distribution channel bottom portions 142, concentric distribution channel wall portions 144a and 144b, and concentric distribution channel apex portions 146.

Optionally, the inlet housing member 112 may contain a venting means 150, the function and operation of which will be defined below. The venting means is in communication with a chamber 152. Chamber 152 is formed by inlet housing member 112 and outlet housing member 114 (see FIGS. 4 and 10). Chamber 152 contains the stationary phase 116.

The outlet housing member 114 comprises a sample collection means 154 and sample outlet means 156, sample collection means 154 being in communication with sample outlet means 156.

Sample collection means 154 comprises plural radial collection grooves 160 and plural concentric collection channels 170. Radial collection grooves 160 and concentric collection channels 170 are in communication with each other and with sample outlet means 156.

Figure 4:
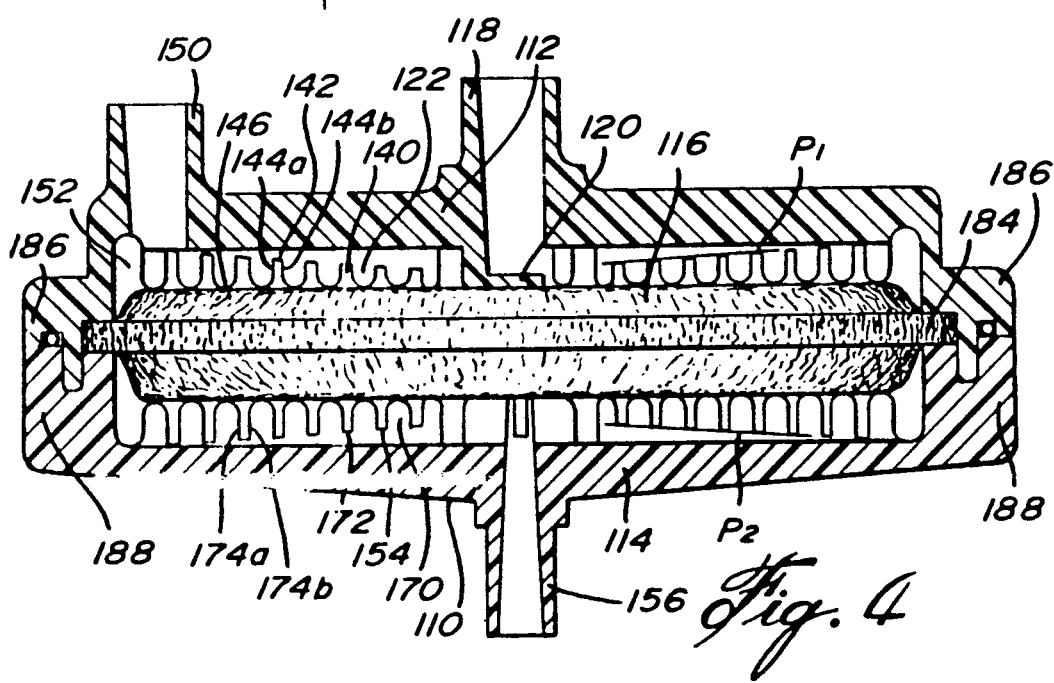
FIG. 4 is a cross-sectional view of another embodiment of the invention wherein the chromatography column is in disc configuration.
Figure 5:
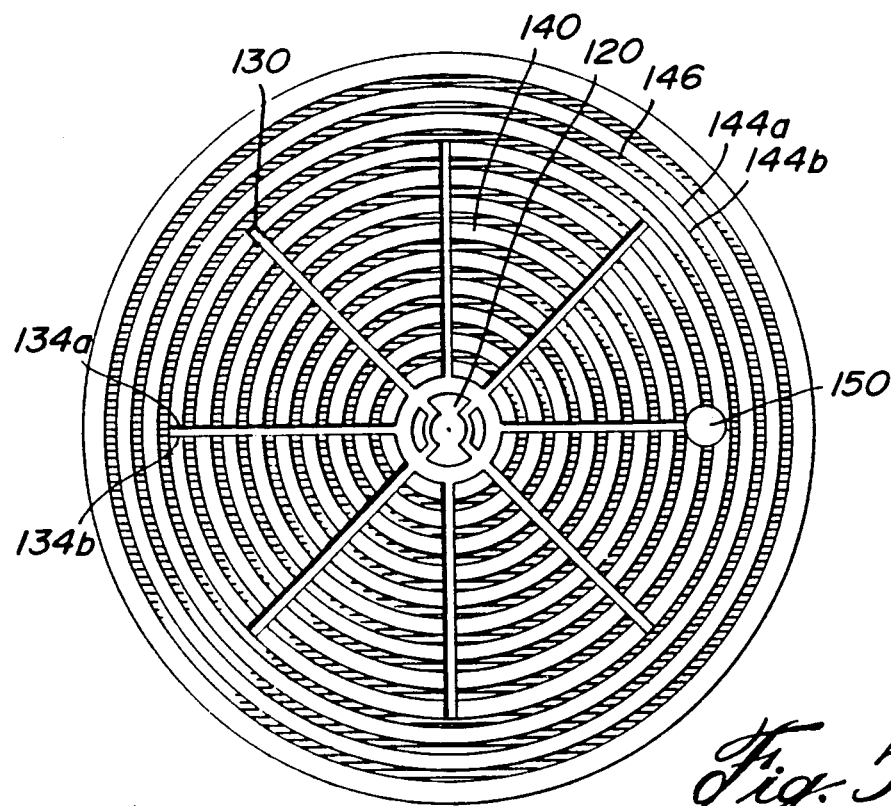
FIG. 5 is a top plan view of the inlet housing member of the invention embodiment in disc configuration.
Figure 6:
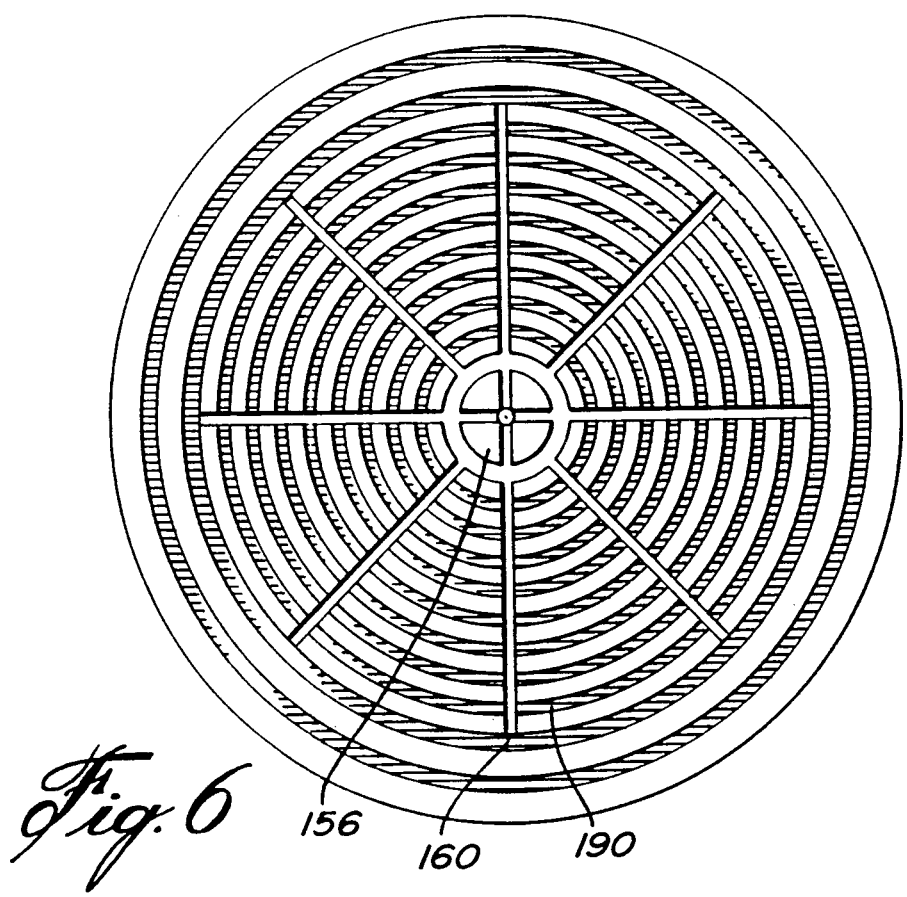
FIG. 6 is a top plan view of the outlet housing member of the invention embodiment in disc configuration.
Figure 10:
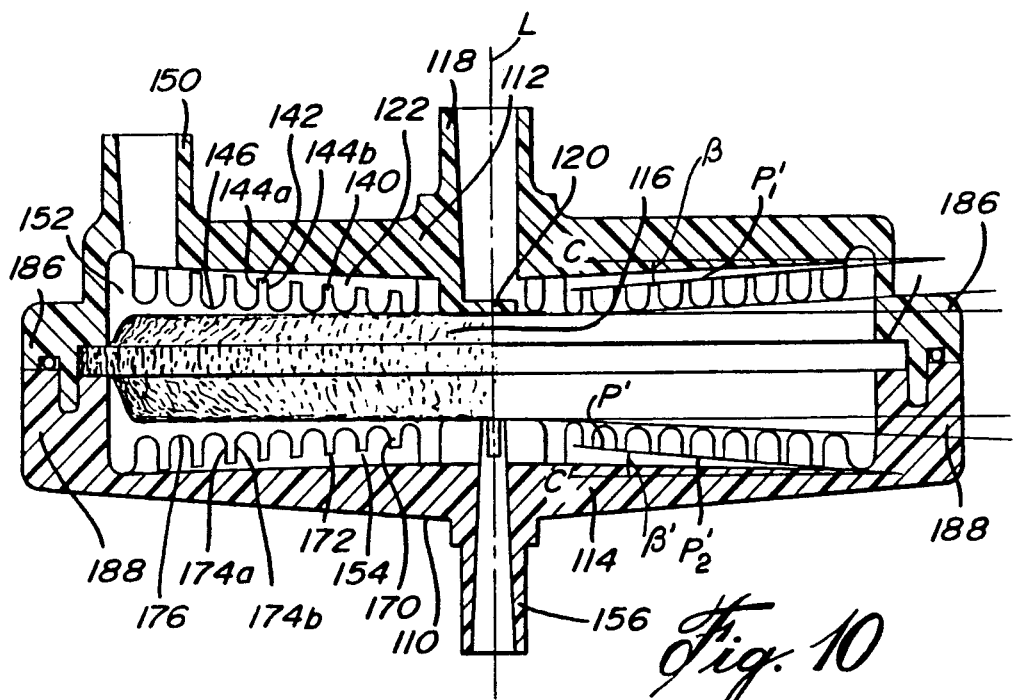
FIG. 10 is a cross-sectional view of a preferred configuration for the ion exchange column of the present invention in disc configuration. In this configuration, the housing in disc configuration forms a radially outwardly expanding chamber. A portion of the spacer means is removed for clarity.

Radial collection grooves 160 comprise radial collection groove bottom portions lying in a plane represented by line $P_2$ in FIG. 4 and $P_2'$ in FIG. 10, and radial groove wall portions 164a and 164b. Concentric collection channels 170 comprise concentric collection channel bottom portions 172, concentric collection channel side wall portions 174a and 174b and concentric collection channel apex portions 176.

Figure 7:
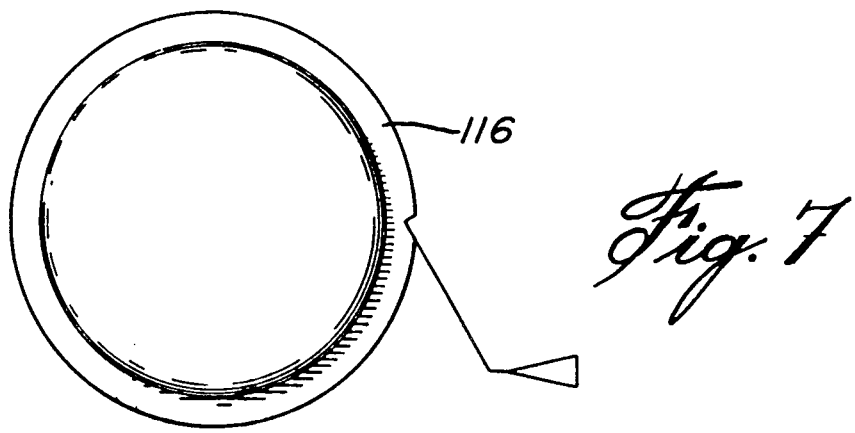
FIG. 7 is a top plan view of one embodiment of the stationary phase of the invention column in disc configuration.
Figure 8:
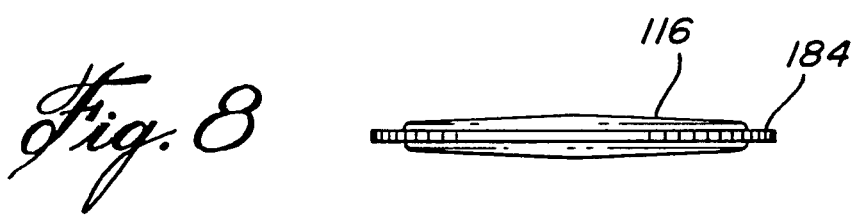
FIG. 8 is a side elevation of one embodiment of the stationary phase of the invention column in disc configuration.
Figure 9:
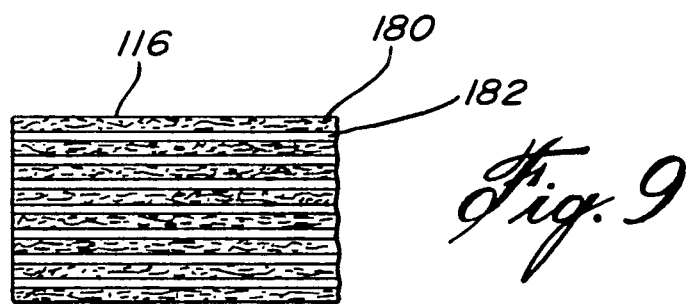
FIG. 9 is a cross-sectional view of one embodiment of the stationary phase of the invention column in disc configuration depicting a plurality of layers of separation media and spacer means interposed between adjacent layers of said separation media, prior to the sonic welding of the peripheral edges.

Stationary phase 116 has chromatographic functionality and is effective for chromatographic separation. Referring to FIGS. 7, 8, and 8 in particular, the stationary phase 116 may comprise a plurality of layers of a matrix 180 in sheet form, having chromatographic functionality and being effective for chromatographic separation, and an optional spacer means 182 between each adjacent layer of swellable matrix 180. This configuration is best shown in FIG. 9, a cross-sectional view of one embodiment of the separation phase 10. The matrix may be a swellable matrix. In one preferred embodiment, the swellable matrix is fibrous.

If swellable, the matrix 180 may be hydrophilic swellable and comprises the active media for chromatographic separation. The optional spacer means 182 may be typically a woven or non-woven mesh similar to mesh 22 of FIGS. 2 and 3 above and is further described below. The mesh, due to the openness and thickness thereof, acts as a spacer means between each layer of matrix 180 and permits the controlled expansion thereof without closing off the porous structure of the media, thereby enhancing the distribution of the sample flowing radially through the stationary phase 116.

As may be seen from FIG. 8, a manner of conforming the stationary phase 116 is to produce a "sandwich" of alternating layers of swellable matrix in sheet form and layers of spacer means, with the periphery of the sandwich compressed into a fluid tight configuration 184. Typically, the peripheral edges of alternating discs of swellable matrix 180 and spacer means 182 are Joined. Preferably, the matrix 180 contains or has bonded therein a thermoplastic polymeric material. Similarly, in a preferred embodiment, spacer means 182 also is made of or contains thermoplastic polymeric materials. In this configuration, the edges may be optionally uniformly joined by appropriate means such as heat treating, sonic welding, etc. As may be seen from FIG. 4, in a preferred embodiment, the fluid tight peripheral configuration 184 is itself contained in a fluid tight, hermetic seal formed by the mating edges 186 and 188 of, respectively, the inlet housing member 112 and the outlet housing member 114. In this manner, sample entering through inlet means 118 must pass through stationary phase 116 prior to exiting through outlet means 156.

The disc configured chromatography column of FIGS. 4-10 is formed using conventional and well known fabrication techniques. The stationary phase 116, a preformed "sandwich" of alternating layers of swellable matrix and spacer means, with peripheral edges optionally sonically welded and configured as in FIG. 9, may be placed in inlet housing 112 and outlet housing member 114 is placed thereover. Subsequently, the mating edges 186 of the inlet housing member 188 and of the outlet housing member 190 are joined to form an airtight and fluid tight seal. When sonic welding is desired the technique described in Branson Sonic Power Company, Danbury, Conn., Information Sheet PW-3, 1971, incorporated by reference herein, may be employed.

Vent means 150, as mentioned above, represents an optional configuration of the disc embodiment of the column. Its purpose is to allow air in the column to exit the column during use. Typically, vent means 150 is adapted to be sealed off when all air has been removed from the system. In an alternative embodiment, vent means 150 contains a hydrophobic media which will allow the passage of gases but not liquids, as disclosed in U.S. Pat. No. 4,113,627, incorporated herein by reference.

In another embodiment, depicted by FIG. 10, chamber 152 is radially outwardly expanding. By the term "radially outwardly expanding" is meant that the volume at the interior chamber is less than the volume at the periphery of the chamber. In this configuration, referring to FIG. 10, the distance between distribution means 112 and collection means 114 at the interior, dI, is less than the distance between distribution means 112 and collection means 114 at the periphery $d_2$.

If the stationary phase 116 is hydrophilic swellable, sample solution on contact with separation phase 116 causes the separation phase to swell. As the separation phase swells, the pressure differential between the inlet and outlet sides of the separation media increases, thereby restricting sample flow-through. By designing a housing as described above, i.e. in radially outwardly expanding configuration, the pressure differential between the inlet and outlet sides of the stationary phase decreases towards the periphery, thereby maximizing utilization of the chromatographic separation function of the stationary phase and substantially increasing the adsorption capacity of a given unit. The above-described housing design may also be employed for a stationary phase which is not swellable.

In another embodiment, also depicted in FIG. 10, the volume of each succeeding concentric distribution channel 140 and concentric collection channel 170 increases from the interior to the periphery of the chromatographic column. In this manner, clogging of the channels by the swelling of the hydrophilic swellable stationary phase is vitiated, thereby promoting uniform distribution of sample and maximum utilization of column capacity.

In the embodiment depicted in FIG. 10, lines A, A', C and C' are lines which represent cross-sectional view of parallel planes which are perpendicular to the longitudinal axis L of the chromatography column. Lines B and B', respectively, represent cross-sectional views of planes which are substantially tangent to the apices 146 and 176 of concentric distribution channels 140 and concentric collection channels 170. Planes B and B' form angles alpha and alpha' with planes A and A'. Thus, planes B and B', at angles alpha and alpha' to planes A and A', respectively, define a radially outwardly expanding chamber 152, which in turn defines the limits of expansion of stationary phase 116. As described above, the optimal configuration for the radially outwardly expanding embodiment is such that stationary phase 116 is just touching the most peripheral apices 146 and 176. If the stationary phase is swellable, then, in its maximally swelled status, it should just touch the most peripheral apices 146 and 176. It is to be understood that angles alpha and alpha' may be the same or different and may vary with the number of layers of swellable matrix and the particular matrix in use. Typically, alpha and alpha' are about $2\frac{1}{2}°$.

Lines D and D', respectively, represent cross-sectional views of planes which contain concentric distribution channel bottom portions 142 and concentric collection channel bottom portions 172 and define angles beta and beta' with planes C and C'. Thus, planes D and D', at angles beta and beta' to planes C and C', respectively, define the slope of the increasing depth of channels 140 and 170. In the embodiment of FIG. 10, beta and beta' are typically each about 5°. However, these angles may be varied, both with respect to one another and absolutely.

In similar manner, it is within the scope of the present invention to configure a chromatographic column such that radial distribution grooves 130 and/or radial collection grooves 160 increase in volume from the interior to the periphery of the column. Such a configuration is disclosed in U.S. Pat. No. 3,361,261, incorporated by reference herein.

As is understood by those skilled in the art, it is desirable to minimize the hold-up volume of a chromatographic column. With this in mind, an optimal design for a radially outwardly expanding chamber is that where the distance $d_2$ is such as to allow the swellable stationary phase to swell to its maximum, but with no unused space left. In this manner, the pressure differential at the periphery is minimized, while at the same time reducing hold-up volume to its lower limit as well. This housing configuration permits as well the use of a single layer of matrix or a plurality of layers of matrix with no spacer means interposed between layers. The radially outwardly expanding chamber coacts with the thus configured stationary phase to uniformly distribute sample thereacross.

In order to provide a chromatographic media matrix which is coherent and handleable, it is desirable that at least one of the components which go into forming the porous matrix be a long, self-bonding structural fiber. Such fiber gives the stationary phase sufficient structural integrity in both the wet "as formed" condition and in the final dry condition. Such a structure permits handling of the phase, in particular as a sheet, during processing and at the time of its intended use. Preferably, the sheets which form the chromatographic media are formed by vacuum felting an aqueous slurry of fibers. The sheets may also be pressure felted or felted from a non-aqueous slurry. The sheet shows a uniform high porosity, with excellent flow characteristics, and is substantially homogeneous. In general, the media can range in thicknesses from about 5 mils to about 150 mils (dry); however, thicker or even thinner media may be utilized provided the sheet can be spirally wound or layered to produce a column which can perform as described above.

It is important when constructing the chromatography column of this invention that the chromatographic media used in the column be of uniform thickness throughout its length and width and that the media have a substantially uniform density throughout. It is preferred that the layer of media be substantially homogeneous with respect to itself; however, for certain applications and material, it is understood that non-homogeneous construction may be employed.

Since the solid stationary phase is intended in use to effect separation by maintaining a substantial pressure differential across the solid stationary phase, it is essential that the solid stationary phase have a sufficient degree of compressive strength to withstand deformation under such loads as may be imposed upon it. Such compressive strength must not only exist in the media itself but in the spacer means (if present) and the internal core upon which the chromatography media, or solid stationary phase is compressed.

Due to the possible swellability of the media, an element of this invention is the spacer means between each layer of the media and/or the coaction of the chamber wall and the matrix. Such spacer means are not essential to this aspect of the present invention, and in one embodiment a chromatographic column may be prepared which does not contain such spacer means. In such a column, the self supporting matrices of the present invention comprise a single and continuous column medium. Spacer means may be omitted advantageously in columns whose matrices do not undergo extensive swelling. The spacer means permits controlled expansion of the media and enhancement of the distribution of sample flowing through the stationary phase. The spacer means located between each layer of the swellable chromatographic media provides for the distribution movement of the sample as the sample passes through the solid stationary phase. The spacer means functions to uniformly control thickness and density of the chromatographic media during use. In addition, the spacer means can serve as a backing or support for the layer of chromatographic media. This latter aspect is particularly useful during the manufacturing phase.

It is preferred that any spacer means used be composed of a material which is inert with respect to the chromatographic process. By inert, it is meant that the material does not adversely affect the function of the solid stationary phase.

Referring to FIGS. 2 and 3, the spacer means comprises the mesh 22. Alternatively, where the column design is as depicted in FIGS. 4–10, the spacer means 182 may also comprise a mesh, or scrim and mesh. A scrim material can function to channel, to a certain extent, the sample flowing through the media and substantially evenly disperse the sample axially and circumferentially across the media. The mesh material provides spacing between the media to permit controlled expansion thereof to prevent the "cut-off" to flow therethrough by compression of the permeable media and also assists in distributing or channeling the sample flowing through the media.

The mesh material is an open type of material having openings ranging, for general guidance, from 1/16 inch to ¼ inch.

It should be noted that the thickness of the optional spacer means, i.e. the scrim and particularly the mesh material, and the pore size of each to be used may be readily determined by one skilled in the art by performing tests which vary these factors. Such factors as the openness and thickness of these spacer means are highly dependent on the type of media utilized, e.g. swellability, wettability, thickness, chemical composition, etc., the flow rate of the sample through the stationary phase, the surface area of the stationary phase, e.g. number of windings, thickness of media, diameter of stationary phase, etc. It is thus very difficult to clearly specify these variables, other than to say that these may be determined by either trial and error or more elaborate testing procedures to determine the optimum parameters.

The preferred mesh material, at this time, is polypropylene CONWED (Grade TD-620).

The overall width of the stationary phase in accordance with the present invention can be infinite, the actual diameter being limited only by practical considerations such as space requirements. Since the diameter or width of the overall column can be increased without theoretical limitation, the sample size or amount of substance to be separated in the bed is not limited. Thus, the diameter can be increased to separate the desired amount of sample substance to be produced.

In operation the sample is driven through the stationary phase and separated into distinct chromatographic fractions by the chromatographic media. The optional spacer means induces and permits flow of this stream as it moves through the column and therefore provides for improved resolution and utilization of the media's potential capacity.

Referring to FIG. 1, the sample is preferably introduced at the bottom of the column flowing to the outer surface of the solid stationary phase and then flowing radially inward through the layers of chromatographic media and spacer means into the channels 21 of core tube 24 and is withdrawn centrally. It is apparent, from what has been set forth above, that the radial flow can also be caused to circulate in the opposite direction.

Referring to FIG. 4, sample is preferably introduced at the inlet 11B, passes to distribution means 122, is substantially uniformly distributed over the surface of the stationary phase 116 by radial distribution grooves 132 and concentric distribution channels 130, and passes through radial collection grooves 140 and concentric collection channels 170 and exits through outlet 156.

The chromatographic columns of this invention may be used for any of the well-known affinity and reverse phase chromatographic separations usually performed with conventional columns. Additionally, the columns of the present invention may be found useful in the areas where conventional columns are impractical.

Although the above embodiments may disclose only the radial distribution of materials through chromatographic medium, it is to be understood that non-radial distributions (e.g. linear or tangential distribution, as described in more detail below, etc.) may also be advantageously employed.

The columns of this invention can be used for separations in the analytical and preparative fields. The columns can be connected to all common types of chromatographic equipment. Several columns or cartridges of solid stationary phase can be connected in series or parallel. In large units, the columns can contain identical or different affinity or reverse phase chromatographic media and can be of identical or different length and/or diameter. See for example Daly et al., application Ser. No. 611,662, filed May 18, 1984, incorporated by reference herein. It has been found that the aforedescribed stationary phase produces unexpected results in that the flow of sample through the column is enhanced without destroying the adsorptive capacity of the media. Additionally, when protein and dye staining tests were performed it was found that the stationary phase of this invention provided even distribution of sample flow therethrough without an increase in pressure drop when compared to a stationary phase not utilizing the spacer means described herein.

The stationary phases decrease total processing time and when used with the proper chromatographic media has excellent binding capacity. The stationary phases may be used with standard type pumps, gravity feed, or syringes, utilized, in their preferred mode, at from 1 to 50 p.s.i., and even under vacuum. The stationary phases of chromatographic media are totally enclosed and completely self-contained to ensure sterile conditions. Due to the fact that the solid stationary phase is manufactured in a factory and assembled previously known columns and eliminates the dependence upon packing expertise.

By configuring the column to maximize sample distribution, minimize hold-up volume, and maximize stationary phase utilization by creating a differential pressure gradient which decreases from the interior to the periphery, the useful and effective life of the column is substantially improved.

These columns and discs are particularly useful in that means are provided for radially distributing sample through the media. Accordingly, sheets of media may be stacked in the columns of FIG. 1 in disc configuration, with or without spacer means.

For the purpose of purifying fluid samples containing cells, e.g. fermentation media or blood tangential flow of the blood across the affinity matrix is preferred. By the term "tangential flow" or "tangential flow across the media" is intended that the fluid sample is directed across, but not through the chromatographic media. A typical tangential flow configuration is described in U.S. Pat. No. 4,551,435 (1985) to Liberte, incorporated by reference herein. The difficulty in treating blood by flow through the media is due to the fact that blood comprises cells varying from 1 to 20 $\mu M$ in size together with over 400 different proteins. As shown in FIG. 14, when blood flows through a matrix 201, blood cells 219 tend to become caught on the surface of the matrix.

Lysis of cell walls, for example red blood cells, is associated with very high sheer stress, generally greater than 40,000 dynes/cm$^2$ for very short periods of time or about 3,000 dynes/cm$^2$ for times exceeding one second. The amount of sheer stress is also dependant on the surface area, surface properties of the matrix, adhesivity of blood components to the matrix, flow parameters and clotting mechanisms triggered by a particular matrix or wall. Hemolysis, or the liberation of free hemoglobin from the cell, is the primary indicator of red cell destruction.

Cell lysis can be reduced by tangential flow of the blood across the surface of the matrix which gives rise to sheer stresses of less than 3,000 dynes/cm$^2$. When blood flows tangentially to a surface a skimming layer or cell-free zone adjacent to the surfaces forms. When the skimming layer is lost, free hemoglobulin is released into the plasma and the resistance of the membrane rises. As shown in FIG. 14, tangential flow of blood across the matrix 201 allows cells 219 to pass across the media and at the same time allows the impurities to be adsorbed by the matrix. The combination of the improved matrix surface and separator design of the invention together with optimized flow conditions serve to overcome the problems of shear stress and cell lysis.

In general, cells adhere more readily to a high energy hydrophilic surface than to a hydrophobic low energy one. There is evidence that platelets, whose net surface charge is negative, adhere to surfaces bearing a gross positive charge, such as cationic polyelectrolytes and certain metals. However, an understanding of the interaction of platelets with polymeric surfaces will almost certainly await an understanding of surface adsorption on plasma proteins. Platelets are large and infrequent in comparison with dissolved plasma components and diffuse much less rapidly. It is highly probable that most of the platelets contact a surface that has already interacted with and become covered with a layer of plasma proteins. Therefore, the interaction of the polymeric surface with plasma proteins are a more important consideration than platelet interaction. The reactivity of the adsorbed protein molecules varies with the chemistry of the surfaces on to which the protein molecules are adsorbed onto, which in turn affects the clogging and blood flow characteristics.

The most traumatic spot in blood flow system is where there is a sudden change of tube diameter and flow direction. Thus, in designing a system for the purification of blood, it is necessary to reduce these factors. In addition, it is also necessary to avoid or reduce direct impingement of blood on a foreign surface.

Flow of blood in the system involves a shifting of molecular interactions between various components. In order to maintain the stability of the chromatographic separation device, any possible disturbance which may occur during the process of separation should be reduced as much as possible. Flow rate, pressure variation and viscosity change are the major parameters to be considered. Fortunately, plasma in blood functions as lubricant and diluent to keep cells apart and away from the walls of the device.

Another problem with blood flow within the device centers on the aggregation of cells around the flow conduits. When the blood stream passes from a single entrance conduit to an expanded chamber from which a large number of flowing channels originate, an area of stasis or disturbed flow with low shear results near the channel entrance, where platelets tend to adhere. In areas where local hemodynamics provide the proper combination of convective and diffusional transport, platelets soon adhere to the surface of the foreign material. Other platelets agglutinate with the adhered platelets to form an aggregate. As the separation progresses, these aggregates tend to coalesce and eventually obstruct the entrance of the channels. This can be monitored as increasing resistance to blood flow associated with a progressive decrease in mass transfer capacity. As the platelet aggregates grow bigger, the red cells are eventually caught and attached, resulting in the whole system becoming clogged.

In one preferred embodiment of the present invention, a device for effecting the chromatographic separation of at least two components of a sample comprises:

(a) a modified polysaccharide material in the form of one or more sheets, corrugated sheets, or tubes; and (b) means for effecting tangential flow of said sample across said modified polysaccharide material.

The matrix material within the tangential flow separation device may be in the form of sheets. For example, one or more sheets of matrix material may be positioned in parallel fashion with means to distribute blood at one end and collect blood at the other. The sheets may be self supporting or adhered to a rigid supporting member.

In this embodiment, a plurality of parallel plates having a layer of matrix material in the form of a sheet thereon may be stacked in a suitable housing with means to distribute and means to collect the sample. The layers may be separated by supporting means on the walls of said housing comprising grooves configured to accept the edge of said plates or may be separated by an array of filaments disposed parallel to one another and parallel to the direction of sample flow to provide channels for sample flow tangential to the media. The size of the filaments and their spacing can be optimized to provide high efficiency separations with minimal pressure differentials ($\Delta p$) between the inlet and outlet of the device. The thickness of the filaments and their spacing can be determined by one of ordinary skill in the art using routine testing. Optionally, the layers may be separated by two arrays of filaments disposed at oblique angles to one another. Advantageously, the two arrays of filaments are affixed at their crossover points.

The means for distributing and collecting the sample may comprise one or more grooves on the interior of two sides of the housing which are in fluid communication with said channels and nozzles disposed on each side of the housing. Alternatively, the matrix may be configured in the form of a corrugated sheet which provide channels without the use of filaments or nets.

In another embodiment, the matrix material may be configured into hollow tubes through which a sample, e.g., blood, can flow tangentially to the surface of the matrix. Advantageously, the matrix may form a layer of uniform thickness on the inner walls of an impermeable tube. This tube may then be coiled within a housing having means for introducing blood to the coil and means for collecting blood therefrom. Optionally, the housing may also contain means for regulating the temperature of the coil such as heaters, fans, thermostats, thermally regulated fluids, and the like. See U.S. Pat. No. 4,061,141 (1977) to Hyden et al.. which is incorporated by reference herein.

In a more preferred embodiment, the matrix is in the form of one or more sheets spirally wound around a cyclindrical core. In this embodiment, the separation device for effecting the chromatographic separation of at least two components of a sample flowing therethrough comprises:

(1) a cylindrical core,
(2) at least a first and second stationary phase wound around said cylindrical core, wherein,
  (a) said first phase comprises the modified polysaccharide matrix material of the invention; and
  (b) said second phase comprises a means for supporting, separating and providing channels tangential to said core,
(3) means for distributing the sample to said channels,
(4) means for collecting the sample from said channels, and
(5) a cylindrical housing.

The device may further comprise a third stationary phase disposed between the first and second phases comprising an impermeable sheet. This impermeable sheet may comprise any impermeable material compatible with blood and the matrix material including, but not limited to polyvinylchloride (PVC), polyethylene, etc.

The means for supporting and separating, and providing channels tangential to the cylindrical core, herein referred to as a mesh, net, or screen, may comprise two arrays of filaments including a first array spaced parallel to one another and to the axis of the cylindrical core and a second array of filaments spaced parallel to one another and perpendicular to the axis of said cylindrical core. Advantageously, the two arrays of filaments are affixed at their crossover points. The two arrays may be disposed perpendicular to one another or may be disposed at oblique angles, as long as one array is perpendicular to the axis of the cylindrical core. This type of screen or net provides a series of flow channels tangential to the cylindrical core.

The individual filaments may be round, square, rectangular or triangular in cross section. The thickness and spacing of the filaments may be readily determined by one skilled in the art by performing tests which vary the dimensions. Such factors as the spacing and thickness of the filaments are highly dependent on the type of media utilized, e.g. swellability, wettability, thickness, chemical composition, etc., the flow rate of the sample tangential to the stationary phase, the surface area of the stationary phse, e.g. number of windings, thickness of media, etc. and the type of sample chromatographed, e.g. blood or fermentation media. It is very difficult to clearly specify these variables, but may be determined by trial and error or by more elaborate testing procedures.

Preferably, the first array of filaments are round and are 9.5 mil and the second array of filaments are round and 47 mil.

The filaments of the first array may be disposed at an angle of about 49° to 90° relative to the second array of filaments. Most preferably, the first array is disposed at about a 90° angle to the second set.

Advantageously, the filaments may be made of polyethylene, polypropylene, polystyrene, nylon, or a substantially non-deformable yet resilient elastomer or metal. The material employed should be one which separates adjoining layers of matrix material or impermeable sheete without deformation, one which may be easily fabricated, and one which is not deleteriously affected by contact with the sample or matrix. Preferably, the filaments are constructed of polypropylene.

The means for collecting the sample may comprise one or more grooves along the entire length of the cylindrical core. These grooves are in fluid communication with the tangential flow channels and a nozzle disposed on the end of the cylindrical housing. The means for distributing the sample comprises one or more grooves along the length of the cylindrical housing which are in fluid communication with the tangential flow channels and a nozzle disposed on the cylindrical housing.

It is to be understood, of course, that the means for collecting the sample may be used for distributing the sample and the means for distributing the sample may be used for collecting the sample.

Figure 15A:
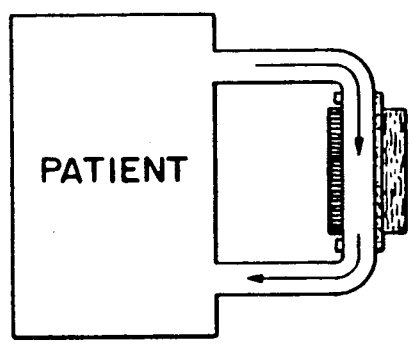
FIG. 15A depicts a cross section view of another embodiment of the invention which provides for tangential flow across two layers of chromatographic media.
Figure 15B:
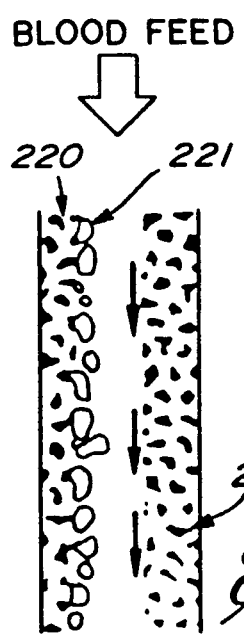
FIG. 15B depicts the blood feed through a tangential flow device having two layers of chromatographic media.
Figure 17:
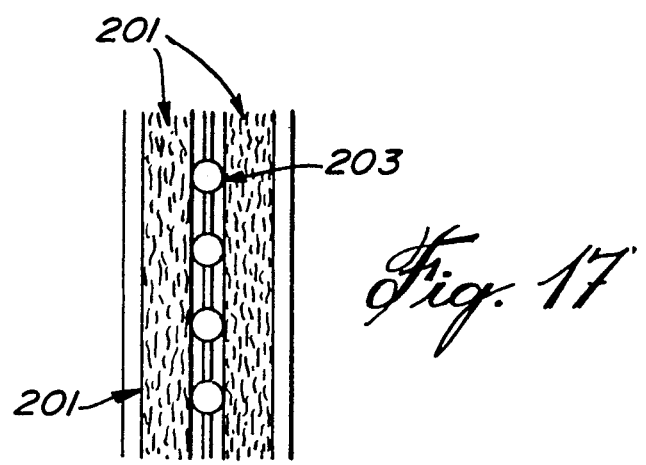
FIG. 17 depicts a cross-sectional view of one winding of the dual-layer tangential flow cartridge.
Figure 18:
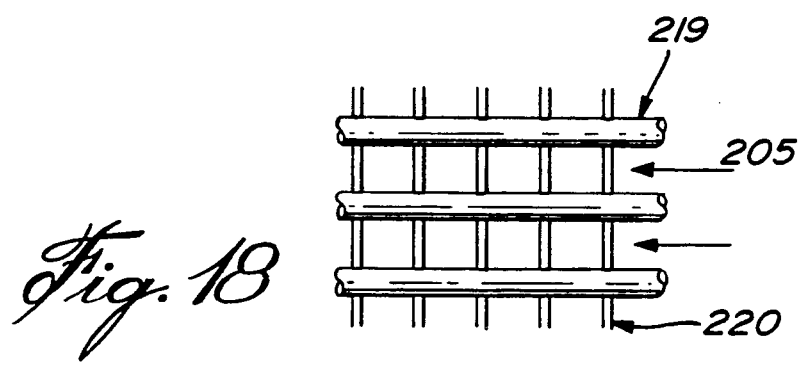
FIG. 18 depicts the sample flow relative to the supporting and spacing and channeling means.

As shown in FIG. 17, the device may comprise two sheets of matrix material 201 per winding so that the channel has a layer of matrix on each side. As shown in FIG. 15, the two sheets may comprise two different ligands. For example, one sheet of matrix 220 may absorb bacteria 221 or lipids preferentially and a second sheet of matrix 222 may comprise material which selectively adsorbs heparin.

Figure 12:
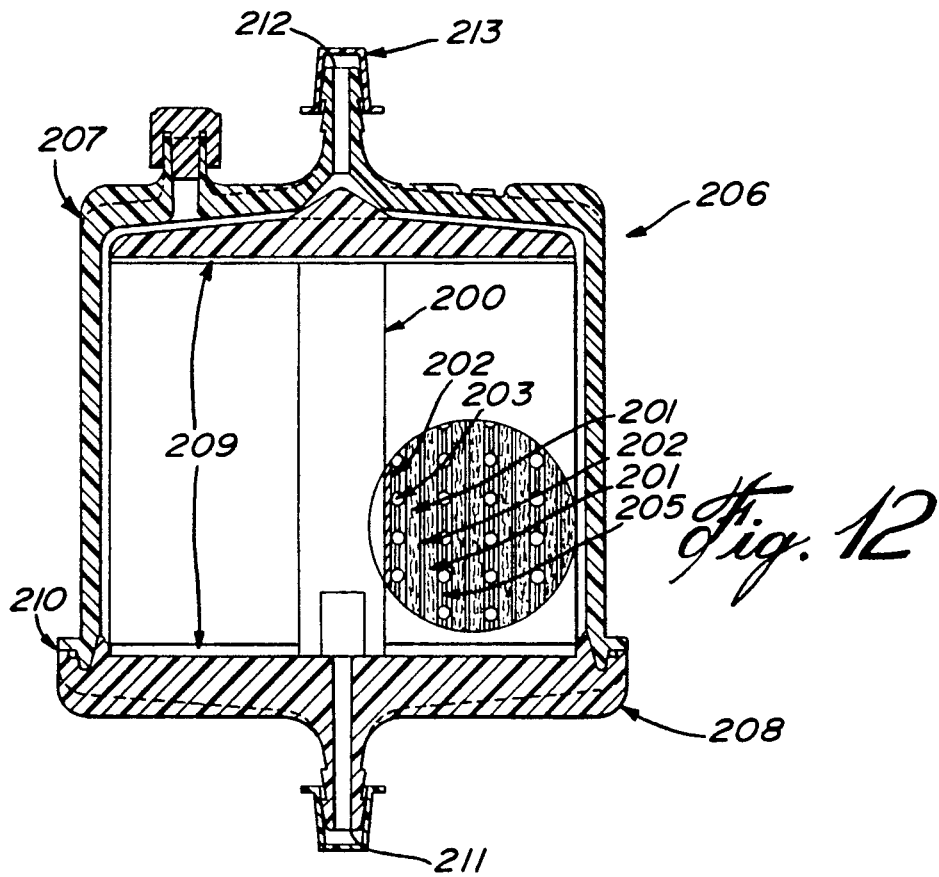
FIG. 12 is a cross-sectional view of one embodiment of a tangential flow cartridge within a cylindrical housing.

In one embodiment depicted in FIG. 12, the tangential flow column, which may be in cartridge form generally designated 206, is comprised of two layers spirally wound chromatographic media 201, spirally wound impermeable film 202 and spirally wound flow guidance web 203 around a cylindrical core 200. The housing 207 and outlet cap 208 contain the spirally wound device.

The spirally wound media, impermeable film and web 203 are sealed on each end 209 by thermoplastic plastic fusion using techniques described above. The outlet cap 208 and housing are held together by a weld 210. The housing also contains inlet and outlet means 211 and 212 which may be protected with a protective cap 213.

Figure 11:
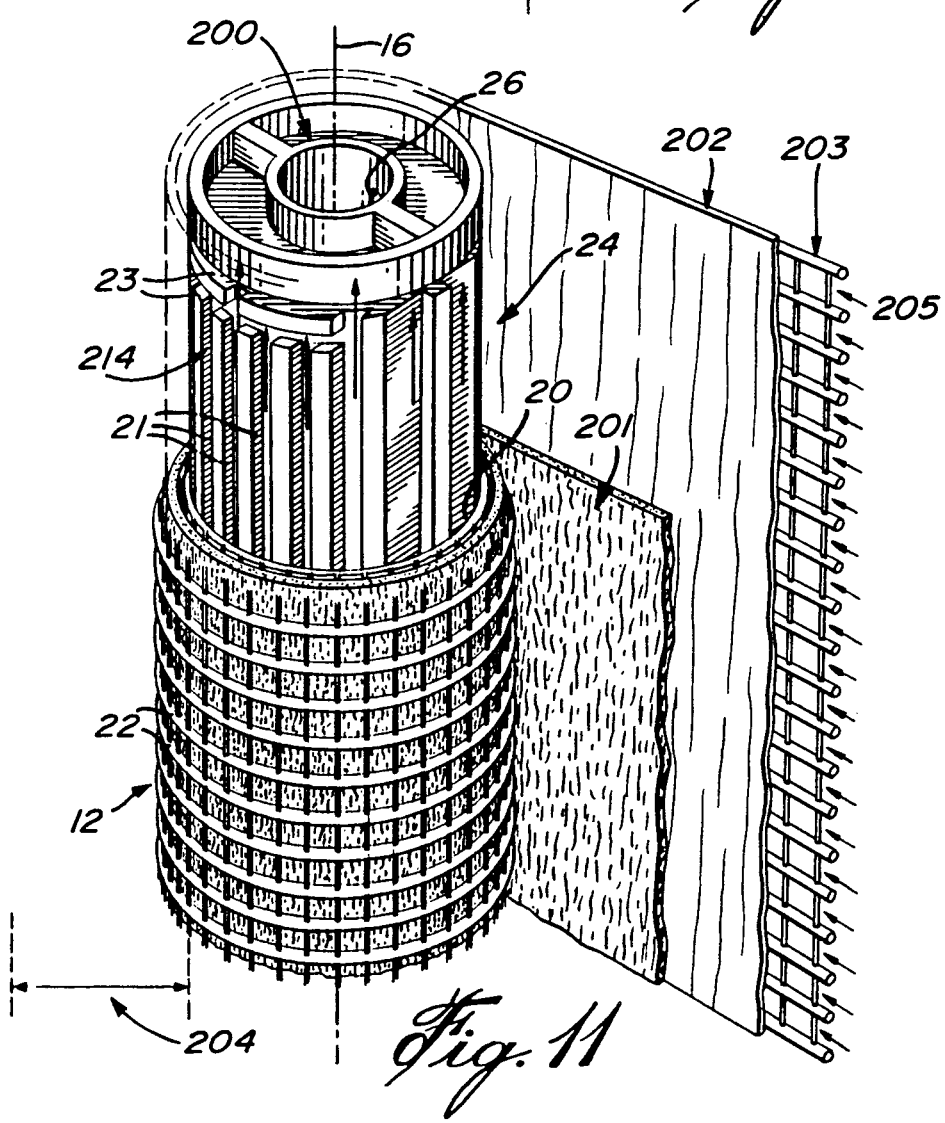
FIG. 11 is a perspective view of one embodiment of a tangential flow cartridge with a portion of the solid stationary phase broken away therefrom showing the spirally wound chromatographic media, spacer means, and impermeable membrane.

Referring to the embodiment depicted in FIG. 11, one layer each of chromatographic media 201, impermeable sheet 202 and flow guidance web 203 are wound around the cylindrical core 200. The sample flows tangential to the chromatographic media in the channels 205 and is collected by a series of grooves 214 in the cylindrical core 200 which are in fluid communication with the channels 205. The media, web and layer thickness 204 can be adjusted to achieve optimal flow rate, chromatographic efficiency and cell stability.

Figure 13A:
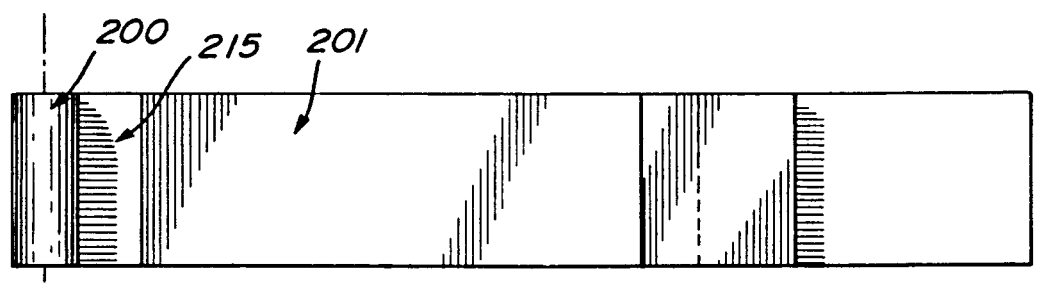
FIG. 13A depicts a top view of one method used for constructing the tangential flow cartridge.
Figure 13B:
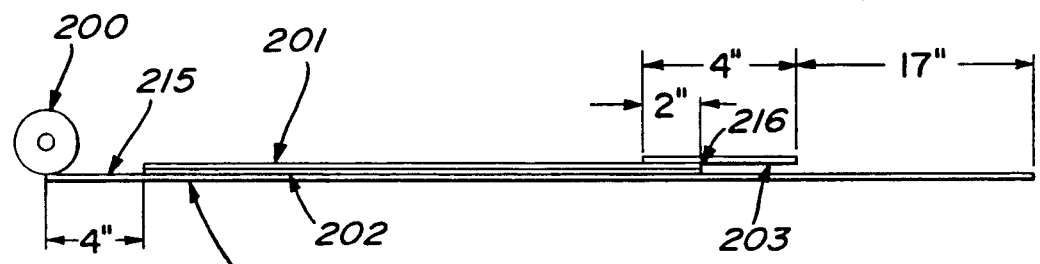
FIG. 13B depicts a side view of one method used for constructing the tangential flow cartridge.
Figure 14A:
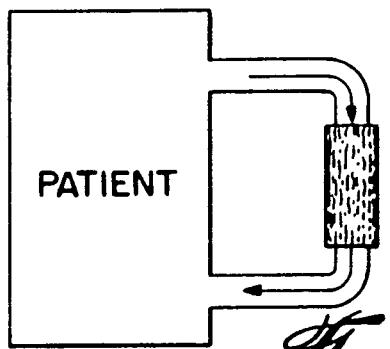
FIG. 14A depicts a schematic drawing of the blood flow from a patient through a radial flow device.
Figure 14B:
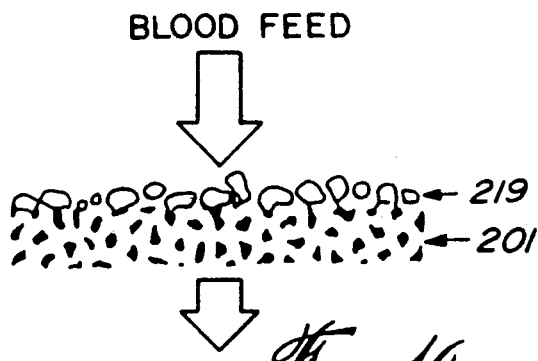
FIG. 14B depicts a schematic drawing showing the blood feed through a radial flow device.
Figure 14C:
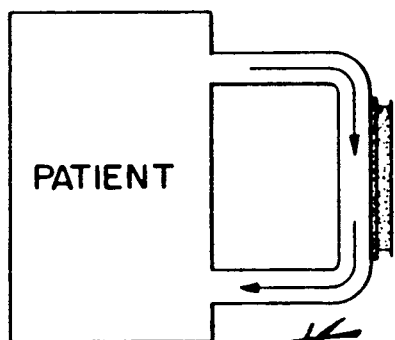
FIG. 14C depicts a schematic drawing of the blood flow from a patient through a tangential flow device.
Figure 14D:
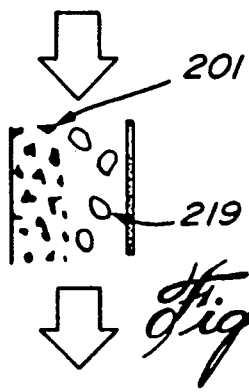
FIG. 14D depicts the blood feed through a tangential flow device.

Referring to FIG. 13, the tangential flow cartridge having one layer of chromatographic media 201 is prepared by layering media 201 and impermeable film 202 onto the webbing 203, wherein one end 215 of the webbing 203 is not covered by media 201 or film 202. The opposite end of the media 216 has an additional layer of webbing 203 layer on top and extending beyond the layer of media 201. The media 201, film 202 and webbing 203 are then wound around the cylindrical core 200.

Figure 16:
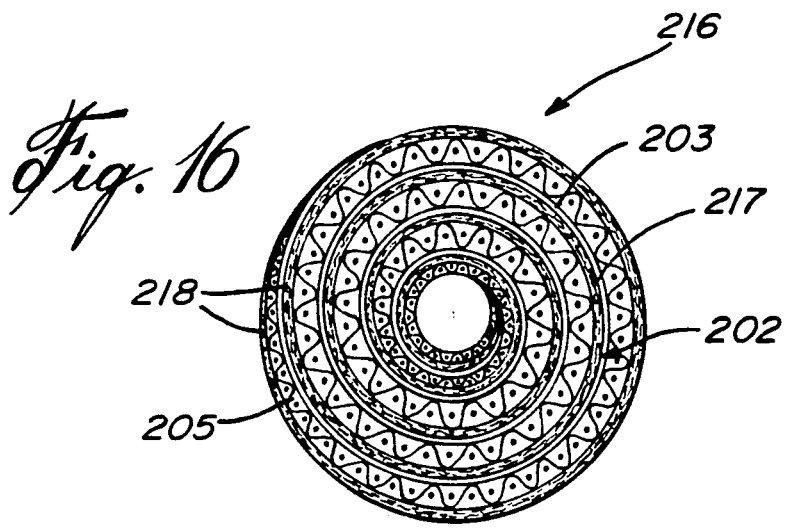
FIG. 16 depicts a top plan view of the tangential flow cartridge having dual layers of chromatographic media.

FIG. 16 depicts a top plan view of the tangential flow cartridge having an impermeable sheet 202, a web as flow channel guidance 203 which may also have a layer of PHMA 216, a highly hydrophilic layer to promote protein migration and an HDA, a pyrogen or bacteria adsorption layer 217. The sample is delivered to the channels 205 defined by the web at the blood flow inlet 218.

USES

The affinity, reverse-phase, or bioactive materials of the invention can be used in any of the well known prior art processes of affinity or reverse-phase chromatography, or as supports for bioreactors.

The materials obtained in the present invention have unique properties over materials used heretofore. A binary system formed by mixing modified polysaccharide, e.g., cellulose, with other types of polysaccharide, such as microcrystalline cellulose, and forming a fibrous sheet (without the addition of extra particulate material) has the advantage of lacking silica materials, which normally shows nonspecific adsorption of proteins. The absence of any substantial swelling or a highly controllable degree of swelling which can be readily controlled by adjusting the multiple variables present in the system, allows the replacement of unmodified microcrystalline cellulose by other mechanical strengtheners, has low production cost, and high exchange capacity or anchoring capacity, which can, in any event, by modified by controlling various conditions, including the ratio of comonomers (a) and (b).

A ternary system formed from modified polysaccharide, modified or unmodified particulate and unmodified fibers has the advantage of potential maximization of swelling, rigidity and capacity obtainable through varying the multiple variables present in the system. Flow rates can be controlled by varying the ratio of organic to particulate (especially silica) components without significant loss of capacity. In addition, such a system shows advantages over prior art systems using nonmodified celluloses in that, in many instances, no refined pulp is necessary, since the polymer linked on the polysaccharide will function as well as refined pulp in bridging particles to the fiber surfaces. The polymeric components in the present system may also function as binder resins; therefore, addition of resins to the slurry can, if desired, be eliminated.

While ordinarily the prior art has relied on materials with high surface area to bind the maximum number of chemical groups thereon, the materials of the present invention provide means of binding multifunctional groups per each polysaccharide molecule. As long as these functional groups are made accessible for anchoring, the preparation is no longer limited to high surface area materials.

In protein separation and purifications, the key factor which ought to be avoided is possible damage to the protein molecules. In the present invention, this is avoided by using biocompatible materials such as polysaccharides with only limited amounts of organic polymers. The materials are swellable and provided for very little denaturation of protein. Nonspecific adsorption of biopolymers is decreased, since both acrylic and saccharide polymers show very low amounts thereof, and are hydrophilic in nature.

With regard to samples containing cells, e.g. blood or fermentation media, lysis of cells can be avoided by passing the sample through a cartridge configured so that the sample flows tangentially, but not through, the matrix material. Thus, the tangential flow cartridge may be used to separate or purify, components of blood or fermentation media. For example, the matrix may comprise a celluloseacrylate bi-component composite polymer with aldehyde groups extended on a spacer arm for coupling chemical or biological ligands for the separation of the components of a sample. Such biological ligands include, for example, anti-coagulant adsorption ligands which allow removal of citrate-phosphate-dextrose (CPD), a commonly used anti-coagulant, or heparin from the blood. Three ligands in particular, Ligand A (low molecular weight amino compound comprising hexamethylenediamine), Ligand B (protamine) and Ligand C (high molecular weight amino polymer comprising polyethyleneimine) have particularly been found useful for the adsorption of anti-coagulants. The ligands comprising amino groups are attached to the matrix material as described above.

Another area of design flexibility and design control is in the possible adjustment of the length of the acrylic polymer carrying the various anchoring groups. The variability of the polymer length no only may eliminate steric hindrance due to solute or ligand accessibility, but also minimizes leakage of the ligand from the matrix. The polymer "arm" should not be too long to avoid potential internal hydrophilic interaction, such as folding back. An "arm" of about 5 to 20 atoms is generally ideal for attaching the bioligands.

By the use of well known anchoring groups for affinity ligands or biomolecules, the materials can incorporate all of the synthetic methods developed in prior art commercial materials, such as Sephadex$^R$ or Sepharose$^R$.

Finally, the matrix is chemically and physically stable with minimum change of dimensional stability upon contact with salt and eluants.

EXAMPLES

Having now generally described this invention, the same will be better understood by reference to certain specific examples which are included herein for purposes of illustration only, and are not intended to be limiting of the invention unless otherwise specified.

EXAMPLE 1

Preparation of an Affinity Chromatography System

Component A: cellulosic fiber
Component B: glycidyl methacrylate
Component C: mono or di-saccharide

Method A

Step 1. Coupling of C to B

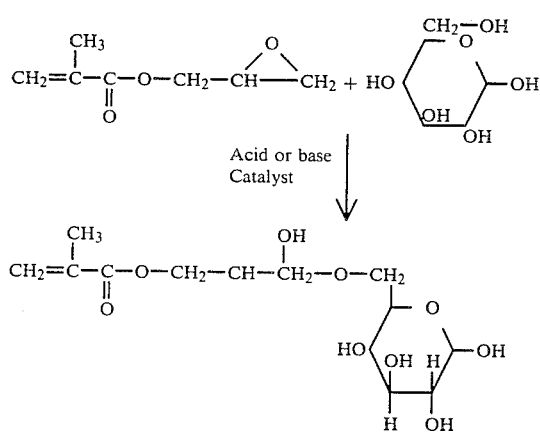

Step 2. Formation of Polymers with Controlled Ratio of B to BC

| Component B | (10%) | polymerization by Redox catalyst | Copolymer of 10% B & 90% BC |
|---|---|---|---|
| Component BC | (90%) | | |

Step 3. Coupling of the Above Copolymer to Component A

With excess amount of catalyst left in Step 2, the epoxy groups in Component B of the above copolymer can be coupled to cellulose, by raising the temperature to 90° C. The chemical reaction is exactly the same as Step 1, except that the Component A is in polymeric form whereas Component C is a monomer.

Method B

Step 1. Formation of Acrylic Copolymer

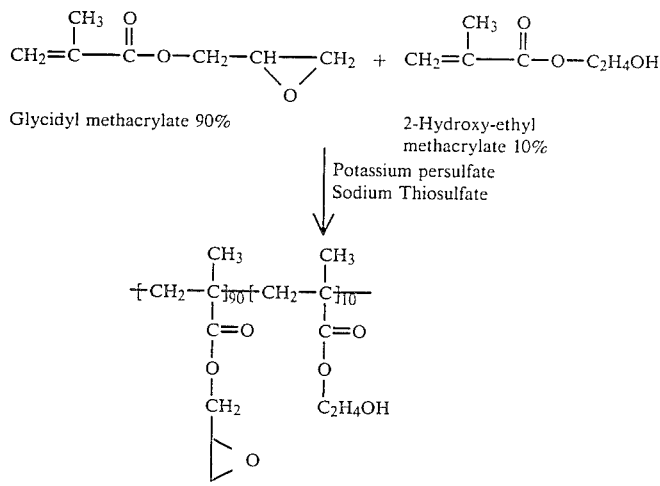

Step 2. Component C is added to the polymer on a proper molar ratio such that 90% of the available epoxy groups will be reacted with C under acid or base catalytic conditions. The remaining 10% will be left available for coupling onto the cellulose surface afterwards.

EXAMPLE 2

Cellulose Grafted with Polymethacrylic Acid (a) Recipe

| Reagent | Quantity |
|---|---|
| Cotton linter fiber | 36 g |
| Methacrylic acid (or B-carboxyethyl acrylate) | 90 ml |
| Glycidyl Methacrylate | 9 ml |
| Triton X-100 | 2.0 g |
| Sodium Lauryl Sulfate | 1.5 g |
| Ammonium persulfate | 3.6 g |
| Sodium Thiosulfate | 3.6 g |
| Tributyl Amine | 1.0 ml |

Examples 3 and 4 are directed to the formation of the pre-ligand matrix; Example 5 is directed to the coupling of the benzamidine ligand.

EXAMPLE 3

Preparation of Cellulose-GA Pre-Ligand Affinity Matrix (a) Formulation

| Reagent | Quantity |
|---|---|
| Refined cellulose | 5.0 g |
| Glycidyl acrylate | 10.0 ml |
| Ethoquad C/25 | 0.5 ml |
| APS | 0.5 g |
| STS | 0.5 g |
| 1.0M HCl | 16.67 ml |
| D.I. H$_2$O | 250 ml |

(b) Process

The cellulose was dispersed in the 250 ml of D.I. H$_2$O with agitation at 80° C. and the glycidyl acrylate added to the reactor. Temperature and agitation were maintained, the APS, STS and HCl added, and the reaction permitted to proceed for one hour. The covalently-bonded cellulose-GA pre-ligandized matrix was removed, washed with 7×2 liters of deionized water and stored for further treatment (conversion to affinity ligand as in Example 5 below).

EXAMPLE 4

Preparation of Cellulose-GMA Pre-Ligand Affinity Matrix (a) Formulation

| Reagent | Quantity |
| --- | --- |
| Refined cellulose | 5.0 g |
| Glycidyl methacrylate | 12.5 ml |
| APS | 0.5 g |
| STS | 0.5 g |
| D.I. H$_2$O | 250 ml |

(b) Process

The cellulose was dispersed in the D.I. H$_2$O with agitation and heated to 80° C., with agitation. The glycidyl methacrylate, APS and STS were added to the reactor and the reaction permitted to proceed for one hour. The reaction was terminated and the covalently bound GMA-cellulose matrix removed, washed with 5×1.8 liters of D.I. H$_2$O and stored for further processing (conversion to affinity ligand as in Example 5 below).

EXAMPLE 5

Preparation of Affinity Matrix with Benzamidine Ligand

The GMA-cellulose matrix of Example 4 was washed with five volumes of deionized H$_2$O. The washed GMA-cellulose matrix was treated with a 1.5% aqueous solution of NaIO$_4$ at room temperature, five volumes of the NaIO$_4$ solution circulated through the matrix for 1 to 2 hours at room temperature. The resulting matrix, the epoxy groups now converted to aldehyde groups by the NaIO$_4$ solution, was washed with 10 volumes of deionized water at 25° C. and equilibrated with 0.01 M phosphate buffer at pH 7.8. Benzamidine in a concentration of 20 mg/ml was circulated through the aldehyde-pendant matrix at a flow rate of 2 cc/min overnight at 4° C. in the presence of NaCNBH$_3$, concentration approximately 1 mg/ml. Alternatively, the coupling of benzamidine may be effected at room temperature by circulating the above benzamidine solution at room temperature for 8 hours. Following coupling, any uncoupled protein was removed from the matrix by washing with phosphate buffer at pH 7.8. Any remaining aldehyde groups were deactivated by circulating glycine ethylester at pH 6.5 in the presence of NaCNBH$_3$ for four hours, the glycine ethylester produced by dissolving 1 g of glycine ethylester hydrochloride in 100 cc of deionized water, the pH adjusted to 6.5 by addition of sodium hydroxide solution.

EXAMPLE 6

Invention Media Containing Hydrophobic Groups (a) Recipe

| Poly (n-Ocylacrylate)-g-Cellulose | |
| --- | --- |
| Reagent | Quantity |
| Refined pulp (+260) | 20 g |
| n-octyl acrylate | 50 ml |
| Glycidyl methacrylate | 5 g |
| Ammonium persulfate | 2 g |
| Sodium thiosulfate | 2 g |
| Water | 933 ml |

(b) Procedure

1. Refined pulp (+260) as well dispersed in water in a 3 neck, 3 liter round flask.
2. n-Octyl acrylate and glycidyl methacrylate were well mixed before pouring into the reactor.
3. After pouring monomers into the reactor and mixing the reaction mixture well, ammonium persulfate and sodium thio-sulfate solutions were charged into the reactor at room temperature.
4. The reaction mixture was strongly agitated and the reaction temperature was raised to 82° C. within 15 minutes.
5. Stirring was maintained for 1 hour in the temperature range of 80°–85° C.
6. After cooling down the reaction mixture, the product was washed well with water.

EXAMPLE 7

Invention Media Containing Chelating Groups

Poly(3-N,N-dicarboxymethyl-2-hydroxy-propyl methacrylate)-g-cellulose (a) Recipe

| Reagent | Quantity |
| --- | --- |
| Refined pulp (+260) | 5.0 g |
| Glycidyl methacrylate | 12.5 ml |
| Ammonium persulfate | 0.5 g |
| Sodium thiosulfate | 0.5 g |
| Sodium imminodiacetate | 2 g |
| Water | 150 ml |

(b) Procedure

1. Refined pulp (+260) was well dispersed in 800 ml water in a 3 neck reactor.
2. After pouring glycidyl methacrylate into the reactor and mixing the reaction mixture well, ammonium persulfate and sodium thiosulfate were charged into the reactor at room temperature.
3. The reaction mixture was strongly agitated, and the reaction temperature was raised to 80° C. within 15 minutes.
4. Stirring was maintained for 1 hour in the temperature range of 80°–85° C.
5. The reaction mixture was cooled to 60° C., and then sodium iminodiacetate was charged into the reactor. Further reaction was continued for 26 hours.
6. The reaction mixture was cooled, and product was filtered and washed.

EXAMPLE 8

Immobilization of Protein A For Gammaglobulin Purification

Protein A is a cell-wall protein which can be isolated from *Staphylococcus aureus*. Its rather unique reactivity directed to the F$_c$ region of IgG makes protein A a powerful bioligand for the selective removal of IgG from normal or immune sera. Immobilization of protein A to a solid support has been studied to isolate whole IgG or individual subclasses, to separate cells or to remove immuno-complex from plasma as a means of immunotherapy.

(a) Materials and Methods

Either high purity natural or recombinant Protein A may be employed. Recombinant Protein A was purchased from Repligen with the following physicochemical properties. The purity is greater than 98% by TSK-3000 HPLC assayed at 214 nm and greater than 94% pure at 280 nm. A single major band is produced by SDS-PAGE at approximately 45,000 MW+1,000. It has an extinction coefficient at 0.1% of 0.16+0.02 at 270 nm. The IgG binding activity is greater than 95% as determined by the percentage of total protein bound to an immobilized human IgG column when assayed by Lowry.

Structure studies carried out on recombinant Protein A by Repligen indicated the DNA sequence derived position of the four homologous $F_c$ binding domains D, A, B and C originally described.

(b) Media Preparation

The composite media prepared according to Example 4 was prepared by grafting to cellulose, with cellulose serving as solid support and GMA or GA polymers providing the chemical functional groups for coupling. Two types of affinity matrix were then prepared. Type A carried amino groups and used glutaraldehyde for protein coupling; Type G carried hydroxy groups requiring periodate oxidation for the formation of aldehyde as a means of protein coupling.

PROTEIN A-COUPLING

The amino groups were introduced to the matrix by covalently linking 1,6-diamino hexane to the glycidyl groups of the matrix. The total amino groups titrable from the potentiometric titration with 0.1 N hydrochloric acid was about 1.8 meg per gram of dry matrix. The matrix carrying amino groups was equilibrated with 0.1 M sodium phosphate, pH 7.3, as activation buffer, followed by recirculation of 10% glutaraldehyde in the same buffer at room temperature for 6 hours in the presence of 1.0 mg/ml sodium cyanoborohydride. Excess amount of glutaraldehyde was removed by rinsing the matrix with activation buffer until the eluate showed its absence from the Schiff reagent solution. The matrix carried active aldehyde groups in the following form and was ready for Protein A coupling through its amino groups.

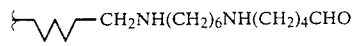

Protein A solutions were prepared at 10 mg/ml in 0.1 M sodium phosphate pH 7.3, and recirculated in the presence of (1.0 mg/ml) sodium cyanogen borohydride for 16 hours at room temperature; the uncoupled ligand was removed by rinsing the matrix with buffer solution until the ligand was no longer detectable in the eluate. The excess amount of active groups was deactivated by recirculating 1% glycine ethylester hydrochloride in 0.1 M sodium phosphate pH 6.5 as blocking buffer for 4 hours. Then the matrix was rinsed with any desired buffer containing 0.25 M NaCl, followed by the equilibration buffer that was to be used when performing the affinity step.

(c) Measurement of Ligand Coupled to Cartridge

The amount of ligand coupled to the cartridge was determined by doing a Lowry protein assay of the dialyzed uncoupled ligand and subtracting this value from the amount of Protein A given.

PROCEDURE FOR IgG PURIFICATION

The cartridge was equilibrated with 50 mM NaP, pH 7.6+250mM NaCl. A human gammaglobulin (HGG) solution (Sigma G-4386), approx. 2.5 mg/ml in the above buffer, was passed through the cartridge either in a single pass or with recirculation. The unbound gammaglobulins were then washed from the matrix with the above buffer. The bound gamma-globulins were eluted from the matrix with a 0.2 M Gly-HCl pH 2.3 buffer. The amount of HGG bound was determined by $OD_{280}$ of the elution. The matrix was then re-equilibrated with the pH 7.6 buffer and it was ready for another sample.

(d) Spacer Arm Length and HGG Binding

The effect of varying the spacer arm length was studied by conjugating protein A using hexamethylene diamine (21°A, Sample Nos. 1–3), ethylene diamine (16°A Sample Nos. 4–6), and epoxy by periodate (6.0°A, Sample Nos. 7–9), measuring the amount of Protein A coupled, binding HGG, measuring the amount of HGG bound, and determining HGG-Protein A binding ratios. The results are shown in Table IV.

TABLE IV

EFFECT OF SPACER ARM LENGTH ON HUMAN GAMMAGLOBULIN BINDING BY PROTEIN A AFFINITY MATRIX

| Sample No. | Estimated Spacer Arm Length (°A.) | Method of Coupling | Amount of Protein A Coupled (mg/g Media) | Amount of HGG Bound (mg) | HGG Protein A (mg/ml) |
|---|---|---|---|---|---|
| 1. | 21° A. on hexamethylene diamine and glutaraldehyde | Schiff base formation | 0.8 | 5.2 | 6.5 |
| 2. | 21° A. on hexamethylene diamine and glutaraldehyde | | 4.6 | 12.0 | 2.4 |
| 3. | 21° A. on hexamethylene diamine and glutaraldehyde | Schiff base formation | 9.2 | 14.0 | 1.4 |
| 4. | 16° A. on ethylene diamine and glutaraldehyde | Schiff base formation | 0.9 | 6.0 | 6.6 |
| 5. | 16° A. on ethylene diamine and glutaraldehyde | Schiff base formation | 4.6 | 12.0 | 2.6 |
| 6. | 16° A. on | Schiff base | 9.2 | 14.0 | 1.5 |

TABLE IV-continued
EFFECT OF SPACER ARM LENGTH ON HUMAN GAMMAGLOBULIN BINDING BY PROTEIN A AFFINITY MATRIX

| Sample No. | Estimated Spacer Arm Length (°A.) | Method of Coupling | Amount of Protein A Coupled (mg/g Media) | Amount of HGG Bound (mg) | HGG Protein A (mg/ml) |
|---|---|---|---|---|---|
| 7. | ethylene diamine and glutaraldehyde 6.0° A. | formation Aldehyde formed through epoxy oxidation by periodate | 0.8 | 2.4 | 3.0 |
| 8. | " | | 3.4 | 3.8 | 1.1 |
| 9. | " | | 7.8 | 6.4 | 0.8 |

EXAMPLE 9

Immobilization of Antibody or Antigen on Affinity Matrix

By following the procedure of Type A (amino groups) media with glutaraldehyde as the coupling group, Protein A was immobilized to the matrices of Examples 4, 5 and 8 and tested for its capacity for binding of HGG. The results are shown in Table IV.

For a demonstration of the effect of types of media and methods of coupling on the performance of immobilized bio-molecules, Goat anti-HGG was immobilized on type G matrices by forming aldehyde groups through periodate oxidation, with the results shown in Table V.

equilibrated with 50 mM NaP, pH 6.2, +0.25 M NaCl.

(2) 10% glutaraldehyde solution (in above buffer) was recirculated for 5 hours (133 mls).

(3) Cartridges were washed with above buffer.

(4) 6.4 grams of PAB and 6.4 grams of STI were recirculated through their respective cartridges overnight (640 mls of above buffer+0.2% HaCNBH$_3$).

(5) Cartridges were washed well using above buffer and 0.2 M Gly-HCl, pH 2.3, alternately.

(6) Cartridges were deactivated with 1% glycine ethyl ester.

(b) Testing Procedure (1) 4 liters of a Trypsin solution (Porcine Pancrease

TABLE V
PERFORMANCE OF GOAT ANTI-HGG IMMOBILIZED BY PERIODATE OXIDATION ON AFFINITY MATRICES

| Matrix Type | Matrix Weight (in 13 mm Column) | Goat Anti-HGG (4.3 mg/mg) Applied | Coupling Conditions | Amt. Coupled & Efficiency | HGG Capacity | Goat Anti-HGG HGG | Ab Ag |
|---|---|---|---|---|---|---|---|
| Type G groups | 1.00 g | 2.5 mg | 4° C. overnight PBS (.05M) pH = 7.6 | 2.48 mg 99% | 1.06 | 0.43 | |
| Type G groups | " | 5.0 g | 4° C. overnight PBS (.05M) pH = 7.6 | 4.93 mg 99% | 0.83 mg | 0.17 | |
| Type G groups | 1.02 | 10.2 mg | 4° C. overnight PBS (.05M) pH = 7.6 | 9.86 mg 96% | 1.68 mg | 0.17 | |
| Type G groups | " | 15.30 mg | 4° C. overnight PBS (.05M) pH = 7.6 | 13.76 mg 90% | 2.64 mg | 0.19 | |
| Type G groups | 1.03 g | 20.60 mg | 4° C. overnight PBS (.05M) pH = 7.6 | 16.81 mg 82% | 3.11 mg | 0.19 | |
| Type G groups | 1.04 g | 23.71 mg | 4° C. overnight PBS (.05M) pH = 7.6 | 18.81 mg 79% | 3.52 mg | 0.19 | |

In this case, Goat Anti-HGG was the immobilized antibody to interact with HGG as the antigen. The bound antigen were eluted by 0.2M glycine-HCl at pH 2.3 from the column in purified form.

EXAMPLE 10

Immobilization of p-Aminobenzamidine (PAB) Soybean Tryosin Inhibitor (STI) on Type A Matrix Affinity (a) Coupling Procedure:

(1) Matrices prepared according to Examples 1, 4, and 8, in radial cartridge form, were washed and Trypsin, Sigma) in 50 mM NaP, pH 7.6, +25D mM NaCl buffer was passed through each cartridge at two different flow rates. Fractions were collected.

(2) The cartridges were eluted with 0.2 M Gly-HCl, pH 2.3

(3) Protein was detected b OD$_{280}$.

(4) Trypsin activity was detected by assaying with Kabi colorimetric substrate S-2302.

1 unit of trypsin act=OD$_{405}$ of 1.0/ml/min.

(5) The results are shown in Tables VI (PAB) and VII (PAB and STI).

Enzyme activity measurement
The enzymatic activity was determined by the kinetic

TABLE VI
IMMOBILIZATION OF PAB LIGAND ON AFFINITY MATRIX TYPE G FOR TRYPSIN PURIFICATION

| SAMPLE NO. | PAB Coupled (mg) | Trypsin Eluted (mg) | Units Eluted (Activity) | Units g media | Units mg PAB | Protein Recovery (%) Total | Activity Recovery (%) | mg Trypsin mg PAB |
| --- | --- | --- | --- | --- | --- | --- | --- | --- |
| 1. | (i) 52.82 (ii) 12.9 mg/g | 67.5 | 8193 | 2003 | 155 | 89 | 91 | 1.278 |
| 2. | (i) 49.1 (ii) 12.46 mg/g | 71.7 | 9068 | 2302 | 185 | 90 | 97 | 1.46 |
| 3. | (i) 73.9 (ii) 13.58 mg/g | 95.5 | 11350 | 2086 | 154 | 85 | 94 | 1.222 |
| 4. | (i) 66.5 (ii) 11.40 mg/g | 91.7 | 11461 | 1966 | 172 | 85 | 98 | 1.379 |

Tested in 60 mm size disks with 5.0 gram media weight.

TABLE VII
IMMOBILIZATION OF PAB AND STI FOR TRYPSIN PURIFICATION

| | mg. Ligand Coupled | Flow rate of test | mg Trypsin eluted | Units Trypsin eluted | Units/ gram media | Units/mg coupled ligand | % Protein recovery | % Activity recovery | mg Trypsin mg coupled ligand |
| --- | --- | --- | --- | --- | --- | --- | --- | --- | --- |
| PAB COUPLED CARTRIDGE (containing 128 gram of media) | 1257.7 mg/min | (1) 83 mls/min | 2035 mg | 152874 units | 1194 | 121.6 | 91% | 108% | 1.62 |
| | 9.8 mg/min | (2) 295 mls/min | 1887 mg | 140464 units | 1097 | 111.7 | 93% | 120% | 1.50 |
| STI COUPLED CARTRIDGE (containing 128 gram of media) | 20687 mg | (1) 84 ml/min | 1663 mg | 230128 units | 1798 | 111.2 | 90% | 122% | 0.80 |

EXAMPLE 11

Immobilization of Glucoamylase Enzyme on Affinity Cartridge for Beverage Processing Immobilization of glucoamylase has already been applied in the industrial production of fructose syrup from starch. The preparation used in the large-scale production of glucose was obtained by the covalent binding of enzyme by means of glutaraldehyde to porous inorganic materials containing primary amino groups. However, in the case of glucoamylase removal from beer, the silica type of inorganic material will affect the flavor and color of the beer due to the ionization of silica under low pH to silicic acid on solid surfaces. Cellulosic substrates, being inert and nonionizing, stand out as being more favorable for beverage purification and separation.

Methods and Materials

Raw material

Glucoamylase (α-1,4-glucan glucohydrolase, EC 3.2.1.3), purchased from Sigma Chemical Co., St. Louis, MO, is obtained from strains of *Aspergillus oryzae*. The enzyme has a molecular weight between 48,000 to 80,000 and usually has no subunit structure. The carbohydrate content of the enzyme ranges from 3% to 30% containing mainly mannose, but glycose, galactose, and, in some instances, glucosamine and xylose are also present. The carbohydrate structure is present as mono-, di-, tri-, and tetrasaccharide units linked O-glycosidically through mannose to the hyroxyl groups of serine and threonine. The isoelectric point is between 3.9 and 5.5, and has a pH optima of 5.0 to 5.5 determination of the amount of glucose released from starch versus time by glucoamylase. The glucose production was measured utilizing an assay system purchased from Sigma Chemical Company (Stock No. 15-10) and described in Sigma Technical Bulletin Co. 15 UV. The change in glucose production is measured as a change in optical density at 340 nm per minute on a Cary 210 spectrophotometer.

Principle of glucose assay

The analysis is based upon the conversion of glucose to glucose-6-phosphate by ATP in the presence of hexokinase, coupled with the subsequent reduction of NADP to NADPH. As NADPH has a high absorbance at 340 nm ($A_{340}$) and NADP has no absorbance at this wavelength, the reaction can be followed by measuring the increase in $A_{340}$. The increase in $A_{340}$ due to formation of NADPH is directly proportional to the amount of glucose present.

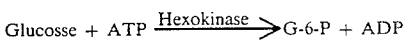

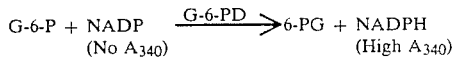

Definition of enzyme activity unit

One unit will liberate 1.0 mg of glucose from starch in 3 min at pH 4.5 at 55° C.

EXAMPLE 12

Glucoamylase Immobilization on Type A Affinity Matrix

Type A matrix prepared according to Examples 4 and 8 is a 12-atom spacer amino matrix which can be activated by glutaraldehyde to make it suitable for enzyme immobilization according to the mechanism shown above.

(a) Procedure of coupling
1. The matrix was washed with 50 ml of deionized water;
2. Equilibrated with 50 ml 0.05 M phosphate buffer +0.25 M NaCl, pH 7.5, at room temperature;
3. Activated by recirculating 50 ml 1.0% glutaraldehyde in the buffer at room temperature;
4. Excess glutaraldehyde was removed by washing with the above buffer twice;
5. The ligand (10 mg/ml in same buffer) was coupled overnight at room temperature in presence of *$NaBH_4$ (usually 1 mg/ml $NaBH_4$ is used); *1 g of glycine ethylester hydrochloride is dissolved in 100 ml of phosphate buffer; final pH is adjusted to 6.5 Then $NaBH_4$ is added to make concentration 1 mg/ml.
6. The uncoupled ligand was washed off with same buffer until base line was obtained; and
7. Excess active groups were deactivated by circulating the glycine ethylester hydrochloride at pH 6.5 in the presence of $NaBH_4$ for about 4 hours at room temperature;
8. Excess reagents were washed off with the same buffer;
9. The amount of ligand coupled to the column was determined by nitrogen analysis.

(b) Procedure of measurement

The activity of glucoamylase samples was determined using a 1% solution of Amylopectin (Sigma No. 1-8515) in 0.2M sodium acetate pH 4.5. To 1 ml of this substrate 0.25 ml of sample was added at Time O in a 55° C. water bath. After 10.0 minutes, 1.25 ml of 0.2M potassium phosphate buffer pH 7.5 was added. A 40 μl aliquot of this solution was then added to 3.0 ml of reconstituted Sigma Glucose Assay No. 15-UV, and after a 5-minute incubation, the $A_{340}$ was recorded. Appropriate test blanks were subtracted from the absorbance reading to determine $A_{340}$, and from the $A_{340}$ sample activity in units was calculated.

(c) Procedure for enzyme activity test
1. Approximately 1 g of above-prepared matrix was suspended in 10 ml of 0.2 M sodium acetate buffer pH 4.5.
2. Suspension was vortexed, then centrifuged 10 min×2600 rpm.
3. Supernatant was decanted.
4. 0.2 g of the pellet was added to 1.0 ml 1.0% Amylopectin to determine the enzyme activity of the matrix by the method described above.

(d) Results

TABLE VIII

| Sample No. | Vol. of 1% Amylopectin Added | 0.2 M KPB pH 7.5 Added | $A_{340}$ Reading | Total Activity (Units) | Specific Activity of Coupled Enzyme: Unit/g Matrix |
|---|---|---|---|---|---|
| Blank 0.25 ml | 1.0 ml | 1.25 ml | 0.0 | | |
| #1 0.2 g matrix | 1.0 ml | 1.25 ml | 0.145 | 0.243 | 24.3 |
| #2 0.2 g matrix | 1.0 ml | 1.25 ml | 0.139 | 0.229 | 22.9 |
| #3 0.2 g matrix | 1.0 ml | 1.25 ml | 0.121 | 0.200 | 20.0 |

EXAMPLE 13

Heparin Removal by Amino-Hexyl and Protamine Media

1. Material Preparation

Coupling protamine to PHMA media; 10 ml (0.5 g of media) and 100 ml size (5 g of media) radial cartridge configuration.

PHMA is polyhyroxyl methacrylate prepared by acid hydrolysis of GMA to convert glycidyl into hydroxyl groups as demonstrated above. The conditions for activating PHMA for ligand coupling are as follows:
a. wash cartridges with 2 liters $H_2O$
b. activated with 1.5% $HaIO_4$ (in $H_2 0$) for 60 mins
c. wash with $H_2O$
d. equilibrate cartridge with 0.1M borate buffer (pH 8.2)
e. recirculate 42 mls of a 10 mg/ml solution of protamine in above buffer (Sigma No. P-4005 protamine, free base, from Salmon Sperm Grade IV) for 4 hrs at 15 mls/min
f. wash cartridge with 0.1M borate buffer pH 8.2 (save wash to determine amount of coupled protamine)
g. recirculate 100 mls of a 15% amine solution (either ethanolamine or diethylaminopropylamine) in the pH 8.2 buffer at 15 mls/min for approximately 20 hrs with 4×500 mg $NaBH_4$ additions
h. wash cartridge with 1 liter solution of:
  (1) 0.1M borate buffer, pH 8.2
  (2) 0.15M NaCl pH 2.7 (pH dropped with HCl)
  (3) 0.05M NaP+0.25M NaCl pH 7.6
  (4) 0.2M Glycine-HCl pH 2.3
i. equilibrate with 0.02M NaP+0.15M NaCl, pH 7.0 buffer
[10 ml size cartridge]
j. same coupling procedure with an approximately 50× scale down
[Coupling efficiency 80–90%]

2. Testing Procedure
a. 10 ml cartridge coupled to protamine
50 mls of plasma+20 units/ml heparin (Sigma heparin from Porcine Intestinal Mucosa H-7005; activity 150-180 USPK1 units/mg) flowed through the column at a rate of 1 ml/min
b. 100 ml cartridge coupled to protamine 1000 mls of plasma+50 units/ml heparin flowed through the cartridge at a rate of 15 mls/min 3. Assay Methods
a. "A Colorimetric Assay for Chemical Heparin in Plasma," Michael D. Klein et al., *Analytical Biochemistry* 124:59-64 (1982).

This assay employs the metachromasia of azure A when heparin is added. It is useful for 0 to 10 units/ml and does not depend on the anticoagulant activity of heparin. The assay can be used in plasma, whole blood, and buffered saline solutions. The dye and sample are mixed together and then read immediately on a spectrophotometer at 620 nm. Controls include samples of known heparin concentration and a sample that contains no heparin.

b. A Clotting Procedure for the Quantitative Determination of Heparin in Plasma, Sigma Kit #87 B Principle of Test: In the presence of trace amounts of heparin, activated factor X (Xa) is rapidly neutralized by its plasma inhibitor. At a specific time in the initial phase of the reaction between the plasma inhibitor and factor Xa in the presence of heparin, the amount of factor Xa neutralized is proportional to the concentration of the heparin present.

TABLE IX

4. Results:

A. Removal of Heparin from Plasma-Dynamic Test on 10 ml Cartridge Coupled to Protamine.

| Media | Units Heparin Bound per device | Units Heparin Bound per gram media | Units Heparin Bound per mg Protamine Coupled |
|---|---|---|---|
| PHMA | 77 u | 128 u | — |
| #1 PHMA and coupled Protamine | 769 u | 1281 u | 59 u |
| #2 PHMA and coupled Protamine | 551 u | 918 u | 43 u |
| Aminohexyl | 756 u | 1260 u | — |

1 12.98 mg protamine coupled; deactivator used was diethylaminopropylamine.
2 12.86 mg protamine coupled; deactivator used was ethanolamine.

B. Removal of Heparin from Plasma with PHMA + Protamine, 100 ml Size Cartridges.

| 100 ml Cartridge | Units Heparin bound | Units Heparin bound per mg Protamine coupled |
|---|---|---|
| PHMA + protamine #1 | 42,194 units | 120 units |
| PHMA + protamine #2 | 24,490 units | 68.6 units |

1 deactivated with diethylaminopropylamine.
2 deactivated with ethanolamine.

EXAMPLE 14

Polymyxin-B Sulfate Removal of Endotoxin

1. Material Preparation (all buffers/materials prepared with pyrogen-free $H_2O$ and pyrogen-free glassware):
PHMA media in 10 ml columns a. wash with 20 ml $H_2O$
b. 1.5% $NaIO_4$, in $H_2O$, passed through at 1 ml/min for 30 min
c. wash with 20 ml $H_2O$
d. equilibrate with 0.1M Sodium Phosphate buffer, pH 7.5
e. 6 mls of a 5 mg/ml Polymyxin-B Sulfate solution in above buffer is recirculated overnight (0.5 mls/min)
f. uncoupled Polymyxin-B Sulfate washed out with 0.1M Phosphate buffer (saved for determination of amount coupled)
g. column then equilibrated with 0.1M Borate buffer, pH 8.0
h. 20 mls of a 1% ethanolamine solution recirculated with 4×25 mg $NaBH_4$ additions added 60 minutes apart
i. column washed with 0.1M NaP, pH 7.5 buffer and 0.15M HCl+0.25M NaCl, pH 2.7, solution alternately (20 mls each; 2 times for each solution)
j. column equilibrated with 0.1M NaP buffer pH 7.5 for a PHMA 250 ml (12.5 g of media) cartridge—same procedure with an 75X scale-up]

The 10 ml column is the mini-column with a 10 mm diameter.

2. Testing Procedure a. 0.02M NaP+0.15M NaCl pH 7.0+10 mg/ml $E.\ coli$ LPS (Sigma No L-2880 lipopolysaccharide from $E.\ coli$ 05S:B5 phenol extract) flowed at 1 ml/min for 10 ml cartridge and 20 ml/min for 250 ml cartridge.
b. Same as a. except 20 mg/ml BSA added to buffer.

3. Assay Methods for Pyrogen Levels

Test used: Whittaker Bioproducts' QCL1000 Quantitative Chromogenic LAL assay.

Principles of this test: Gram-negative bacterial endotoxin catalyzes the activation of a proenzyme in the Limulus Amebocyte Lysate (LAL). The initial rate of activation is determined by the concentration of endotoxin present. The activated enzyme catalyzes the splitting of p-nitroaniline (pNA) from a colorless substrate and the yellow color is measured photometrically at 405 nm after the reaction is stopped with acetic acid. After standards are run, the correlation between the absorbance and the endotoxin concentration is linear in the 10–200 pg/ml range.

Application of this test: The starting material is diluted with sterile saline to the proper concentration range and assayed to form a curve. The unknown samples, diluted approximately the same way, are assayed against this curve. The pg/ml value obtained for the unknown, times the dilution equals the concentration of endotoxin in the unknown.

4. Results a. Coupling efficiency: When 60 mg of Polymyxin-B Sulfate/gram of activated PHMA is given, 26–31 mg/gram can be coupled.
b. LPS binding capacity (everything dependent on LPS concentration)

| In test procedure A: | |
|---|---|
| 10 ml cartridge | |
| (700–1000) mg/g media | |
| 33.5 µg/mg Polymyxin-B Sulfate | |
| 250 ml cartridge | 43.7 µg/ml PMBS |
| | 530 µg/g media |
| In test procedure B: | |
| 10 ml cartridge | 26.5 µg/mg PMBS |
| 250 ml cartridge | 32.1 µg/mg PMBS |

EXAMPLE 15

Protein A and Protein G Affinity Filters Configured for Radial Flow

Immobilized recombinant Protein A and Protein G were used as model proteins to demonstrate the functions of the affinity separation media. Protein A is a well-known staphylococcal-derived protein that interacts with Fc region of immunoglobulins, especially immunoglobulin G. Uses of Protein A include the detection and purification of antibodies and immune complexes, bulk production of immunoglobulin fractions, and monoclonal antibodies, and as a potential for treatment of certain cancers and autoimmune diseases via extracorporeal plasma filtration.

Protein G is an immunoglobulin binding bacterial cell wall protein isolated from group G streptococci; it has recently been cloned and expressed in bacterial cell systems and hence is available in sufficient quantity to fully investigate its properties. Protein G is analogous to Protein A in that it too binds to the Fc region of immunoglobulins but is reported to be a more general IgG binding reagent since it will bind to certain animal IgGs and human IgG subclasses that interact poorly or not at all with Protein A. The Type III receptors (Protein G) are thought to have broader applications in the immunological arena than the Type I Fc Receptor (Protein A).

1. Materials and Methods

Recombinant Protein A was purchased from Repligen Corporation (Cambridge, Mass.). Protein G (Type GXII TM) was supplied by Genex Corporation (Gaithersburg, Md.). Both proteins were immobilized to the new matrix as described in Tables X and XI. The affinity support used was activated to contain aldehyde groups at the end of an 18-atom spacer arm. The extended arm support was selected to prevent steric problems that sometimes occur when macromolecules are immobilized and used to purify equally large macromolecules. All standard chemicals used in the immobilization or evaluation steps were reagent grade and purchased from typical laboratory suppliers. Purified bovine and human IgG fractions (Fraction II, Ill.) were purchased from Sigma Chemical Co. (St. Louis, Mo.). Human serum was obtained from the American Red Cross (Farmington, Conn.) and was partially purified by ion exchange. Polyclonal rabbit antisera to human albumin and goat antisera to human IgG were purchased from Cone BioProducts (Seguin, Tex.) and were also partially purified by ion exchange before use. In one experiment, an affinity purified fraction of goat anti-human IgG was used. Laboratory peristaltic pumps (Rainin) were used during the coupling and testing of the affinity supports in order to achieve the flow rates required. On-line UV monitors (Gilson) were used to monitor the dynamic events. Protein measurements were routinely made by O.D. 280 and verified by Lowry.

Results and Discussion

Since little has been reported about the optimum coupling conditions for the ligands under study, two sets of experiments were performed. In the first set, as reported in Table X, both ligands were coupled via glutaraldehyde to an amino affinity support; in this case the ligand was stabilized by using sodium borohydride as the reducing agent. Comparative testing with various polyclonal IgGs consistently showed higher elution capacity from the Protein G column.

The results shown in Table XI establish a few additional points: (1) trimethylamineborane is also an acceptable reducing agent for Protein A and Protein G, (2) the new matrix is readily scaleable—a 2.5×increase in column size and in amount of ligand coupled yield close to perfect scale-up in the amount of IgG that is eluted from both columns, and (3) the relatively weaker interaction of bovine species with Protein A is in agreement with published literature.

Although in general the data agrees with published literature, especially the weak interaction observed between goat and bovine IgGs with Protein A, it should be kept in mind that both immobilized ligands are recombinant in nature, and therefore results may vary depending on the source and consistency of the cloned product. Total protein recoveries from all experiments ranged from 91–100%, suggesting that non-recoverable protein loss to the matrix is not a factor.

TABLE X

COMPARISON OF PROTEIN A AND PROTEIN G COLUMNS: INTERACTION WITH VARIOUS POLYCLONAL IgGs WITH SODIUM BOROHYDRIDE AS REDUCING AGENT

| Species | Protein A Capacity (mg) | Ratio | Protein G Capacity (mg) | Ratio |
|---|---|---|---|---|
| Human IgG (pure) | 17.52 | 3.5 | 19.81 | 4.52 |
| Human IgG (serum) | 16.85 | 3.37 | 16.85 | 3.76 |
| Rabbit AHSA (antiserum) | 10.16 | 2.03 | 16.54 | 3.78 |
| Goat AHIgG (affinity purified) | 6.88 | 1.38 | 19.44 | 4.44 |

Coupling and Test Conditions: Laboratory-size columns containing 1 gram of Type A matrix (1,6-diaminohexane coupled matrix) were used. Columns were activated with 0.25% glutaraldehyde in 0.1 M borate buffer, pH 8.2. After washing the columns free of excess glutaraldehyde, ligand solution (5 mg/ml) in the same buffer was recirculated for 4 hours. Columns were reduced with sodium borohydride (NaBH$_4$) and blocked with 1% glycine ethyl ester hydrochloride, pH 8.2. The blocking and reduction step was allowed to proceed overnight for convenience. After several washes alternating with buffer (0.05 M sodium phosphate, pH 7.6, with 0.25 M NaCl) and 0.2 M glycine-HCl (pH 2.3), the columns were washed with 0.15 M NaCl acidified to pH 2.0, then equilibrated with 0.05 M sodium phosphate buffer with 0.25 M NaCl, pH 7.6, prior to applying the IgG fractions. Flow rate throughout was 2 ml/min. To provide maximum contact time, all IgG solutions recirculated for 1 hour. Elution of the IgG column was accomplished with glycine-HCl, pH 2.3. As determined by Lowry, the Protein A column coupled at 100% efficiency and contained 5 mg of immobilized ligand, whereas the Protein G column coupled at 88% efficiency and contained 4.4 mg of immobilized ligand. To provide consistent testing, the test solutions were adjusted (by dilution) so as to offer 50 mg (±5 mg) total IgG to each column. Protein A and Protein G columns were tested simultaneously with the same starting pool of test sample to avoid the possibility of variation in the starting sample. The ratio provided above is defined as the interaction ratio between total eluted IgG and immobilized ligand (i.e., eluted IgG/bound ligand).

total eluted IgG and immobilized ligand (i.e. eluted IgG/bound ligand).

TABLE XI

COMPARISON OF PROTEIN A AND PROTEIN G COLUMNS: INTERACTION WITH VARIOUS POLYCLONAL IgGs WITH TRIMETHYLAMINEBORANE AS REDUCING AGENT

| Species | Protein A Capacity (mg) | Ratio | Protein G Capacity (mg) | Ratio |
|---|---|---|---|---|
| Human IgG (pure) | 43.99 | 3.55 | 46.66 | 4.42 |
| Human IgG (serum) | 39.03 | 3.15 | 40.05 | 3.79 |
| Bovine IgG (pure) | 25.19 | 2.03 | 44.44 | 4.20 |

Coupling and Test Conditions: Slightly larger columns containing 2.5 g of Amino type matrix of Table X were used to test the scale-up efficiency of the new matrix. Columns were activated and ligands coupled as described in Table X. In this study trimethylamineborane was used as the reducing agent. This reagent was first dissolved in 1 M acetic acid and then combined with glycine-ethyl ester hydrochloride (final concentration 1.5%, pH 6.0) to block unbound sites. Blocking and reduction were continued overnight. The colums were washed, equilibrated, and tested as described above. As determined by Lowry, the Protein A column coupled at 99% efficiency and in this case contained 12.4 mg of immobilized ligand, whereas the Protein G column coupled at 97% efficiency and contained 10.6 mg of immobilized ligand. To provide consistent testing, the test solutions were adjusted (by dilution) so as to offer 125 mg (±5 mg) total IgG to each column. Protein A and Protein G columns were tested simultaneously with the same starting pool of test sample to avoid the possibility of variation in the starting sample. As in Table X, the Ratio reported above = Eluted IgG/bound ligand.

The matrix composition and coupling methods are compatible with both ligands. It is proposed, based on the results shown, that the bacterial Fc receptors are coupled to the solid support through non-critical primary amino sites, leaving the Fc receptor sites accessible for interaction with the Fc region of immunoglobulins. The arithmetic scale-up observed when columns containing 2.5×more matrix and immobilized ligand were tested with human IgG demonstrates that larger devices with flow rates in the 100–1,000 ml/min range can be similarly fabricated.

Further support for the scale-up capabilities of the matrix was obtained when human IgG was coupled to a newer form of the matrix, this support differing in that it is pre-activated to the aldehyde form. (Preactivation was accomplished by reacting the glycidyl group of the cellulose bound GMA with a weak acid such as a dilute perchloric acid to produce the dihydroxy form, i.e., PHMA. The PHMA may then be reacted with periodate to give the aldehyde form.) Laboratory results yielded ligand immobilization capacities of 10 mg, 80 mg, and 3,000 mg for devices capable of flowing at 2 ml/min, 5 ml/min, and 125 ml/min. The largest affinity filter was capable of isolating more than 3 grams of IgG from goat anti-human anti-serum.

EXAMPLE 16

Preparation of a Tangential Flow Cartridge with Immobilized Protein A

Protein A was immobilized to hexamethylenediamine derivatized matrix configured in a 250 mL (housing volume) tangential flow cartridge containing 13.8 gm of matrix. The cartridge was first equilibrated with 0.1 M borate buffer, pH 8.2 (about 2000 mL) then treated with 7 mL of a 10 mg/ml solution of protein A, pH 8.2, was recirculated through the cartridge overnight (21 hrs). The flow rate was about 100 mL/min for the first 2.5 hrs, 50 mL/min for the next 1.5 hrs and then 25 mL/min for the remaining time.

The cartridge was then stabilized by adding 5 mL of a 26% solution of glycine ethyl ester, pH=8.2, to the existing solution so the final concentration equals approximately 1% (dead volume is approximately 130 mL). Two portions of sodium borohydride (100 mg) were added 20 min. apart from one another and the solution was recirculated for an additional four hours. The cartridge was then washed with buffer, pH=8.2, and the eluant reserved as a control for protein determination.

The column was deactivated by recirculating 500 mL of a 1% glycine ethyl ester solution, pH TM 8.2, through the cartridge. Sodium borohydride (4×250 mg each) was then added at 30 minute intervals. After about 1½ hours, the solution was allowed to recirculated at 4° C. overnight. Then, four portions of sodium borohydride (400 mg) were added (at 45 min. intervals) and the solution allowed to recirculate for about four hours at room temperature.

Figure 26:
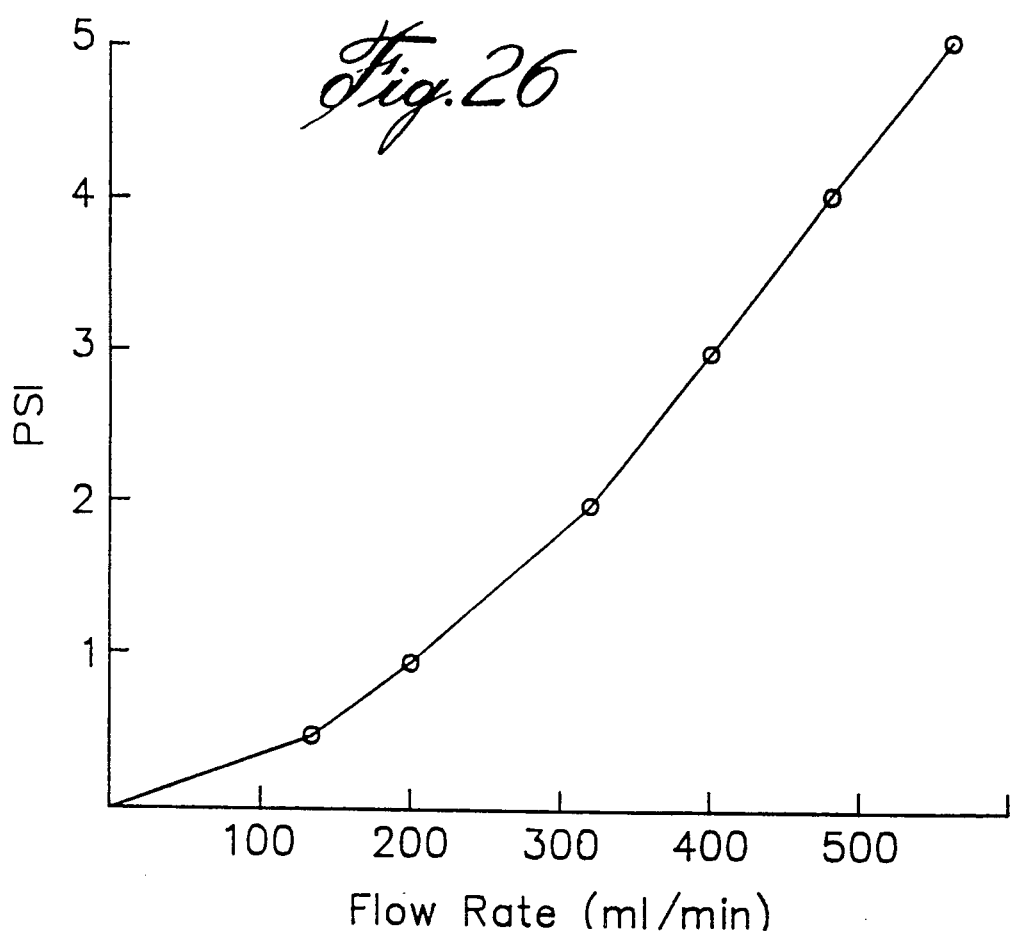
FIG. 26 depicts a graph of the pressure differential ($\Delta p$) between the inlet and outlet of a tangential flow cartridge, which contains immobilized protein A, for various flow rates.

The column was then washed with the following solutions:

680 ml 0.1M borate, pH=8.2
1140 ml 0.2M glycine-HCl, pH TM 2.3
450 ml 0.1M borate, pH TM 8.2
1140 ml 0.2M glycine-HCl, pH=2.3
450 ml pH 6.5 buffer
570 ml 0.2M glycine-HCl
570 ml pH 6.5 buffer 70 mg of protein A was coupled to the matrix based on the Lowry color test, as described above. A graph of the pressure differential ($\Delta p$) versus flow rate (ml/min) appears in FIG. 26.

The tangential flow cartridge was then tested for H$\gamma$G purification. Three experiments were conducted at various flow rates. H$\gamma$G ws dissolved in 0.05 M phosphate buffer (5 mg/ml), pH 7.6 containing 0.25 M NaCl and recirculated at flow rates of 25, 100, and 140 mL/min for 60 minutes. As shown in Table XII, the capacity of the column was only slightly higher at 100 mL/min flow (208 mg) than at 50 mL/min (194 mg) and at 25 ml/min (195 mg).

TABLE XII

| Flow Rate (mls/min) | H$\gamma$G Offered mg | Washing Vol ml | Elution Cap mg | Elution Vol | Inter. Ratio | Recovery % |
|---|---|---|---|---|---|---|
| 50 | 747 (5 mg/ml) | 1920 | 194 | 1500 | 2.78 | 93 |
| 100 | 683 (5 mg/ml) | 2000 | 208 | 1700 | 2.97 | 95 |
| 25 | 683 (5 mg/ml) | 2160 | 195 | 1700 | 2.78 | 95 |

In another experiment, undiluted plasma (70 mL), pH=7.8, was recirculated for 60 min at 75 ml/min. As shown in Table XIII, 98% recovery of IgG was observed.

| Total O.D.$_{280}$ offered | Washing vol ml | Elution Cap (mg) (1) O.D.$_{280}$ (2) Lowry (O.D.$_{650}$) | Elution Vol (ml) | Inter. Ratio | Recovery % |
|---|---|---|---|---|---|
| 4061.4 | 4000 | (1) 298 (2) 146 | 2000 | (1) 4.25 (2) 2.09 | 98 |

Figure 27:
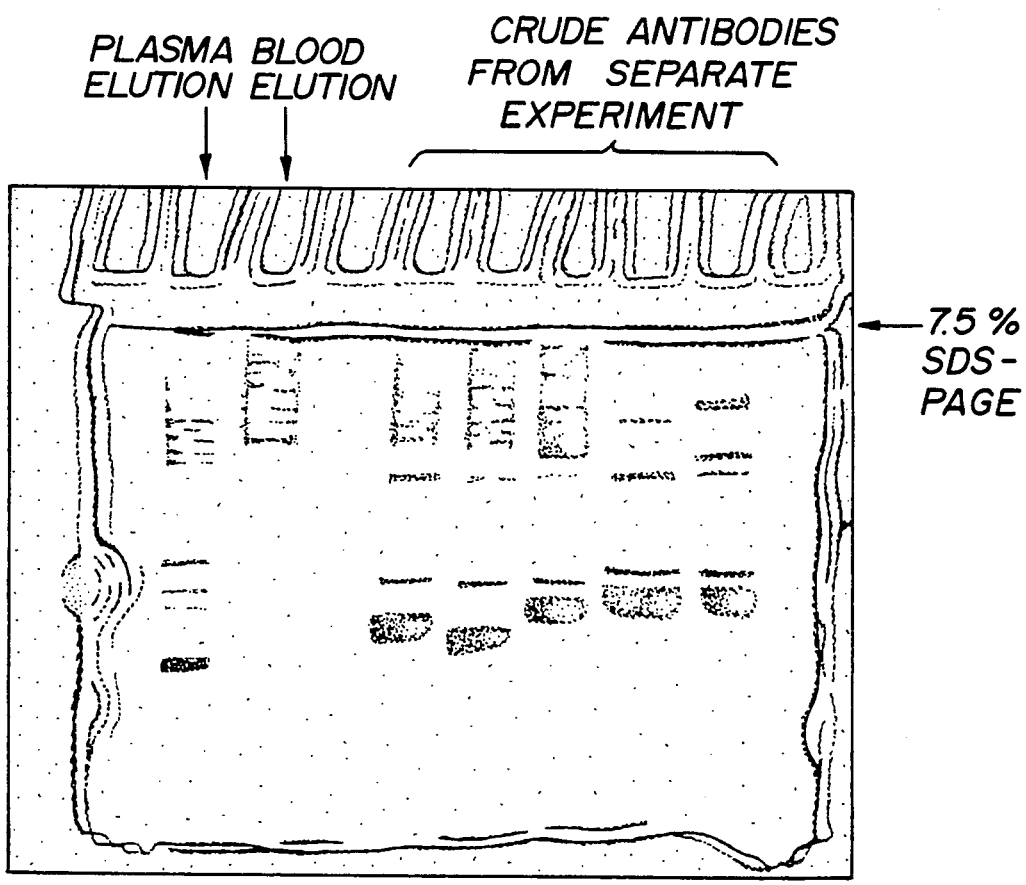
FIG. 27 depicts a gel electrophoresis of IgG obtained from plasma and blood by purification through a tangential flow cartridge containing immobilized protein A.

In a third experiment, IgG within hemolysed blood (2 month old blood kept at 4° C.) was purified. The tangential flow cartridge was first equilibrated with 0.3 NaCl, pH 7.8, then the cartridge is emptied and refilled with hemolysed blood (50 ml), pH=6.76 (unadjusted). The blood was then recirculated for 60 min at 75 ml/min and the IgG eluted. As shown in Table XIV, the amount of IgG eluted was 486.4 mg based on O.D.$_{280}$ and 203 mg based on the Lowry method, O.D.$_{650}$. As shown in FIG. 27, the purity of the IgG was >95%.

A summary of the testing results appears in Table XIV.

TABLE XIV

SUMMARY OF TESTING RESULTS

| Protien A | Testing Conditions | Testing Substance | Elution Capacity | Inter. Ratio |
|---|---|---|---|---|
| (1) offered (2) coupled | (1) Flow Rate (2) pH and buffer (3) contact time | | (1) O.D.$_{280}$ based (2) O.D.$_{650}$ based | (1) O.D.$_{280}$ based (2) O.D.$_{650\ based}$ |
| (1) 70 mg (2) 70 mg (100%) | (1) 50 mls/min (2) pH = 7.6 with 0.25 M NaCl, NaP | H G 747 mg (5 mg/ml) | (1) 194 mg (2) — | (1) 2.78 |

TABLE XIV-continued

SUMMARY OF TESTING RESULTS

| Protien A | Testing Conditions | Testing Substance | Elution Capacity | Inter. Ratio |
|---|---|---|---|---|
| | (3) 60 min | | | |
| (1) 70 mg | (1) 100 mls/min | H G | (1) 208 mg | (1) 2.97 |
| (2) 70 mg (100%) | (2) pH = 7.6 with 0.25 M NaCl, NaP | 683 mg | (2) — | |
| | (3) 60 min | (5 mg/ml) | | |
| (1) 70 mg | (1) 25 mls/min | H G | (1) 194 mg | (1) 2.78 |
| (2) 70 mg (100%) | (2) pH = 7.6 with 0.25 M NaCl, Nap | 682 mg | (2) — | |
| | (3) 60 min | (5 mg/ml) | | |
| (1) 70 mg | (1) 75 mls/min | 70 ml un- | (1) 298 mg | (1) 4.25 |
| (2) 70 mg (100%) | (2) pH = 7.6 with 0.25 M NaCl, NaP | diluted H. plasma pH adjusted to 7.8 | (2) 146 mg | (2) 2.086 |
| | (3) 60 min | | | |
| (1) 70 mg | (1) 75 mls/min | 50 ml un- | (1) 486 mg | (1) 6.94 |
| (2) 70 mg (100%) | (2) 0.3 M NaCl pH adjusted 7.8 | diluted H. blood, pH 6.76 | (2) 203 mg | (2) 2.9 |
| | (3) 60 min | | | |

EXAMPLE 17

Comparison of Different Ligands on Adsorption of Heparin from Blood in Static Tests Experimental media was placed in a test tube. Buffered saline, human plasma, and whole blood were made to contain 10 or 20 units/ml heparin (Sigma Heparin from Porcine Intestinal micosa H-7005; activity 150-180 USPKI U (units)/mg). Test fluid was left in contact with media for 30 min, then samples were centrifuged for approximately 5 min at low speed, just until media was pelleted.

A colorimetric assay for heparin in plasma published by Michael D. Klein in *Analytical Biochemistry* 124:59–64 (1982) was used (see Example 13).

Figure 19:
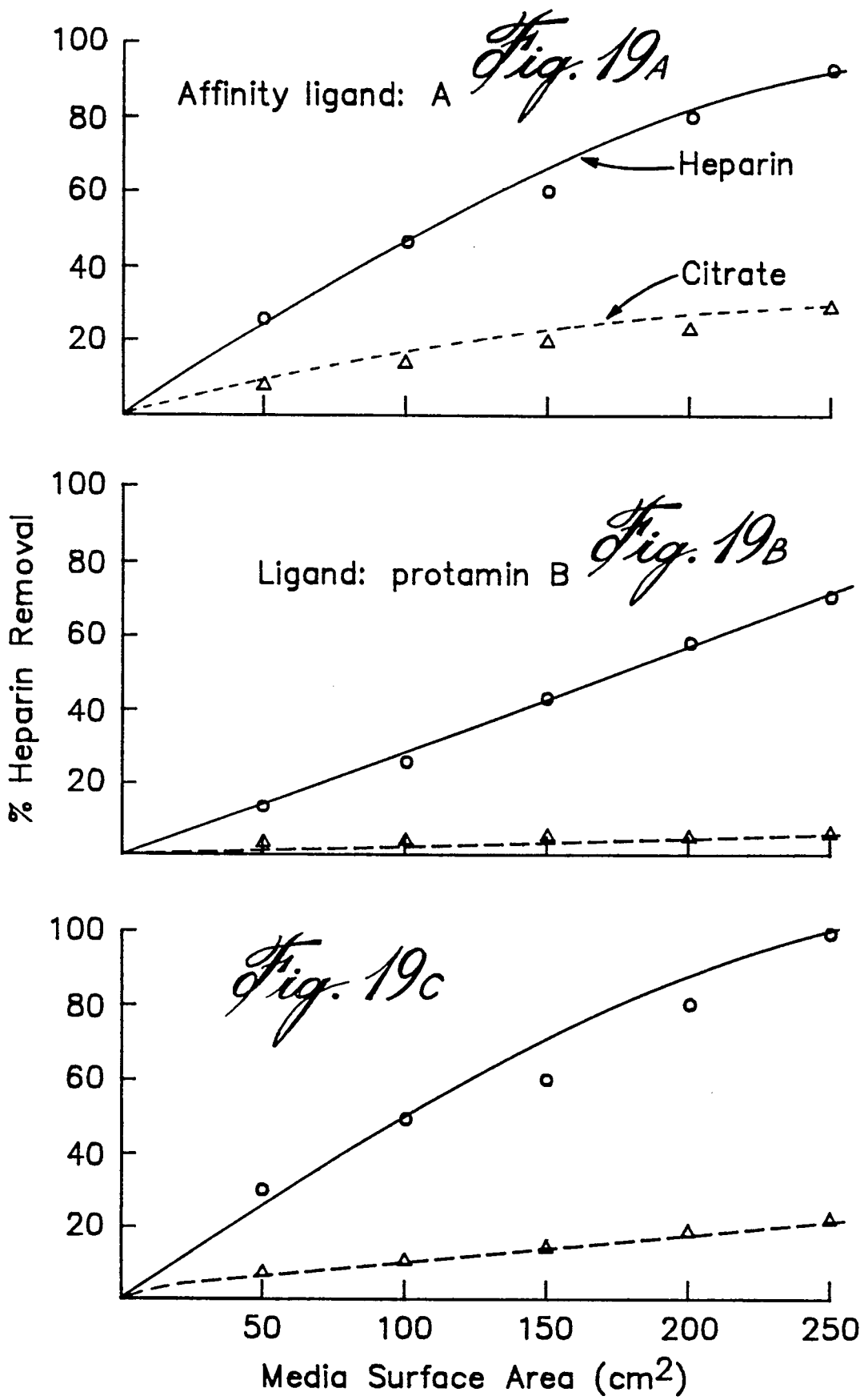
FIG. 19A depicts a graph showing the percent heparin removal versus the surface area for affinity ligand A.
FIG. 19B depicts a graph of the percent heparin removal versus the surface area for the ligand protamin B.
FIG. 19C depicts a graph of the percent heparin removal versus the surface area for the ligand C.

Graphs depicting the relationship between surface area and % heparin removal for the three affinity ligands (0.1 g media/10 cm$^3$, contain time=1 hr, blood volume=10 mL, heparin concentration 20 U, citrate concentration TM 2.9 mg/mL) are depicted in FIG. 19.

As shown in FIG. 19, the high molecular weight polymer of ligand C (polyethyleneimine ligand) is the strongest heparin adsorbent. 100% of heparin removal is achievable by contacting 10 ml of blood containing 20 U/ml with 250 cm$^2$ media for 1 hour.

Approximately 20% of the 29 mg citrate existing in the blood was also found to be adsorbed by the same media.

Next, the effect of contact time was determined. The results appear in FIG. 20 which depicts the % heparin removal for various times using ligand A (hexamethylenediamine) and protamine.

Experiments were conducted by laminating a piece of Zetaffinity paper of size 7 cm × 7.5 cm or 52.5 cm$^2$ in a 150 ml blood bag. 680 U of heparin (45% × 150 ml × 10 U/ml) was found to be removed overnight with Ligand A, which corresponds to a media capacity of 13 U heparin removed per cm$^2$ paper.

Figure 20:
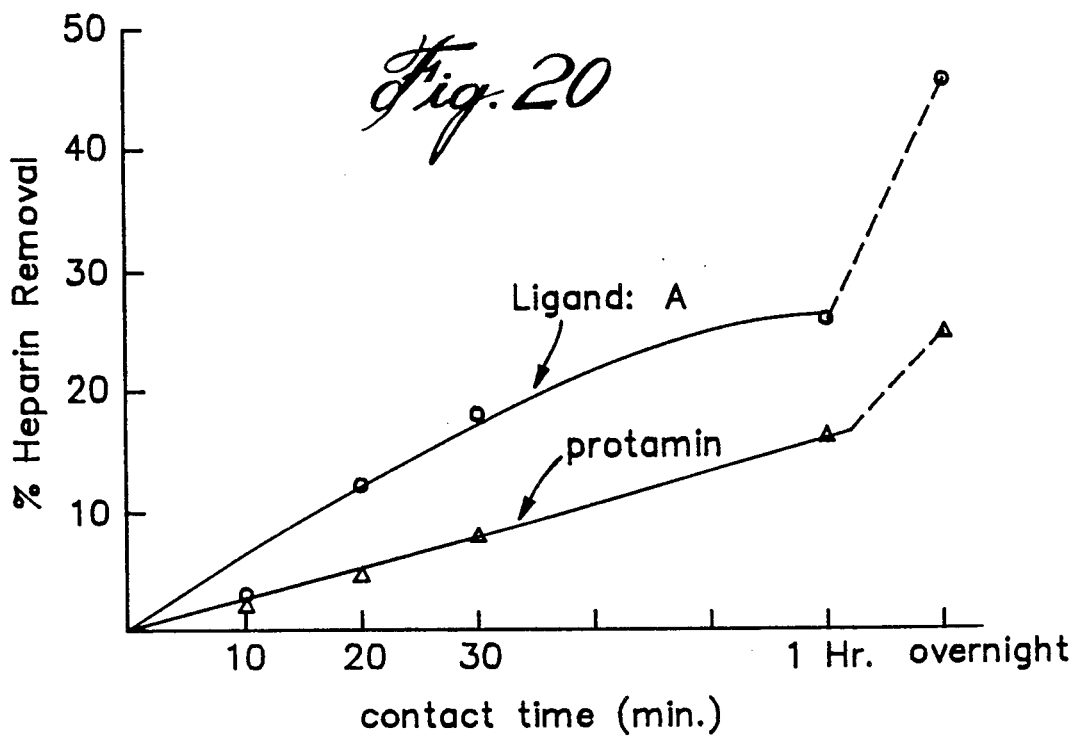
FIG. 20 depicts a graph of the percent heparin removal versus the contact time for two media (A and protamin)
Figure 21:
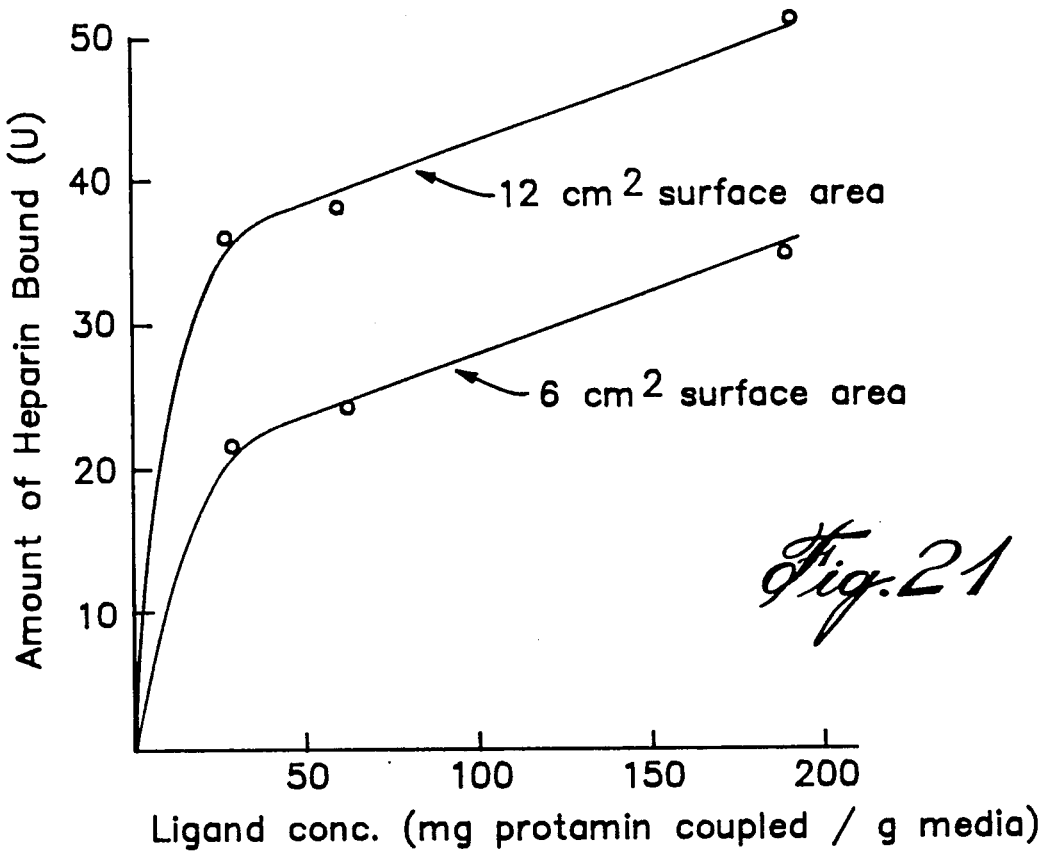
FIG. 21 depicts a graph of the amount of heparin bound versus the ligand concentration (protamin) for two surface area quantities.

The results depicted in FIG. 20 show that approximately 1 hour contact time is required to have 90% of the absorption sites utilized for binding heparin.

Next, the effect of protamine concentration on the amount of heparin removed from blood was determined. Various concentrations of ligand (0–200 mg protamine/g media) were contacted with 10 mL of blood having 20 U/mL heparin. The samples were allowed to react for 1 h then the amount of heparin bound determined as described above. A graph depicting the amount of heparin bound to the matrix for two sheets of matrix material having surface areas of 12 cm$^2$ and 6 cm$^2$ are shown in FIG. 20.

EXAMPLE 17

Preparation and Dynamic Testing of a Tangential Flow Cartridge for Heparin Removal A tangential flow cartridge was constructed based on the "250 size" cartridge as shown in FIG. 11. Webbing material as first wrapped around the core twice to prevent the media from blanking off the core. Then, the media and impermeable film are wrapped together with the webbing material until a diameter of 2.600 inches was obtained. The media and film were then cut and a 4-inch piece of webbing was inserted 2 inches between the media and the preceding wrap of webbing. Finally, the subassembly is held together with elastic bands and then capped with polypropylene end caps. The 250 mL size cartridge (housing volume) contains 14.4 grams of matrix with a total surface area of 180 cm$^2$.

Figure 23:
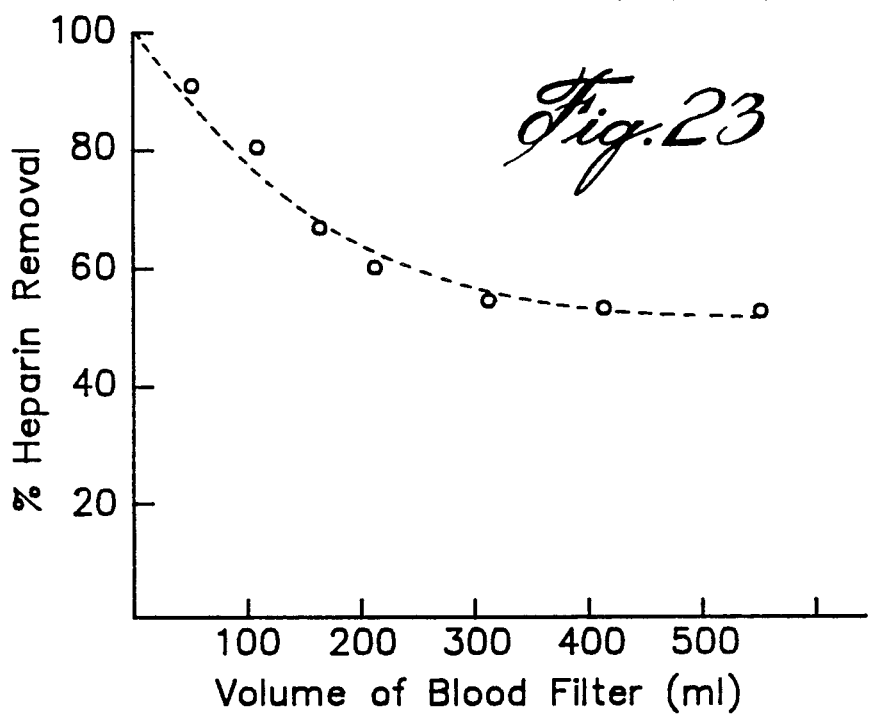
FIG. 23 depicts a graph of the percent heparin removal versus volume of blood filtered.
Figure 24:
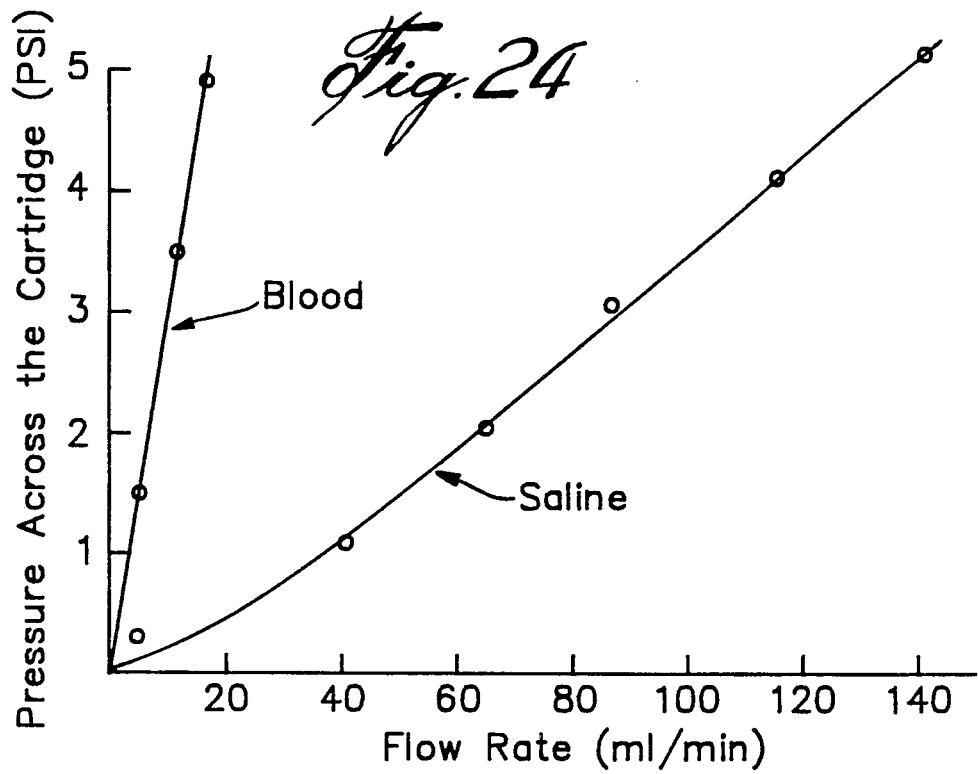
FIG. 24 depicts a graph of the pressure differential ($\Delta p$) the inlet and outlet of a tangential flow cartridge versus flow rate for blood and saline.
Figure 25:
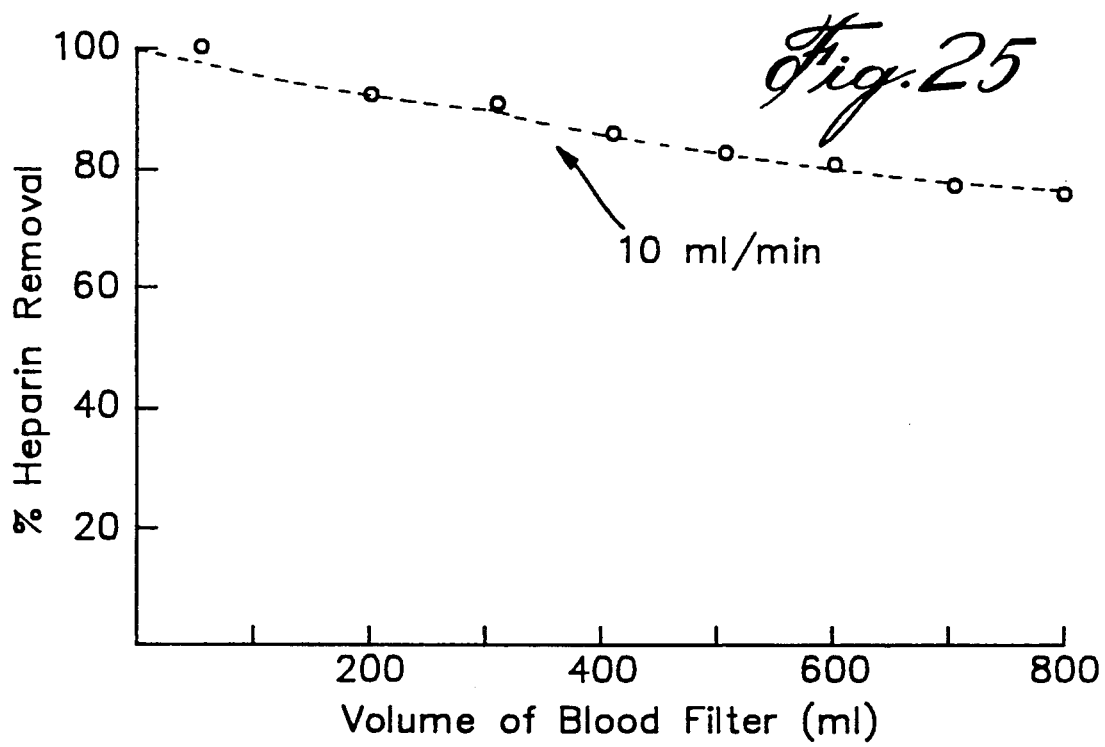
FIG. 25 depicts a graph of the percent heparin removal versus volume of blood filtered through the tangential flow cartridge.

The tangential flow cartridge was thoroughly flushed with saline solution at 50 ml/min. One unit of blood was doped with 10 U/ml heparin and pumped through the pre-flushed cartridge at a flow rate of 12 ml/min ($\Delta p = 1.5$ psi). The filtered blood was fraction-collected at the last 10 ml per every 100 ml fraction. Heparin concentration in each fraction was analyzed by the colorimetric assay and plotted as shown in FIG. 23. FIG. 23 shows that approximately 70% of the heparin was removed. In a separate experiment (data not shown), 80% of the heparin was removed by passing two units of blood through an 800 size cartridge.

Figure 22:
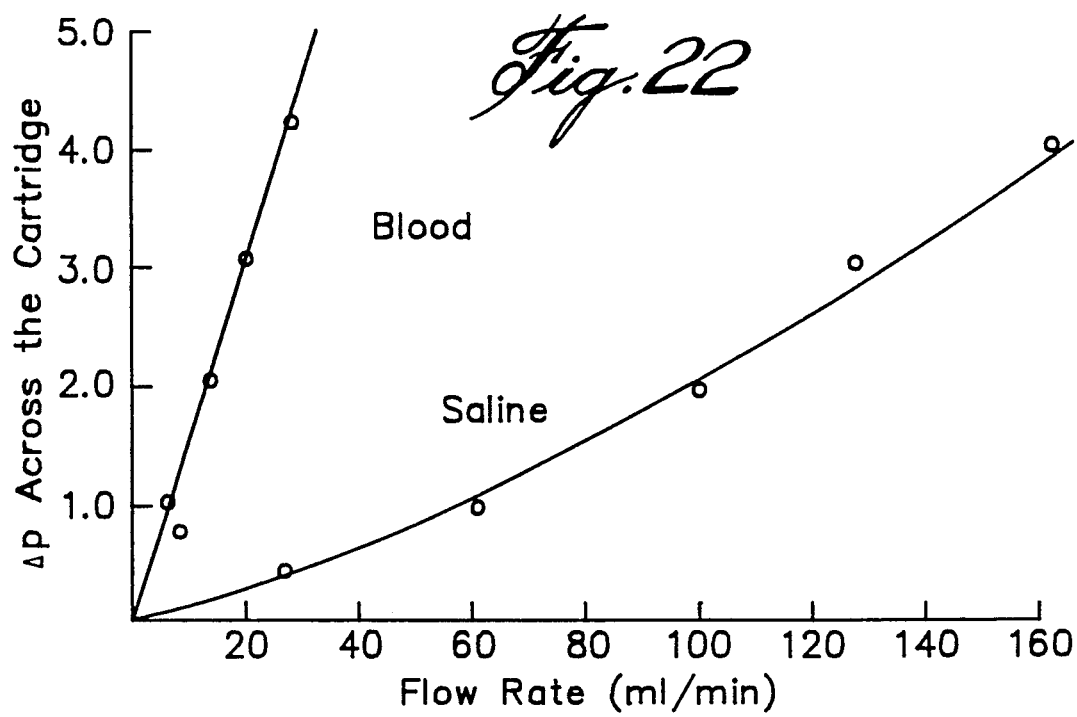
FIG. 22 depicts a graph showing the pressure differential ($\Delta p$) between the inlet and outlet of a tangential flow cartridge versus the flow rate for blood and saline.

The pressure differential across the tangential flow cartridge at flow rates between 0 and 160 ml/min for blood and saline was then determined. The results in FIG. 22 show that for media having a length of 6'11", the pressure differential for blood increases more rapidly than for saline at increasing flow rates.

In Table XV, the analysis of blood components for various volumes of filtered blood for the 250 mL size tangential flow cartridge is depicted. Table XVI shows the analysis of blood components for various volumes of blood using the 800 mL size tangential flow cartridge.

TABLE XV

FILTRATION OF HEPARIZIZED BLOOD BY TANGENTIAL FLOW CARTRIDGE SIZE 250

| Blood Component | Volume of Blood Filtered | | | | | |
|---|---|---|---|---|---|---|
| | 0 | 100 | 200 | 300 | 400 | 500 |
| Hct ml/100 ml | 35.0 | 28.3 | 33.5 | 34.0 | 35.0 | 28.0 |
| Hb gm/d.1 | 10.9 | 9.5 | 10.8 | 11.0 | 10.6 | 8.9 |
| Hb in plasma | 15.15 | 4.34 | 9.61 | 11.16 | 9.3 | 7.13 |
| RBC $\times 10^6/\mu l$ | 3.59 | 3.04 | 3.49 | 3.59 | 3.43 | 2.56 |
| WBC $\times 10^3/\mu l$ | 5.177 | 3.446 | 4.231 | 4.475 | 4.525 | 3.970 |
| Plat count $\times 10^3/\mu l$ | 227 | 95.5 | 125.5 | 117.5 | 118 | 108.5 |
| Ext. Na/K | 170.8/4.35 | 167.3/2.67 | 163.8/3.96 | 167.0/4.25 | 169.7/4.35 | 166/3.14 |

Flow rate: 12 ml/min
p: 1.5 psi
Cartridge: Cross Flow, HDA, 250 size Media wt = 14.4 g, L = 6'6"

TABLE XVI

FILTRATION OF HEPARIZIZED BLOOD BY TANGENTIAL FLOW CARTRIDGE SIZE 800

| Blood Component | Volume of Filtered Blood (mL) | | | | |
|---|---|---|---|---|---|
| | 0 | 200 | 400 | 600 | 1000 |
| Hct ml/100 ml | 36.5 | 24.8 | 32.5 | 33.0 | 35.0 |
| Hb in blood | 12.6 | 8.5 | 11.5 | 12.0 | 12.4 |
| Hb in plasma | 37.9 | 25.5 | 37.9 | 35.6 | 37.2 |
| RBC $\times 10^6/\mu l$ | 3.78 | 2.64 | 3.49 | 3.58 | 3.59 |
| WBC $\times 10^3/\mu l$ | 3500 | 2145 | 2712 | 2846 | 2898 |
| Platelet count | 95 | 24 | 49 | 38 | 42 |
| Extra Na/K | 157.8/12.41 | 165.8/5.24 | 156.7/10.21 | 157.5/12.13 | 156.0/12.31 |

Cartridge: L = 26'
Flow Rate: 100 ml/min

The potential for affinity purification has been demonstrated on cartridge devices. Simplicity of use, and consistent scale-up capabilities, plus a matrix that is stable enough to be heat-sterilized before ligand attachment, provide possibilities for new approaches to the complex purification schemes presently used to isolate products from recombinant fluids. Availability of new ligands with improved specificity, such as shown with Protein A and Protein G, will further the advances being made in development of more process-oriented affinity supports.

Having now fully described this invention, it will be understood by those skilled in the art that the same can be performed within a wide and equivalent range of parameters, conditions, structures, and uses without effecting the spirit or scope of the invention or of any embodiment thereof.

WHAT IS CLAIMED AS NEW AND DESIRED TO BE SECURED BY LETTERS PATENT OF THE UNITED STATES IS:

1. A modified polysaccharide material which comprises:
   (1) a water-insoluble polysaccharide covalently bonded to a synthetic polymer;
   (2) said synthetic polymer made from
      (a) a polymerizable compound which has an epoxy group capable of direct covalent coupling to said polysaccharide; and
      (b) one or more polymerizable compounds containing
         (i) a chemical group capable of causing the covalent coupling of said synthetic polymer to an affinity ligand or a biologically active molecule, or
         (ii) a hydrophobic chemical group.

2. The material of claim 1 wherein said synthetic polymer is a homopolymer.

3. The material of claim 2 wherein said synthetic polymer is a homopolymer of glycidyl acrylate or glycidyl methacrylate.

4. The material of claim 1 wherein said synthetic polymer is a copolymer.

5. The material of claim 1 wherein said polysaccharide is cellulose.

6. The material of claim 1 wherein said chemical group capable of causing said covalent coupling has been reacted with an affinity ligand.

7. The material of claim I wherein said chemical group capable of causing the covalent coupling of said synthetic polymer to said affinity ligand is selected from the group consisting of a primary amine and an aldehyde.

8. The material of claim 6 wherein said affinity ligand is an enzyme, a nucleic acid, an antigen, an antibody, a saccharide, a lectin, an enzyme cofactor, an enzyme inhibitor or a binding protein.

9. The material of claim 8 wherein said ligand is selected from the group consisting of benzamidine, Protein A, Protein G, polymyxin-B, protamine and heparin.

10. A self-supporting cellulosic fibrous matrix which comprises the material of claim 6.

11. In a method of affinity chromatography, the improvement comprising utilizing as the insoluble ligand support the material of claim 1.

12. In a method of carrying out chemical reactions using an insolubilized biologically active molecule, the improvement wherein the insoluble support for said molecule is the material of claim 1.

13. The methods of any one of claims 11 or 12 wherein said material is in the form of a self-supporting cellulosic fibrous matrix.

14. A process for preparing the modified polysaccharide material of claim 1 which comprises:
   (1) polymerizing said compound (a) which has an epoxy group capable of reacting with the hydroxy group of said polysaccharide, with said compound (b) in the presence of said polysaccharide, under temperature conditions insufficient to cause the covalent binding of said compound (a) to said polysaccharide, to thereby form a synthetic polymer of (a) and (b);

(2) reacting said polysaccharide with said chemical group of compound (a) of said synthetic polymer under conditions sufficient to cause said covalent bonding.

15. A chromatography column for effecting chromatographic separation of at least two components of a sample flowing therethrough comprising:
a housing;
at least one solid stationary phase in said housing, comprising a matrix having chromatographic functionality and being effective for chromatographic means for distributing the sample through the stationary phase; and
means for collecting the sample after the sample has flowed through the stationary phase, wherein said matrix comprises the material of claim 1.

16. A chromatography column for effecting chromatographic separation of at least two components of a sample flowing therethrough comprising:
(1) a housing, said housing comprising:
(a) an inlet housing member, and
(b) an outlet housing member, said inlet housing member and said outlet housing member defining a radially, outwardly expanding stationary phase chamber; and
(2) a stationary phase within said radially outwardly expanding stationary phase chamber, said stationary phase chamber comprising a matrix having chromatographic functionality and being effective for chromatographic separation;
wherein said stationary phase and said radially outwardly expanding stationary phase chamber coact to provide substantially uniform radial distribution of sample across said stationary phase, wherein said matrix comprises the material of claim 1.

17. A chromatography column for effecting chromatographic separation of at least two components of a sample flowing therethrough comprising:
(1) a housing, said housing comprising:
(a) an inlet housing member, and
(b) an outlet housing member, said inlet housing member and said outlet housing member defining a stationary phase chamber; and
(2) a stationary phase within said stationary phase chamber, said stationary phase comprising a matrix having chromatographic functionality and being effective for chromatographic separation,
wherein said stationary phase chamber and said stationary phase coact to distribute sample across said stationary phase, said matrix comprising the material of claim 1.

18. A chromatography column for effecting chromatographic separation of at least two components of a sample flowing therethrough comprising:
(1) a housing, said housing comprising:
(a) an inlet housing member, and
(b) an outlet housing member, said inlet housing member and said outlet housing member defining a radially, outwardly expanding stationary phase chamber; and
(2) a stationary phase within said radially, outwardly expanding chamber, said stationary phase comprising:
(a) matrix having chromatographic functionality and being effective for chromatographic separation, wherein said stationary phase chamber and said stationary phase coact to distribute sample across said stationary phase, said matrix comprising the material of claim 1.

19. A process for effecting chromatographic separation of at least two components of a sample comprising contacting said sample with a self-supporting fibrous matrix comprising a modified polysaccharide material, said modified polysaccharide material comprising:
(1) a water insoluble polysaccharide covalently bonded to a synthetic polymer;
(2) said synthetic polymer comprising
(a) a polymerizable compound which has an epoxy group capable of direct covalent coupling to said polysaccharide; and
(b) one or more polymerizable compounds containing
(i) a chemical group capable of causing the covalent coupling of said synthetic polymer to an affinity ligand or a biologically active molecule, or
(ii) a hydrophobic chemical group.

20. The process of claim 19, wherein said contacting comprises radial flow of said sample through said matrix.

21. The process of claim 19, wherein said contacting comprises tangential flow of said sample across said matrix.

22. A chromatographic device for effecting chromatographic separation of at least two components of a sample, comprising:
(A) a modified polysaccharide material which comprises:
(1) a water-insoluble polysaccharide covalently bonded to a synthetic polymer;
(2) said synthetic polymer made from
(a) a polymerizable compound which has an epoxy group capable of direct covalent coupling to said polysaccharide; and
(b) one or more polymerizable compounds containing
(i) a chemical group capable of causing the covalent coupling of said synthetic polymer to an affinity ligand or a biologically active molecule, or
(ii) a hydrophobic chemical group; and
(B) means for effecting tangential flow of said sample across said modified polysaccharide material.

23. The device of claim 22, wherein said modified polysaccharide material is in the form of a sheet, a corrugated sheet, or tube.

24. A chromatography device for effecting chromatographic separation of at least two components of a sample, comprising:
(1) a cylindrical core,
(2) at least a first and second stationary phases wound around said cylindrical core, wherein
(a) a first phase comprises a modified polysaccharide material which comprises:
(i) a water-insoluble polysaccharide covalently bonded to a synthetic polymer;
(ii) said synthetic polymer made from (1) a polymerizable compound which has an epoxy group capable of direct covalent coupling to said polysaccharide; and
(2) one or more polymerizable compounds containing
  (a) a chemical group capable of causing the covalent coupling of said synthetic polymer to an affinity ligand or a biologically active molecule, or
  (b) a hydrophobic chemical group,
wherein said first phase is in the form of a sheet;
(b) a second phase comprising a means for supporting, separating, and providing channels tangential to said cylindrical core;
(3) means for distributing the sample to said channels;
(4) means for collecting the sample from said channels; and
(5) a cylindrical housing.

25. The device of claim 24, further comprising a nozzle disposed on the end of said cylindrical housing, wherein said means for collecting the sample from said channels comprises one or more grooves along the axial length of said cylindrical core which are in fluid communication with said channels and said nozzle.

26. The device of claim 24, further comprising a nozzle disposed on the end of said cylindrical housing, wherein said means for distributing the sample to said channels comprises one or more grooves along the axial length of said cylindrical housing which are in fluid communication with said channels and said nozzle.

27. The device of claim 24, wherein said means for separating, spacing, and providing channels comprises two arrays of filaments, comprising
(1) a first array spaced parallel to one another and perpendicular to the axis of said cylindrical core, and
(2) a second array of filaments spaced parallel to one another and disposed at an angle to to said first array.

28. The device of claim 27, wherein said first array and said second array are affixed at their crossover points.

* * * * *